(12) United States Patent
Liu et al.

(10) Patent No.: US 10,023,603 B2
(45) Date of Patent: Jul. 17, 2018

(54) PREPARATION OF MONOSACCHARIDES, DISACCHARIDES, TRISACCHARIDES, AND PENTASACCHARIDES OF HEPARINOIDS

(71) Applicant: FORMOSA LABORATORIES, INC., Taoyuan (TW)

(72) Inventors: Yu-Liang Liu, Taoyuan (TW); Ching-Peng Wei, Taoyuan (TW)

(73) Assignee: Formosa Laboratories, Inc., Taoyuan (TW)

( * ) Notice: Subject to any disclaimer, the term of this patent is extended or adjusted under 35 U.S.C. 154(b) by 0 days.

(21) Appl. No.: 15/086,032

(22) Filed: Mar. 30, 2016

(65) Prior Publication Data

US 2017/0015695 A1 Jan. 19, 2017

Related U.S. Application Data

(60) Provisional application No. 62/193,548, filed on Jul. 16, 2015.

(51) Int. Cl.
| | | |
|---|---|---|
| *C07H 1/00* | (2006.01) | |
| *C07H 15/04* | (2006.01) | |
| *C07H 15/18* | (2006.01) | |
| *C07H 23/00* | (2006.01) | |

(52) U.S. Cl.
CPC .............. *C07H 15/04* (2013.01); *C07H 1/00* (2013.01); *C07H 15/18* (2013.01); *C07H 23/00* (2013.01)

(58) Field of Classification Search
None
See application file for complete search history.

(56) References Cited

U.S. PATENT DOCUMENTS

2005/0080042 A1 4/2005 Seifert et al.

OTHER PUBLICATIONS

Dai, J. Org. Chem. 2016, 81, 162-184, published Dec. 9, 2015.*
Codee, J. Am. Chem. Sox. 2005, 127, 3767-3773.*
Office Action, TIPO, dated Jan. 9, 2018.
Jyoti Agarwal and Rama Krishna Peddinti, Synthesis and Characterization of Monosaccharide Derivatives and Application of Sugar-Based Prolinamides in Asymmetric Synthesis, Eur. J. Org. Chem. 2012, 6390-6406.
Jyoti Agarwal and Rama Krishna Peddinti, Glucosamine-Based Primary Amines as Organocatalysts for the Asymmetric Aldol Reaction, dx.doi.org/10.1021/jo1023156 IJ. Org. Chem. 2011, 76, 3502-3505.
Ja'nos Tatai, Pe'ter Fugedi, Synthesis of the putative minimal FGF binding motif heparan sulfate trisaccharides by an orthogonal protecting group strategy, Tetrahedron 64 (2008) 9865-9873.

\* cited by examiner

*Primary Examiner* — Layla D Berry
(74) *Attorney, Agent, or Firm* — Hannah M. Tien

(57) ABSTRACT

The present invention provides preparations of monosaccharides, disaccharides, trisaccharides, and pentasaccharides of heparinoids. The present invention also provides novel monosaccharides, disaccharides, trisaccharides and pentasaccharides for use in the preparation of heparinoids.

1 Claim, 37 Drawing Sheets

C or C derivatives

R'= alkyl or substituted alkyl
; aryl or substituted aryl

C

R= alkyl or substituted alkyl
; aryl or substituted aryl

Block B    Block A    Block B-A

PREPARATION OF MONOSACCHARIDES, DISACCHARIDES, TRISACCHARIDES, AND PENTASACCHARIDES OF HEPARINOIDS

CROSS-REFERENCES TO RELATED APPLICATIONS

The present application claims priority to U.S. Provisional No. 62/193,548 filed on Jul. 16, 2015, incorporated herein by reference in its entirety.

FIELD OF THE INVENTION

The present invention relates to preparation of monosaccharides, disaccharides, trisaccharides, and pentasaccharides of heparinoids and novel monosaccharides, disaccharides, trisaccharides and pentasaccharides for use in the preparation of heparinoids.

BACKGROUND OF THE INVENTION

Vascular thrombosis is a cardiovascular disease indicated by the partial or total occlusion of a blood vessel by a clot containing blood cells and fibrin. In arteries, it results predominantly from platelet activation and leads to heart attack, angina or stroke, whereas venous thrombosis results in inflammation and pulmonary emboli. The coagulation of blood is the result of a cascade of events employing various enzymes collectively known as activated blood-coagulation factors. Heparin, a powerful anticoagulant has been used since the late 1930's in the treatment of thrombosis. In its original implementation, tolerance problems were noted and so reduced dosage was suggested to reduce bleeding and improve efficacy. In the early 1970's, clinical trials did indeed indicate acceptable tolerance was obtainable whilst still preserving antithrombotic activity. Unfractioned heparin (UFH) is primarily used as an anticoagulant for both therapeutic and surgical indications, and is usually derived from either bovine lung or porcine mucosa. Among the modern uses of unfractioned heparin are the management of unstable angina, an adjunct to chemotherapy and anti-inflammatory treatment, and as a modulation agent for growth factors and treatment of hemodynamic disorders.

In the late 1980's, the development of low molecular weight heparins (LMWHs) led to improvements in anti-thrombotic therapy. LMWHs are derived from UFH by such processes as; chemical degradation, enzymatic depolymerisation and γ-radiation cleavage. This class of heparins has recently been used for treatment of trauma related thrombosis. Of particular interest is the fact that their relative effects on platelets are minimal compared to heparin, providing an immediate advantage when treating platelet compromised patients. The degree of depolymerisation of UFH can be controlled to obtain LMWH of different lengths. Dosage requirements for the treatment of deep vein thrombosis (DVT) are significantly reduced when employing LMWH as opposed to UFH, although in general the efficacy of both therapeutics seems to be comparable. In addition, LMWH can be effective as an alternative therapeutic for patients who have developed sensitivity to UFH. Unfortunately, there has recently been a great deal of concern in the use of LMWH due to the perceived potential for cross-species viral contamination as a result of the animal source of the parent UFH.

One way of avoiding the possibility of cross-species contamination, is to prepare heparins by chemical synthesis. This method would also provide the opportunity to develop second generation heparins or heparinoids that can be tailored to target particular biological events in the blood coagulation cascade.

An investigation to determine the critical structural motif required for an important binding event in a coagulation cascade involving heparin, dates back to the 1970's. Some structural features of heparin were defined, but the binding domains of interest remained essentially undefined. Research conducted by Lindahl and co-workers (Proc. Natl. Acad. Sci. USA, 1980, Vol. 77, No. 11, 6551-6555; J. Biol. Chem., 1981, Vol. 256, No. 5, 2389-2394) and separately by Choay and co-workers (J., Annals New York Academy of Sciences, 1981, 370, 644-649) eventually led to the determination that a pentasaccharide sequence constituted the critical binding domain for the pro-anticoagulant cofactor, antithrombin III (AT-III). After determination of the critical heparin sugar sequence, complete chemical syntheses were embarked upon to further prove the theories. Complete syntheses of the pentasaccharide binding domain were completed at similar times by Sinay and co-workers (Pierre Sinaÿ, Jean-Claude Jacquinet, *Carbohydrate Research*, 132, (1984), C5-C9) and by Van Boeckel and co-workers (C. A. A. van Boeckel, T. Beetz, J. N. Vos, A. J. M. de Jong, S. F. van Aelst, R. H. van den Bosch, J. M. R. Mertens and F. A. van der Vlugt., *J. Carbohydrate Chemistry*, 4(3), 1985, 293-321).

Significant difficulties were encountered during both these reported syntheses. The synthesis by Van Boeckel and co-workers provided a method on reasonable scale (156 mg's of final product) and with improved yields compared to the Sinay synthesis, but still only provided an overall yield of 0.22%, (compared with 0.053% for the Sinay synthesis). One particular problem encountered during the final deprotection, was the intermolecular reaction of the hemiacetal (the reducing end functionality of the sugar), which led to the formation dimers and trimers. To reduce the likelihood of this occurring, an α-methyl glycoside of the pentasaccharide was synthesized. The structures of interest are represented in Structure 1, wherein I represents the hemiacetal form, and II represents the α-methylglycoside form.

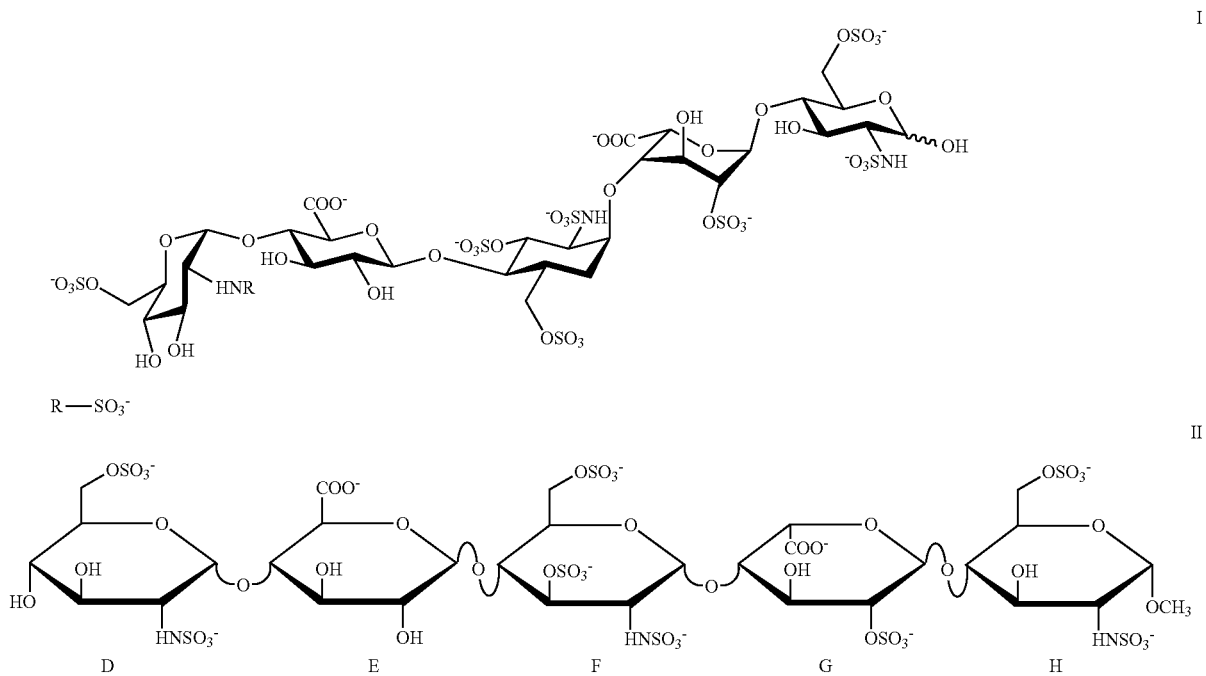

As mentioned, studies have determined that the significant biological event in preventing thrombosis is the binding of a pentasaccharide sequence (*Ann. NY Acad. Sci.,* 1981, 370, 644-649) of heparin, to heparin cofactor antithrombin III (AT-III). As well as pentasaccharide I, the important derivative III has also been prepared by total synthesis (*Biochem. Biophys. Res. Commun.,* 1983, 116, 492-499). The following patents display some relevance to the present invention. U.S. Pat. No. 4,401,662 claims composition of matter on the pentasaccharide AT-III binding sequence of heparin as does U.S. Pat. No. 4,496,550. EP 0,084,999, U.S. Pat. No. 4,818,816, U.S. Pat. No. 7,541,445 and U.S. Pat. No. 8,114,970 detail synthetic methodologies towards pentasaccharide I, and derivative II.

Current synthesis processes of heparinoids, especially for preparation of disaccharides and trisaccharides, still have problems in the following steps with reference to FIG. 1.

Imidate formation: disaccharide-2→disaccharide-3 or trisaccharide-2→trisaccharide-3

Well-known imidate formation reaction was carried out with organic base, 1,8-Diazabicyclo[5,4,0]undec-7-ene (DBU), and trichloroacetonitrile (TCA) as limiting reagent in an organic solvent to obtain imidate. The resultant compound was separated and purified with silica gel column. This reaction requires large amount of organic solvent and time to concentrate to obtain the product.

Glycosylation: Glycosylation of Disaccharide-2 and Monosaccharide C to produce Trisaccharide-1

In Disaccharide-2 molecule, the substituent at the second C atom of Monosaccharide D is OBn. It is prone to form α epimer in general glycosylation reaction without neighboring group effect.

Desilylation: Trisaccharide-1→Trisaccharide-2

In general desilylation reaction, especially for bulky protecting group, tert-butyldimethylsilyl group (TBDMS or TBS group), tetrabutylammonium fluoride (TBAF) was used to remove TBS protecting group, and then separated and purified with silica gel column. This reaction also requires large amount of organic solvent and time to concentrate to obtain the product. It is not easy to remove TBAF effectively in the resultant compounds so that the purified product is difficult to store because of degradation and deterioration.

There is still a need to develop simple, convenient, and efficient synthesis process for preparation of disaccharides and trisaccharides of heparinoids.

SUMMARY OF THE INVENTION

The present invention provides preparation of monosaccharides, disaccharides, trisaccharides, and pentasaccharides of heparinoids. The present invention also provides novel monosaccharides, disaccharides, trisaccharides and pentasaccharides for use in the preparation of heparinoids.

DETAILED DESCRIPTION OF THE INVENTION

Figure 1:
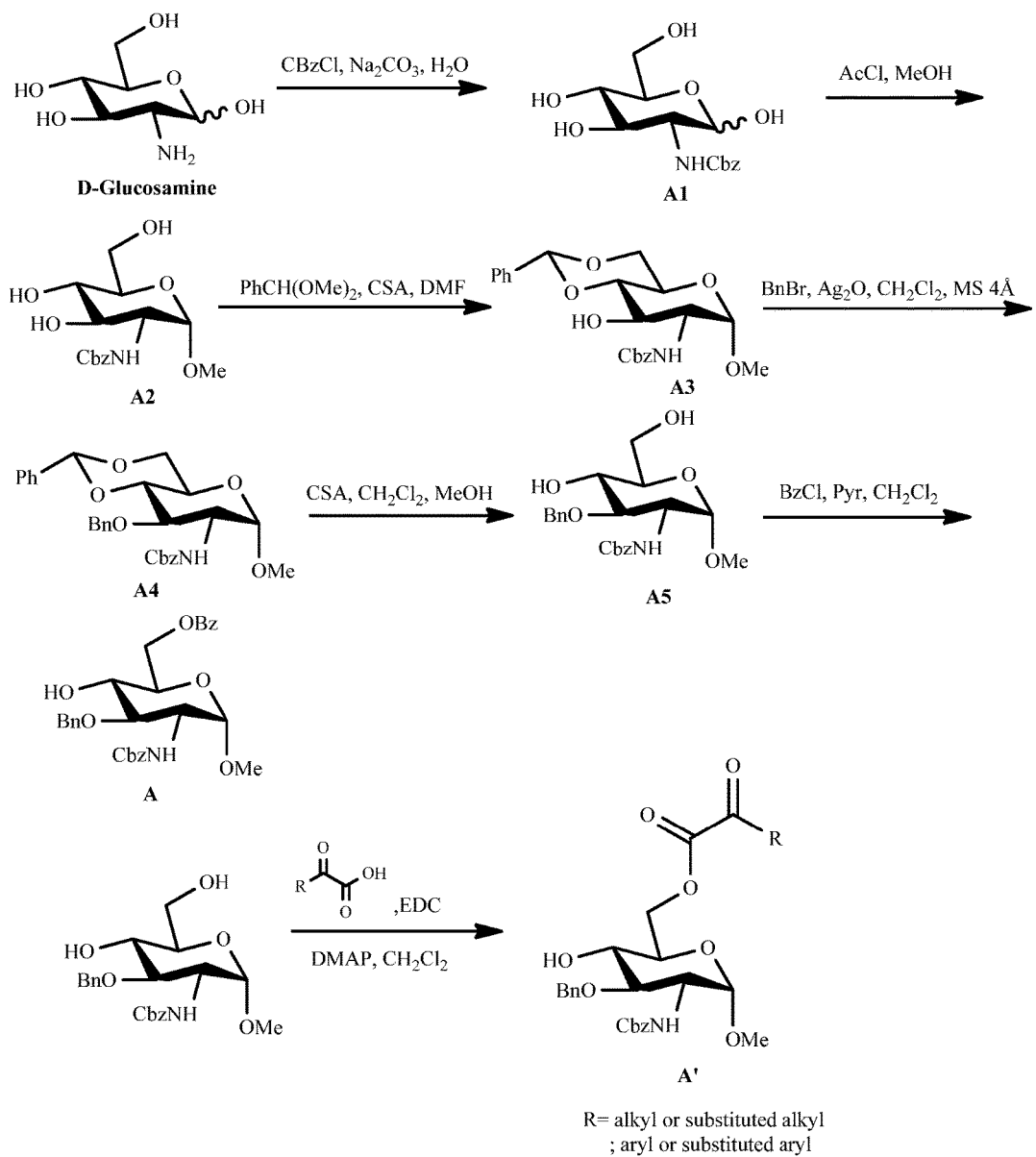
FIG. 1 illustrates the preparation of the monosaccharide of Formula I.
Figure 2:
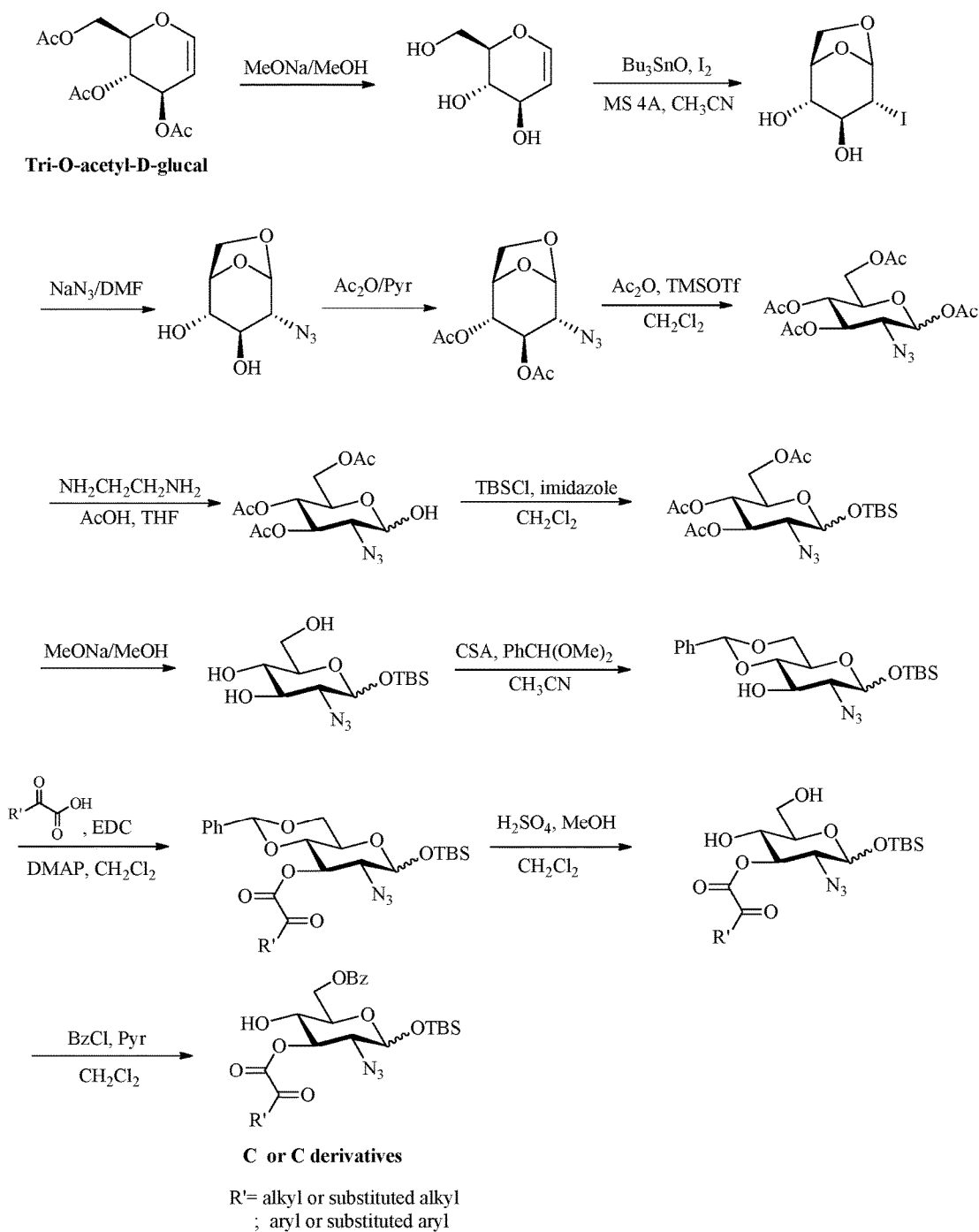
FIG. 2 illustrates the preparation of the monosaccharide of Formula II.
Figure 3:
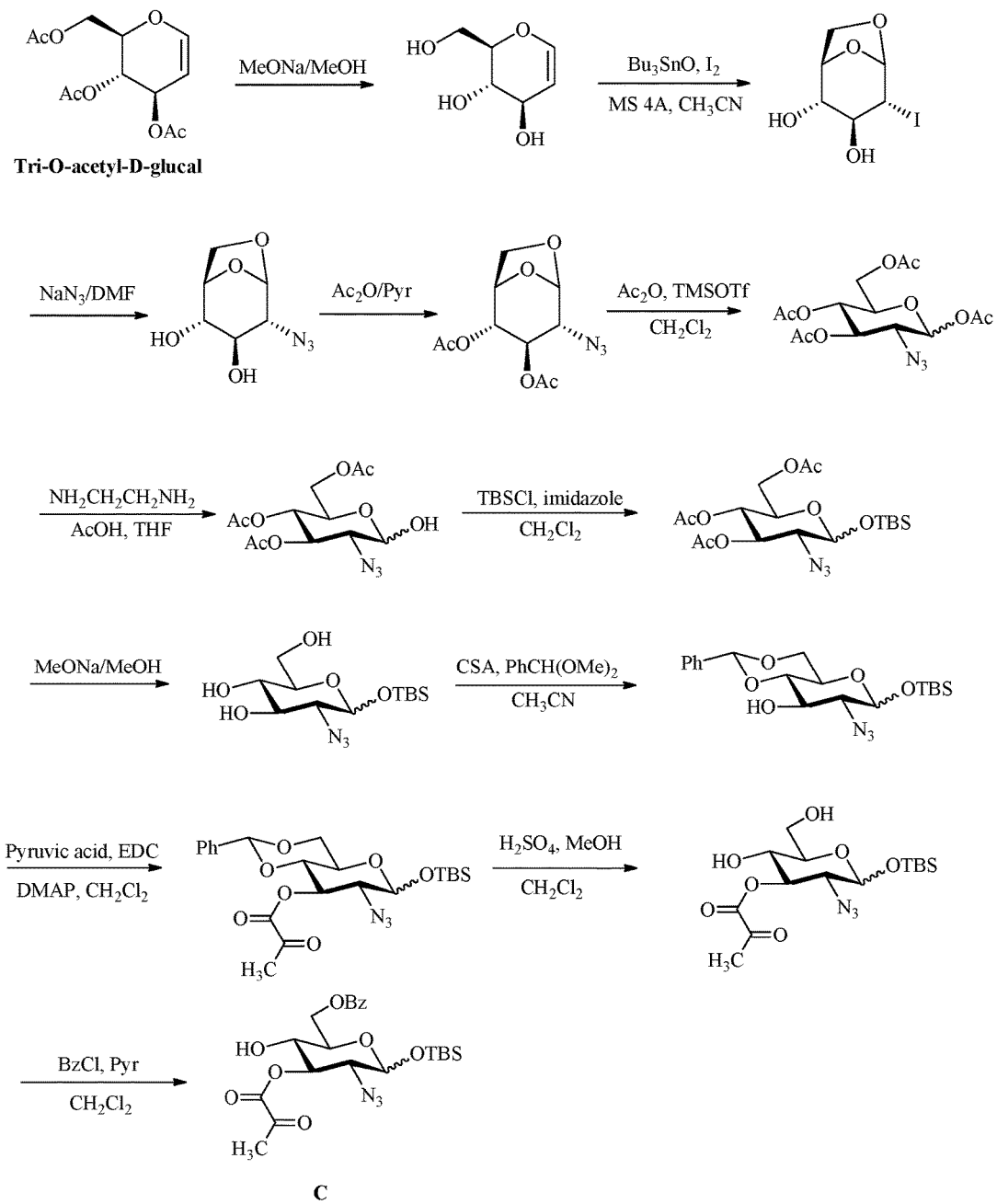
FIG. 3 illustrates one example of preparation of the monosaccharide of Formula II (Monosaccharide C).
Figure 4:
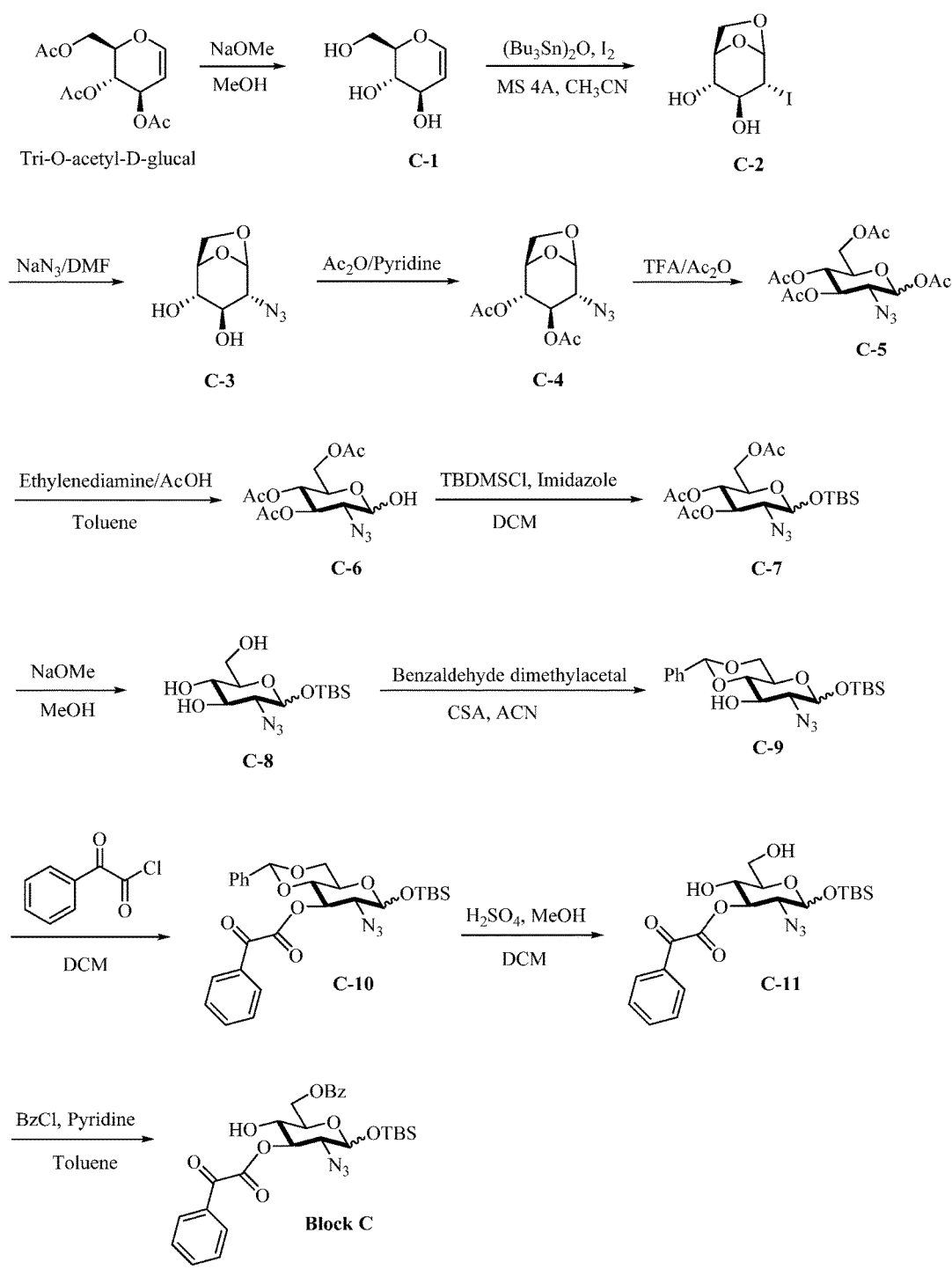
FIG. 4 illustrates another example of preparation of the monosaccharide of Formula II (Monosaccharide C).
Figure 5:
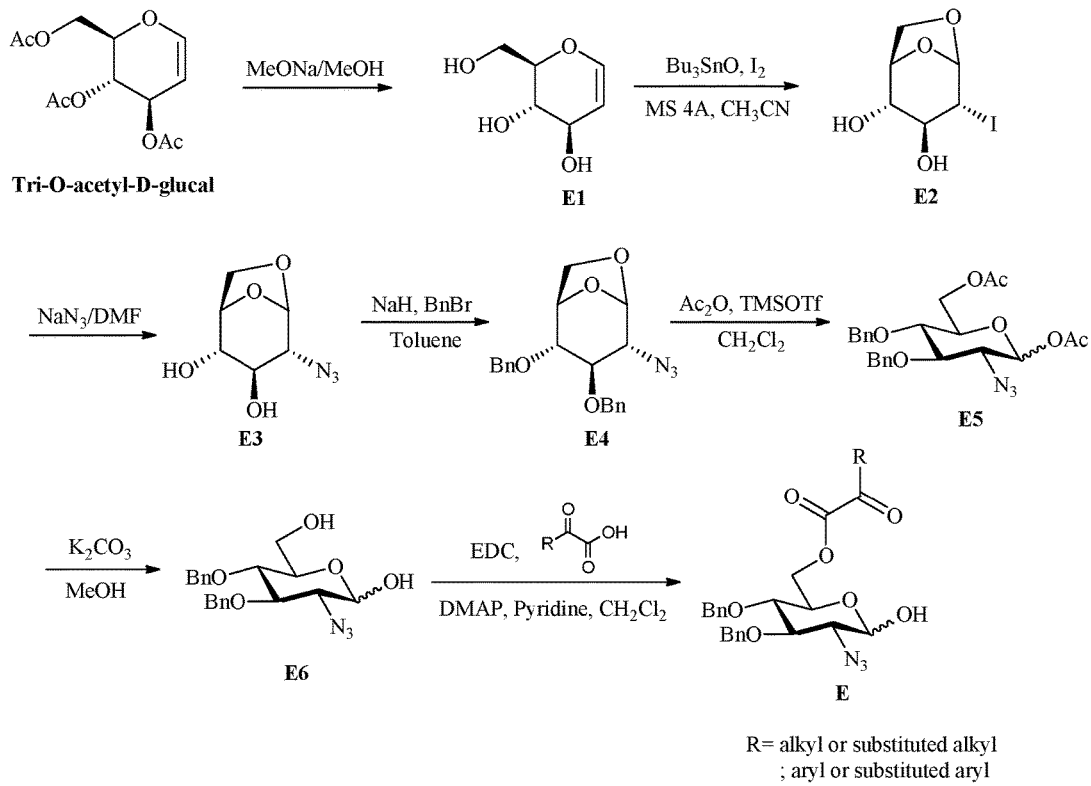
FIG. 5 illustrates the preparation of the monosaccharide of Formula III.
Figure 6:
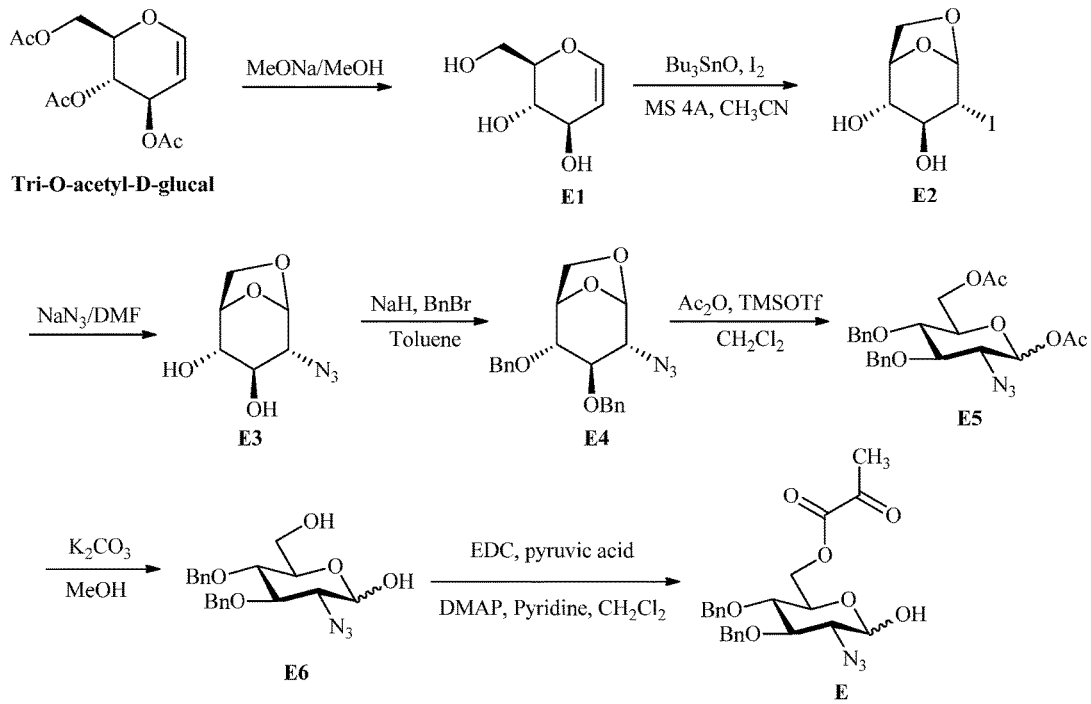
FIG. 6 illustrates one example of preparation of the monosaccharide of Formula III (Monosaccharide E).
Figure 7:
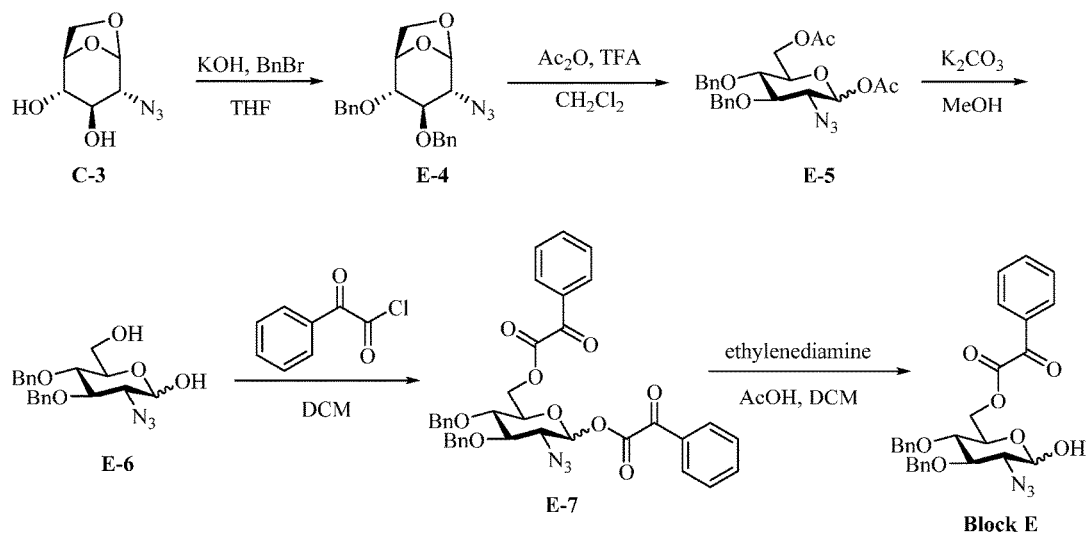
FIG. 7 illustrates another example of preparation of the monosaccharide of Formula III (Monosaccharide E).
Figure 8:
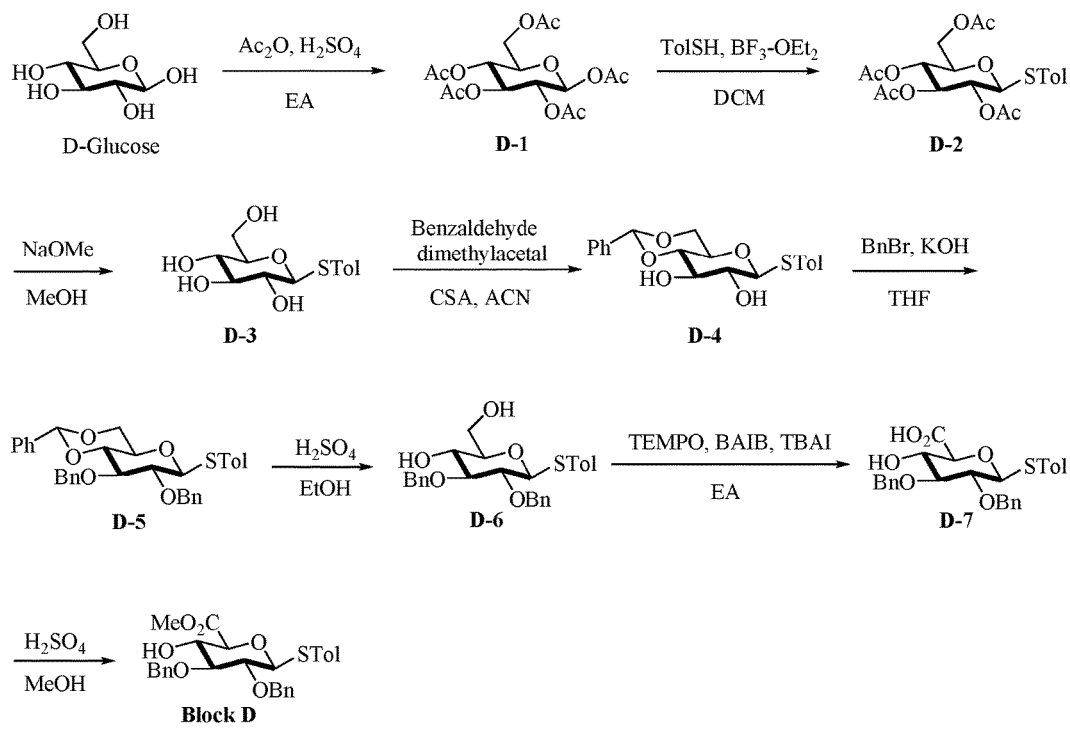
FIG. 8 illustrates one example of preparation of Saccharide D.
Figure 9:
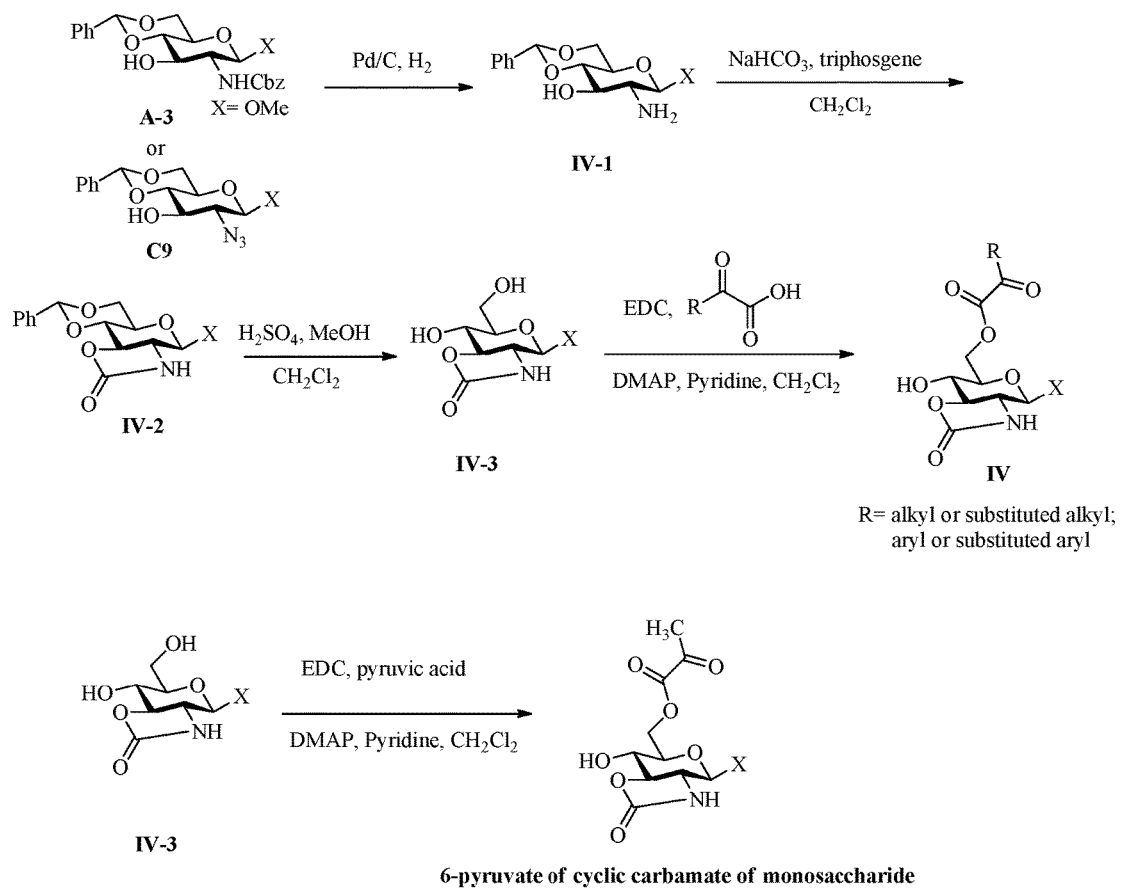
FIG. 9 illustrates the preparation of the monosaccharide of Formula IV.
Figure 10:
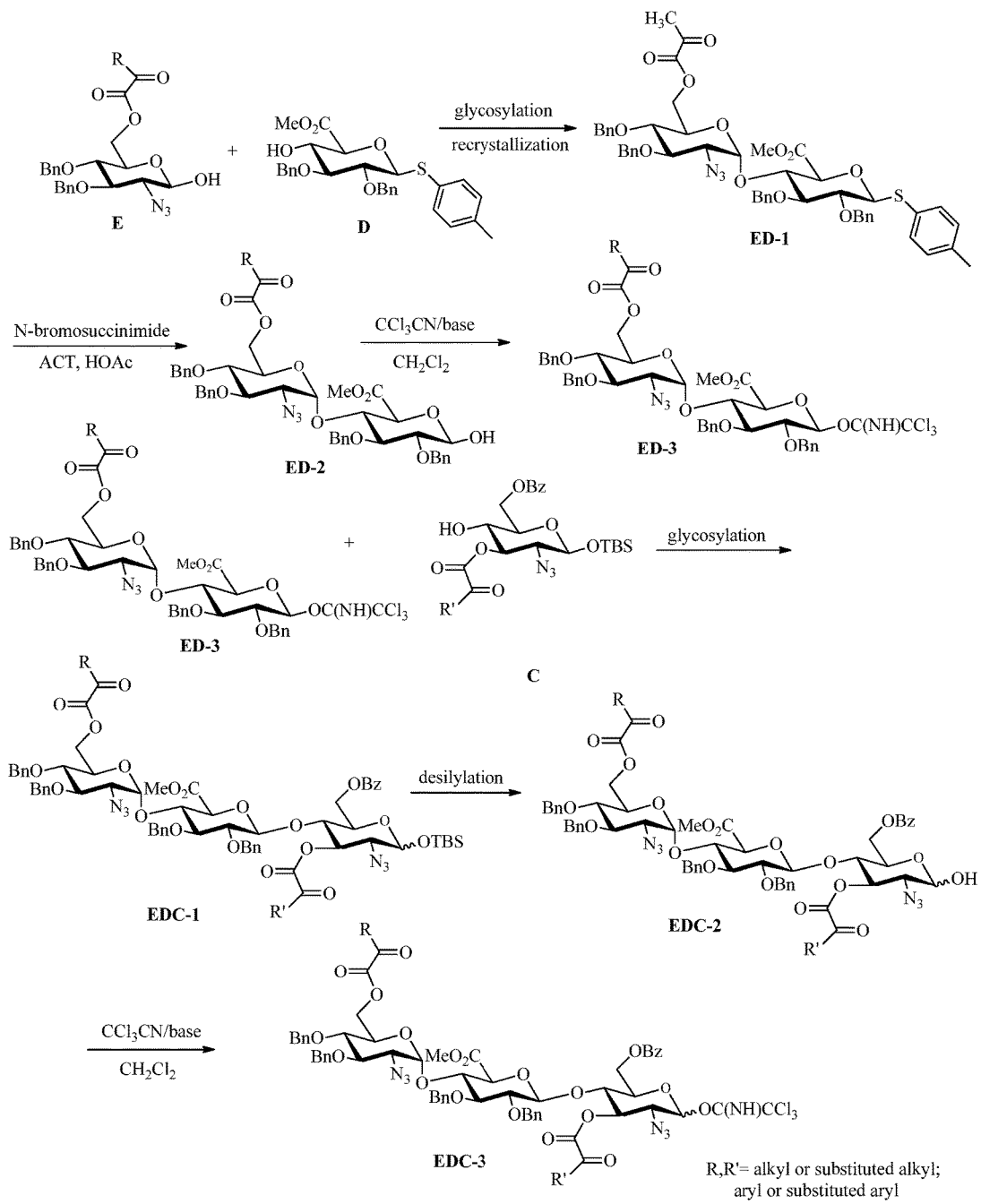
FIG. 10 illustrates the preparation of the trisaccharide of Formula V.
Figure 11:
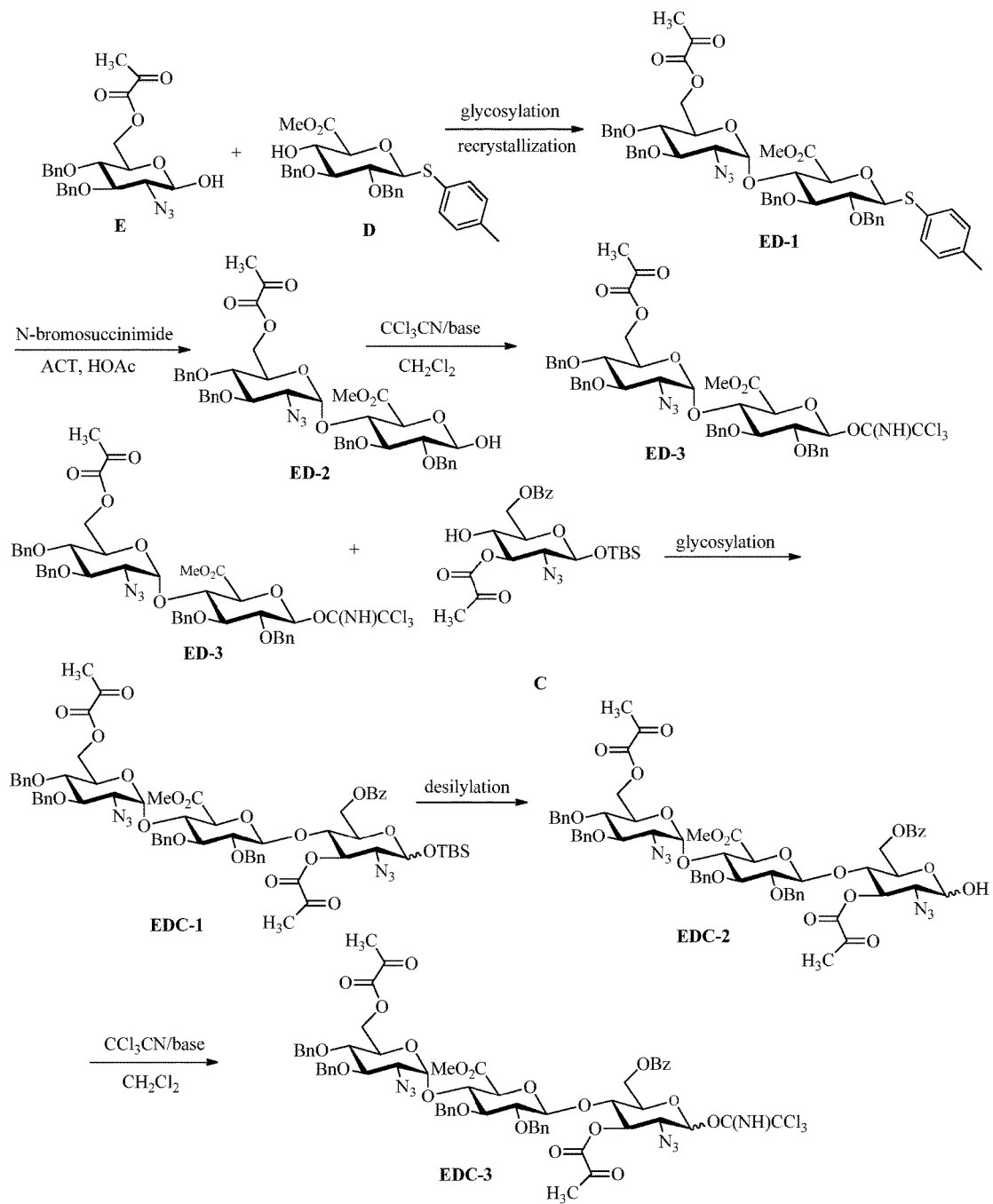
FIG. 11 illustrates one example of preparation of the trisaccharide of Formula V (Trisaccharide EDC).
Figure 12:
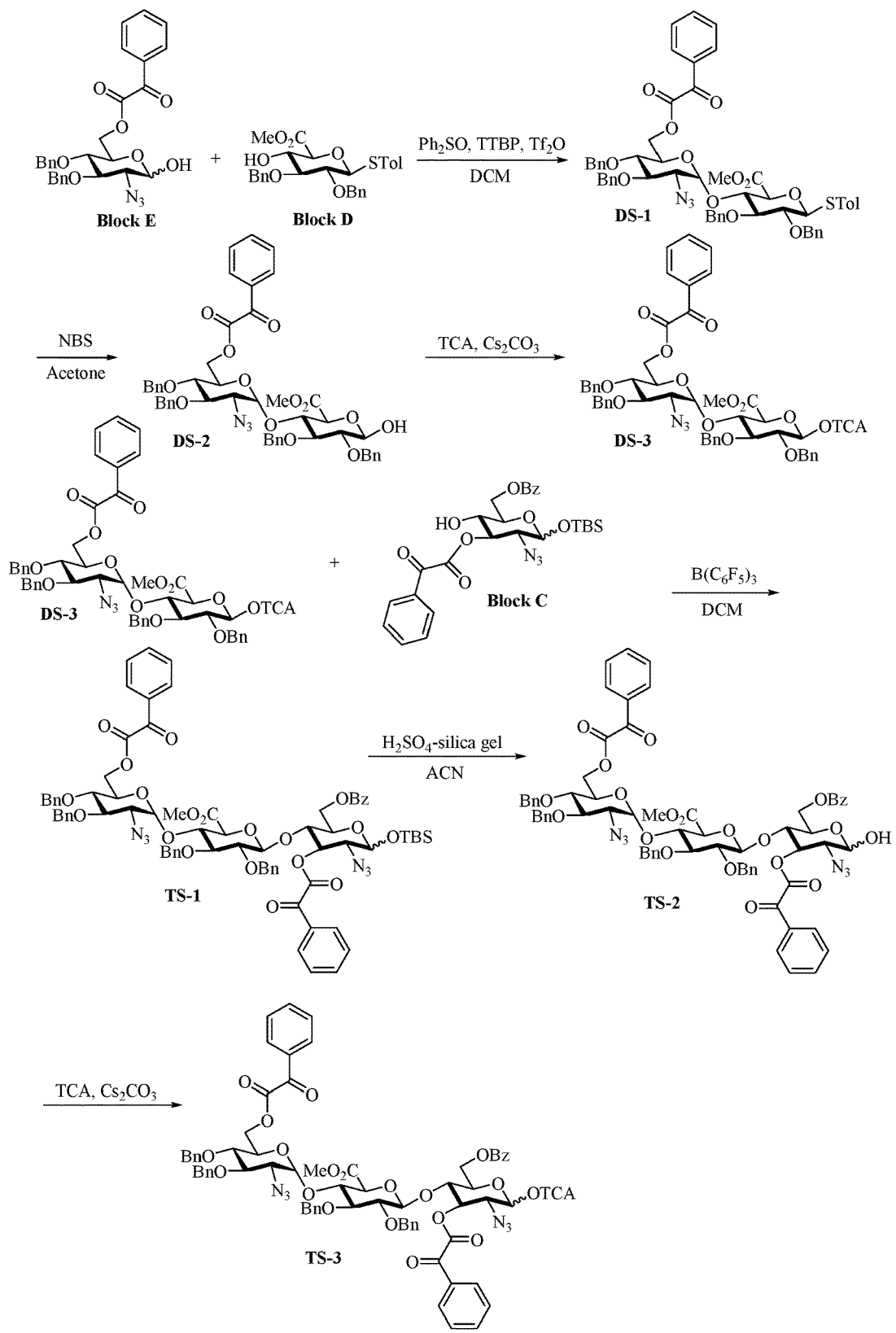
FIG. 12 illustrates another example of preparation of the trisaccharide of Formula V (Trisaccharide EDC).
Figure 13:
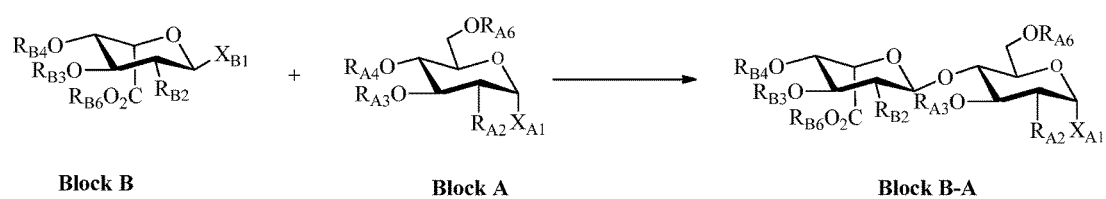
FIG. 13 illustrates the preparation of the disaccharide of Formula VI.
Figure 14:
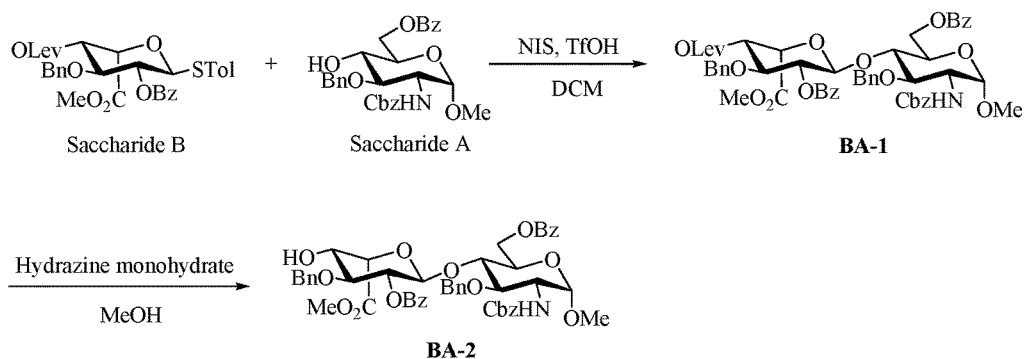
FIG. 14 illustrates one example of preparation of the disaccharide of Formula VI (Disaccharide BA-2).
Figure 15:
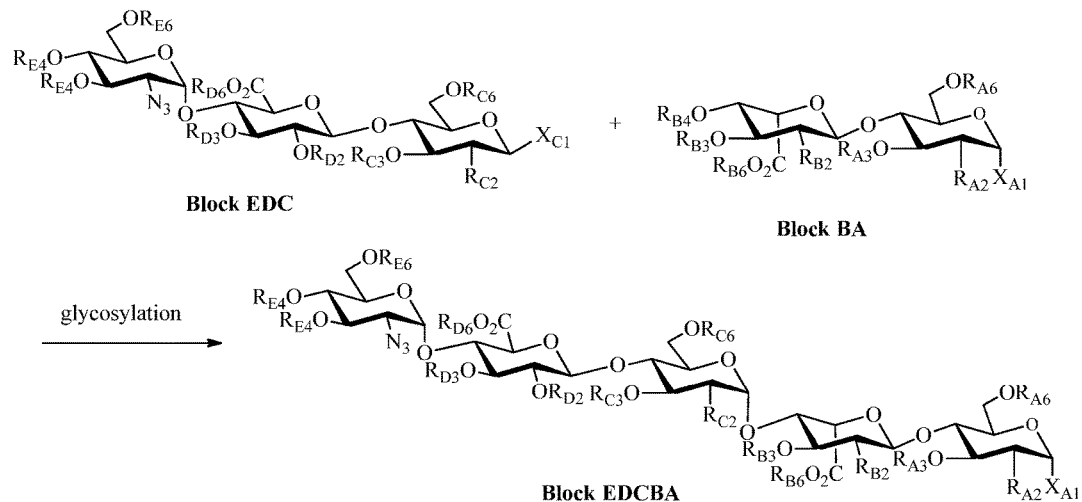
FIG. 15 illustrates the preparation of the pentasaccharide of Formula VII.
Figure 16:
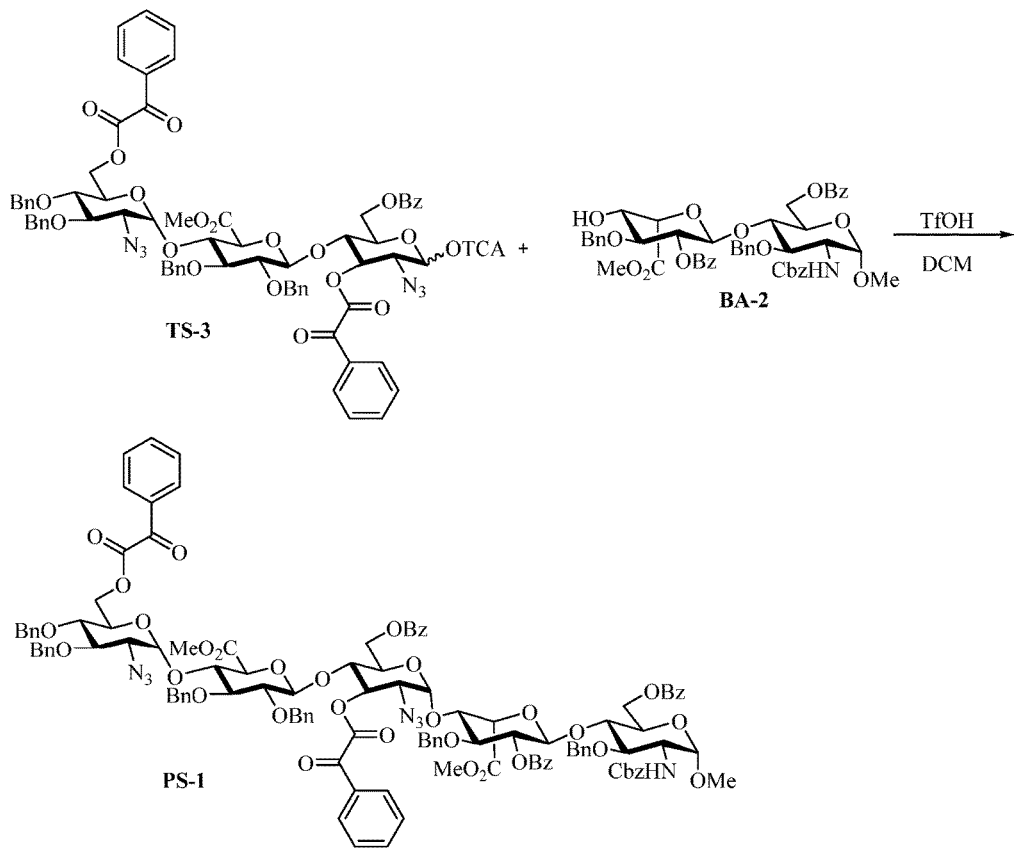
FIG. 16 illustrates the preparation of the pentasaccharide of Formula VII (Pentasaccharide-1).

As recited herein, all numbers should be considered modified by the term "about".

As used herein, "a," "an," "the," "at least one," and "one or more" are used interchangeably.

Also herein, the recitations of numerical ranges by endpoints include all numbers subsumed within that range (e.g., 1 to 5 includes 1, 1.5, 2, 2.75, 3, 3.80, 4, 5, etc.).

As used herein, "alkyl" is intended to include both branched and straight-chain saturated aliphatic hydrocarbon groups having one to ten carbon atoms unless otherwise specified. For example, Ci-Cio, as in "Ci-Cio alkyl" is defined to include groups having 1, 2, 3, 4, 5, 6, 7, 8, 9 or 10 carbons in a linear, branched, or cyclic arrangement. For example, "Ci-Cio alkyl" specifically includes methyl, ethyl, propyl, butyl, pentyl, hexyl, heptyl, octyl, nonyl, decyl, and so on.

As used herein, "aryl" is intended to mean any stable monocyclic or bicyclic carbon ring of up to 12 atoms in each ring, wherein at least one ring is aromatic. Examples of such aryl elements include phenyl, naphthyl, tetrahydronaphthyl, indanyl, biphenyl, phenanthryl, anthryl or acenaphthyl. In cases where the aryl substituent is bicyclic and one ring is non-aromatic, it is understood that attachment is via the aromatic ring.

The present invention provides method for preparing monosaccharides, disaccharides, trisaccharides, and pentasaccharides of heparinoids.

The present invention provides composition of matter of intermediates, and a process for the synthesis of pentasaccharides. What this entails is a stepwise synthetic process employing monosaccharides, disaccharides and trisaccharides.

The nature of AT-III binding pentasaccharide is such, that under cursory analysis of the individual monomeric units constituting the pentasaccharide, it is noted that each is distinct from the others. Secondly, it can be seen that there is an alternating stereospecificity in regard to the glycosidic Linkages (Structure 2).

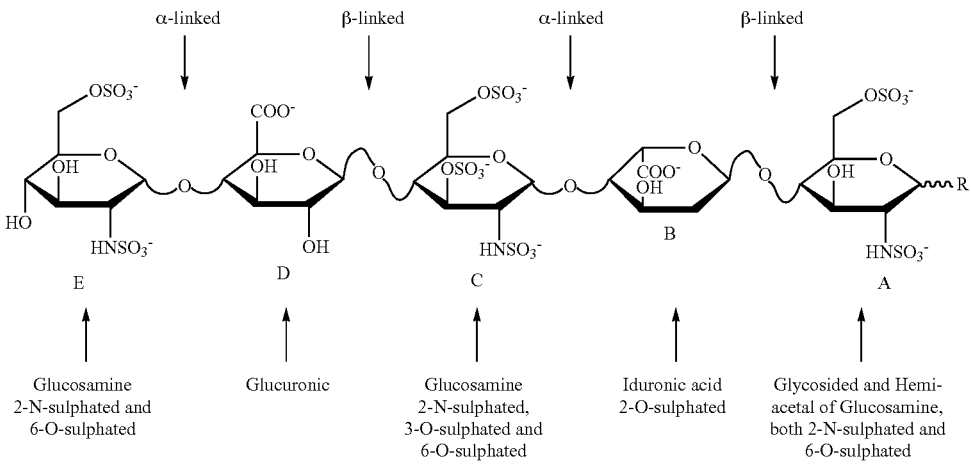

Structure 2

In a synthesis, the difference evident in each saccharide requires that each individual monomer used in the synthesis will need a different protecting group pattern. In light of this, it is essential in the synthesis of the above pentasaccharide that a protecting group strategy is carefully conceived. As can be seen, the pentasaccharide displays O-sulfation, N-sulfation, there are free hydroxyl groups, and there are stereospecific glycosidic linkages.

The pentasaccharide can be constructed in a variety of different ways; saccharides B and A can be coupled, saccharides E and D can be coupled, saccharide C can be coupled to either, and the resulting dimer and trimer can finally be coupled to form the pentasaccharide. Alternatively, each saccharide can be added sequentially and so on. There are a number of alternative coupling sequences that can be easily conceived and the choice made in regard to this, in itself, has a marked effect on the synthetic methodologies that will finally be employed, and therefore impacts on the overall success of the synthesis.

List of Abbreviations: Dde: 1-(4,4-dimethyl-2,6-dioxocyclohex-ylidene)ethyl, Bn: Benzyl, Bz: Benzoyl, DTPM: (1,3-dimethyl-2,4,6 (1H, 3H, 5H)-trioxopyrimidin-5-ylidene)methyl, Fmoc: fluorenylmethyloxycarbonyl chloride, Troc: trichloroethyl chloroformate, Boc: tert-butyloxycarbonyl In one aspect the invention provides a monosaccharide of Formula I,

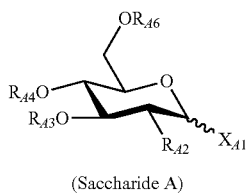

(Saccharide A)

wherein $X_{A1}$ is selected from hydroxy, alkoxy, aryloxy, benzyloxy, substituted benzyloxy; thioalkyl, thioaryl, halogen, trichloroacetimidoyl, phosphate and related phosphate ester leaving groups, or other suitable leaving groups; or a tert-butyldiphenylsilyloxy or other substituted siloxy protecting groups; and the stereochemistry may be alpha or beta; $R_{A2}$ is selected from an azido function, an amine; NH-Boc, NH-Cbz, NH-Dde, NH-DTPM, NH-Fmoc, NH-phthalimido, or NH-Troc; $R_{A3}$ comprises benzyl or substituted benzyl protecting group, allyl, or allyloxycarbonyl, or $R_{A2}$ and $R_{A3}$ can combine together to form a cyclic carbamate; $R_{A4}$ is selected from a H atom; a levulinoyl, chloroacetyl, 4-acetoxybenzoyl, 4-acetamidobenzoyl, 4-azidobenzoyl, or other substituted benzoyl type protecting group; a benzyl group, a 4-acetoxybenzyl, 4-acetamidobenzyl or other suitable substituted benzyl type protecting group, allyl ether, or carbonate type protecting groups; or $R_{A4}$ and $R_{A6}$ can combine to form a benzylidene or substituted benzylidene ring; and $R_{A6}$ is selected from alkyl 2-oxoacyl type protecting group or other substituted alkyl type protecting group, or aryl 2-oxoacyl type protecting group or other substituted aryl type protecting group.

In the preferred embodiment of the present invention, $R_{A6}$ is pyruvate.

In another preferred embodiment of the present invention, $R_{A6}$ is benzoyl.

In another preferred embodiment of the present invention, the monosaccharide of Formula I is

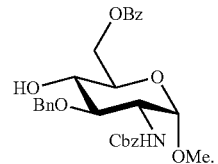

In a second aspect the invention provides a monosaccharide of Formula II,

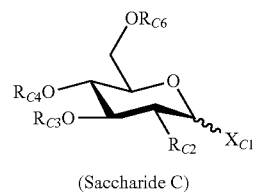

(Saccharide C)

wherein $X_{C1}$ is selected from a hydroxyl group; thioalkyl, thioaryl, halogen, trichloroacetimidoyl, phosphate and related phosphate ester leaving groups, or other suitable leaving groups; or a tert-butyldiphenylsilyloxy or other substituted silyloxy protecting groups; and the stereochemistry may be alpha or beta; $R_{C2}$ is selected from an azido function, an amine; NH-Dde or NH-DTPM group, or $R_{C2}$ and $R_{C3}$ can combine together to form a cyclic carbamate; $R_{C3}$ is selected from 4-methoxyphenyl; substituted benzyl groups; alkylacyl, arylacyl, alkylarylacyl, substituted alkylacyl, arylacyl or alkylarylacyl protecting groups; an azulen-1-yl-oxo-acetyl (Az) type protecting group or other substituted Az type protecting group, alkyl 2-oxoacyl type protecting group or other substituted alkyl type protecting group, aryl 2-oxoacyl type protecting group or other substituted aryl type protecting group; carbonate protecting groups; a tert-butyldiphenylsilyloxy or substituted siloxy protecting groups, allyl, methoxymethyl, methoxyethyl, or benzyloxymethyl; $R_{C4}$ is selected from a H atom; a levulinoyl, chloroacetyl, 4-acetoxybenzoyl, 4-acetamidobenzoyl, 4-azidobenzoyl, or other substituted benzoyl type protecting group; a benzyl group, a 4-acetoxybenzyl, 4-acetamidobenzyl or other suitable substituted benzyl type protecting group, an azulen-1-yl-oxo-acetyl (Az) type protecting group or other substituted Az type protecting group, alkyl 2-oxoacyl type protection group or other substituted alkyl type protecting group, aryl 2-oxoacyl type protecting group or other substituted aryl type protecting group, allyl ether, or carbonate type protecting groups; and $R_{C6}$ is selected from 4-methoxyphenyl; substituted benzyl groups; alkylacyl, arylacyl, alkylarylacyl, substituted alkylacyl, arylacyl or alkylarylacyl protecting groups; an azulen-1-yl-oxo-acetyl (Az) type protecting group or other substituted Az type protecting group, alkyl 2-oxoacyl type protecting group or other substituted alkyl type protecting group, aryl 2-oxoacyl type protecting group or other substituted aryl type protecting group; carbonate protecting groups; a tert-butyldiphenylsilyloxy or substituted siloxy protecting groups, allyl, methoxymethyl, methoxyethyl, or benzyloxymethyl, provided that at least one of $R_{C3}$ and $R_{C6}$ is alkyl 2-oxoacyl type protecting group or other substituted alkyl type protecting group, aryl 2-oxoacyl type protecting group or other substituted aryl type protecting group.

In the preferred embodiment of the present invention, $R_{C3}$ and $R_{C6}$ are pyruvate.

In another preferred embodiment of the present invention, $R_{C3}$ is substituted benzyl and $R_{C6}$ is benzoyl.

In another preferred embodiment of the present invention, the monosaccharide of Formula II is

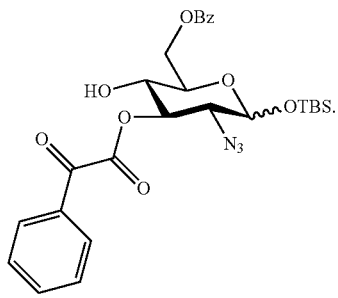

In a third aspect the invention provides a monosaccharide of Formula III,

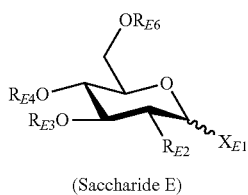

Formula III (Saccharide E)

wherein $X_{E1}$ is selected from a hydroxyl; thioalkyl, thioaryl, a tert-butyldiphenylsilyloxy or other substituted siloxy protecting groups; and the stereochemistry may be alpha or beta; $R_{E2}$ is selected from an azido function, an amine; NH-Dde or NH-DTPM group, or $R_{E2}$ and $R_{E3}$ can combine together to form a cyclic carbamate; $R_{E3}$ is selected from benzyl or substituted benzyl protecting group, allyl, or allyloxycarbonyl, or $R_{E2}$ and $R_{E3}$ can combine together to form a cyclic carbamate; $R_{E4}$ is selected from a benzyl, or substituted benzyl protecting group, allyl, or allyloxycarbonyl; and $R_{E6}$ is selected from alkyl 2-oxoacyl type protecting group or other substituted alkyl type protecting group, or aryl 2-oxoacyl type protecting group or other substituted aryl type protecting group.

In the preferred embodiment of the present invention, $R_{E6}$ is pyruvate.

In another preferred embodiment of the present invention, $R_{E6}$ is substituted benzyl.

In another preferred embodiment of the present invention, the monosaccharide of Formula III is

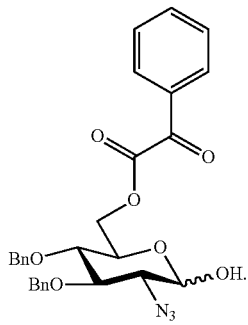

In a fourth aspect the invention provides a monosaccharide of Formula IV,

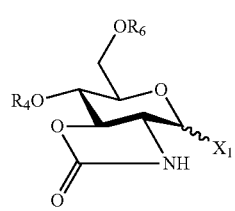

Formula IV (Cyclic carbamate for Saccharides A, C or E)

wherein $X_1$ is selected from hydroxy, alkoxy, aryloxy, benzyloxy, substituted benzyloxy; thioalkyl, thioaryl, halogen, trichloroacetimidoyl, phosphate and related phosphate ester leaving groups, or other suitable leaving groups; a tert-butyldiphenylsilyloxy or other substituted siloxy protecting group; and the stereochemistry may be alpha or beta; $R_4$ is selected from a hydrogen atom; a levulinoyl, chloroacetyl, 4-acetoxybenzoyl, 4-acetamidobenzoyl, 4-azidobenzoyl, or other substituted benzoyl type protecting group; a benzyl group, a 4-acetoxybenzyl, 4-acetamidobenzyl or other suitable substituted benzyl type protecting group, an azulen-1-yl-oxo-acetyl (Az) type protecting group or other substituted Az type protecting group, alkyl 2-oxoacyl type protecting group or other substituted alkyl type protecting group, aryl 2-oxoacyl type protecting group or other substituted aryl type protecting group, allyl ether, or carbonate type protecting groups; and $R_6$ is selected from alkyl 2-oxoacyl type protecting group or other substituted alkyl type protecting group, or aryl 2-oxoacyl type protecting group or other substituted aryl type protecting group.

In the preferred embodiment of the present invention, $R_6$ is pyruvate.

In a fifth aspect the invention provides a trisaccharide of Formula V,

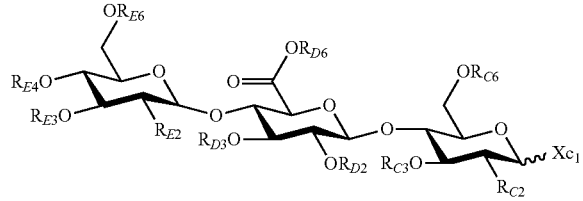

Formula V (Saccharide EDC)

wherein $X_{C1}$ is selected from a hydroxyl group; thioalkyl, thioaryl, halogen, trichloroacetimidoyl, phosphate and related phosphate ester leaving groups, or other suitable leaving groups; or a tert-butyldiphenylsilyloxy or other substituted silyloxy protecting groups; and the stereochemistry may be alpha or beta; $R_{C2}$ is selected from an azido function, an amine; NH-Dde or NH-DTPM group, or $R_{C2}$ and $R_{C3}$ can combine together to form a cyclic carbamate; $R_{C3}$ is selected from 4-methoxyphenyl; substituted benzoyl groups; alkylacyl, arylacyl, alkylarylacyl, substituted alkylacyl, arylacyl or alkylarylacyl protecting groups; an azulen-1-yl-oxo-acetyl (Az) type protecting group or other substituted Az type protecting group, alkyl 2-oxoacyl type protecting group or other substituted alkyl type protecting group, aryl 2-oxoacyl type protecting group or other substituted aryl type protecting group; carbonate protecting groups; a tert-butyldiphenylsilyloxy or substituted siloxy protecting groups, allyl, methoxymethyl, methoxyethyl, or benzyloxymethyl; $R_{C6}$ is selected from 4-methoxyphenyl;

substituted benzyl groups; alkylacyl, arylacyl, alkylarylacyl, substituted alkylacyl, arylacyl or alkylarylacyl protecting groups; an azulen-1-yl-oxo-acetyl (Az) type protecting group or other substituted Az type protecting group, alkyl 2-oxoacyl type protecting group or other substituted alkyl type protecting group, aryl 2-oxoacyl type protecting group or other substituted aryl type protecting group; carbonate protecting groups; a tert-butyldiphenylsilyloxy or substituted siloxy protecting groups, allyl, methoxymethyl, methoxyethyl, or benzyloxymethyl; $R_{D2}$ is selected from 4-methoxyphenyl; benzyl, substituted benzyl groups; alkylacyl, arylacyl and alkylarylacyl, or substituted alkylacyl, arylacyl and alkylarylacyl protecting groups; carbonate protecting groups, silyl protecting groups, carbamate protecting groups, $C_3$-$C_5$ alkenyl; $R_{D3}$ is selected from 4-methoxyphenyl; benzyl, substituted benzyl groups; alkylacyl, arylacyl and alkylarylacyl, or substituted alkylacyl, arylacyl and alkylarylacyl protecting groups; carbonate protecting groups; $R_{D6}$ is selected from methyl, $C_2$-$C_5$ alkyl; substituted alkyl, $C_3$-$C_5$ alkenyl; or, benzyl and substituted benzyl groups; $R_{E2}$ is selected from an azido function, an amine; NH-Dde or NH-DTPM group, or $R_{E2}$ and $R_{E3}$ can combine together to form a cyclic carbamate; $R_{E3}$ is selected from benzyl or substituted benzyl protecting group, allyl, or allyloxycarbonyl, or $R_{E2}$ and $R_{E3}$ can combine together to form a cyclic carbamate; $R_{E4}$ is selected from a benzyl, or substituted benzyl protecting group, allyl, or allyloxycarbonyl; and $R_{E6}$ is selected from 4-methoxyphenyl; substituted benzoyl groups; alkylacyl, arylacyl, alkylarylacyl, substituted alkylacyl, arylacyl or alkylarylacyl protecting groups; an azulen-1-yl-oxo-acetyl (Az) type protecting group or other substituted Az type protecting group, alkyl 2-oxoacyl type protecting group or other substituted alkyl type protecting group, aryl 2-oxoacyl type protecting group or other substituted aryl type protecting group; carbonate protecting groups; a tert-butyldiphenylsilyloxy or substituted siloxy protecting groups, allyl, methoxymethyl, methoxyethyl, or benzyloxymethyl, provided that at least one of $R_{C3}$, $R_{C6}$ and $R_{E6}$ is alkyl 2-oxoacyl type protecting group or other substituted alkyl type protecting group, aryl 2-oxoacyl type protecting group or other substituted aryl type protecting group.

In the preferred embodiment of the present invention, $R_{C3}$, $R_{C6}$ and $R_{E6}$ are pyruvate.

In another preferred embodiment of the present invention, $R_{C3}$ is substituted benzyl, $R_{C6}$ is benzoyl, and $R_{E6}$ is substituted benzyl.

In a sixth aspect the invention provides a disaccharide of Formula VI,

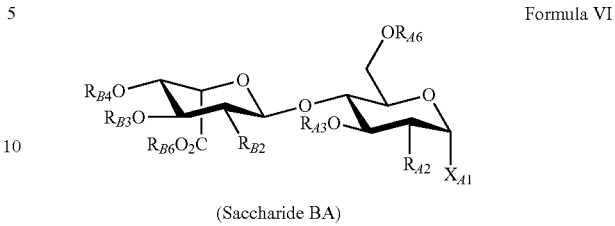

(Saccharide BA)

wherein $X_{A1}$ is selected from hydroxy, alkoxy, aryloxy, benzyloxy, substituted benzyloxy; thioalkyl, thioaryl, halogen, trichloroacetimidoyl, phosphate and related phosphate ester leaving groups, or other suitable leaving groups; or a tert-butyldiphenylsilyloxy or other substituted siloxy protecting groups; and the stereochemistry may be alpha or beta; $R_{A2}$ is selected from an azido function, an amine; NH-Boc, NH-Cbz, NH-Dde, NH-DTPM, NH-Fmoc, NH-phthalimido, or NH-Troc; $R_{A3}$ comprises benzyl or substituted benzyl protecting group, allyl, or allyloxycarbonyl, or $R_{A2}$ and $R_{A3}$ can combine together to form a cyclic carbamate; $R_{A6}$ is selected from alkyl 2-oxoacyl type protecting group or other substituted alkyl type protecting group, or aryl 2-oxoacyl type protecting group or other substituted aryl type protecting group; $R_{B2}$ is selected from 4-methoxyphenyl; substituted benzyl groups; alkylacyl, arylacyl or alkylarylacyl, and substituted alkylacyl, arylacyl or alkylarylacyl protecting groups; carbonate protecting groups; a tert-butyldiphenylsilyloxy or other such substituted silyloxy protecting group allyl, methoxymethyl, methoxyethyl, benzyloxymethyl; $R_{B3}$ is selected from benzyl or substituted benzyl protecting group, allyl, allyloxycarbonyl; $R_{B4}$ is H; and $R_{B6}$ is selected from methyl, C2-C5 alkyl; substituted alkyl, C3-C5 alkenyl; or, benzyl and substituted benzyl groups.

In the preferred embodiment of the present invention, $R_{A6}$ is pyruvate.

In another preferred embodiment of the present invention, $R_{A6}$ is benzoyl.

In a seventh aspect the invention provides a pentasaccharide of Formula VII,

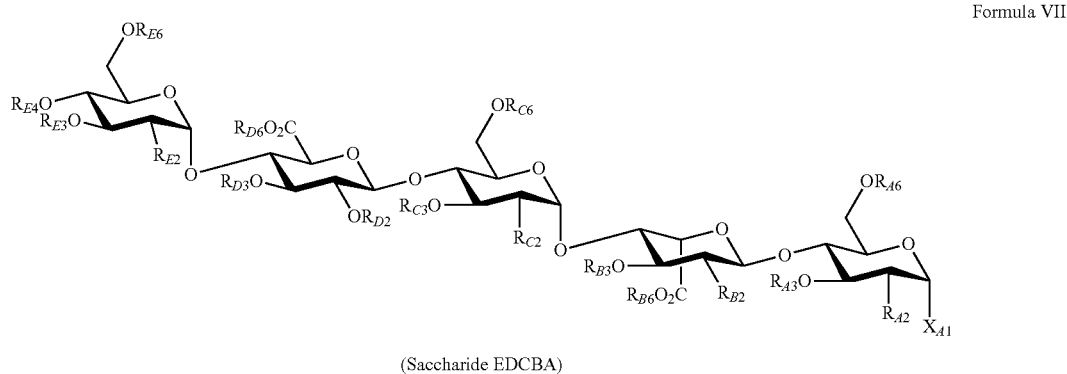

(Saccharide EDCBA)

wherein $X_{A1}$ is selected from hydroxy, alkoxy, aryloxy, benzyloxy, substituted benzyloxy; thioalkyl, thioaryl, halogen, trichloroacetimidoyl, phosphate and related phosphate ester leaving groups, or other suitable leaving groups; or a tert-butyldiphenylsilyloxy or other substituted siloxy protecting groups; and the stereochemistry may be alpha or beta; $R_{A2}$ is selected from an azido function, an amine; NH-Boc, NH-Cbz, NH-Dde, NH-DTPM, NH-Fmoc, NH-phthalimido, or NH-Troc; $R_{A3}$ comprises benzyl or substituted benzyl protecting group, allyl, or allyloxycarbonyl, or $R_{A2}$ and $R_{A3}$ can combine together to form a cyclic carbamate; $R_{A6}$ is selected from 4-methoxyphenyl; substituted benzyl groups; alkylacyl, arylacyl, alkylarylacyl, substituted alkylacyl, arylacyl or alkylarylacyl protecting groups; an azulen-1-yl-oxo-acetyl (Az) type protecting group or other substituted Az type protecting group, alkyl 2-oxoacyl type protecting group or other substituted alkyl type protecting group, aryl 2-oxoacyl type protecting group or other substituted aryl type protecting group; carbonate protecting groups; a tert-butyldiphenylsilyloxy or substituted siloxy protecting groups, allyl, methoxymethyl, methoxyethyl, or benzyloxymethyl; $R_{B2}$ is selected from 4-methoxyphenyl; substituted benzyl groups; alkylacyl, arylacyl or alkylarylacyl, and substituted alkylacyl, arylacyl or alkylarylacyl protecting groups; carbonate protecting groups; a tert-butyldiphenylsilyloxy or other such substituted silyloxy protecting group allyl, methoxymethyl, methoxyethyl, benzyloxymethyl; $R_{B3}$ is selected from benzyl or substituted benzyl protecting group, allyl, allyloxycarbonyl; $R_{B6}$ is selected from methyl, C2-C5 alkyl; substituted alkyl, C3-C5 alkenyl; or, benzyl and substituted benzyl groups; $R_2$ is selected from an azido function, an amine; NH-Dde or NH-DTPM group, or $R_{C2}$ and $R_{C3}$ can combine together to form a cyclic carbamate; $R_{C3}$ is selected from 4-methoxyphenyl; substituted benzyl groups; alkylacyl, arylacyl, alkylarylacyl, substituted alkylacyl, arylacyl or alkylarylacyl protecting groups; an azulen-1-yl-oxo-acetyl (Az) type protecting group or other substituted Az type protecting group, alkyl 2-oxoacyl type protecting group or other substituted alkyl type protecting group, aryl 2-oxoacyl type protecting group or other substituted aryl type protecting group; carbonate protecting groups; a tert-butyldiphenylsilyloxy or substituted siloxy protecting groups, allyl, methoxymethyl, methoxyethyl, or benzyloxymethyl; $R_6$ is selected from 4-methoxyphenyl; substituted benzyl groups; alkylacyl, arylacyl, alkylarylacyl, substituted alkylacyl, arylacyl or alkylarylacyl protecting groups; an azulen-1-yl-oxo-acetyl (Az) type protecting group or other substituted Az type protecting group, alkyl 2-oxoacyl type protecting group or other substituted alkyl type protecting group, aryl 2-oxoacyl type protecting group or other substituted aryl type protecting group; carbonate protecting groups; a tert-butyldiphenylsilyloxy or substituted siloxy protecting groups, allyl, methoxymethyl, methoxyethyl, or benzyloxymethyl; $R_{D2}$ is selected from 4-methoxyphenyl; benzyl, substituted benzyl groups; alkylacyl, arylacyl and alkylarylacyl, or substituted alkylacyl, arylacyl and alkylarylacyl protecting groups; carbonate protecting groups, silyl protecting groups, carbamate protecting groups, $C_3$-$C_5$ alkenyl; $R_{D3}$ is selected from 4-methoxyphenyl; benzyl, substituted benzyl groups; alkylacyl, arylacyl and alkylarylacyl, or substituted alkylacyl, arylacyl and alkylarylacyl protecting groups; carbonate protecting groups; $R_{D6}$ is selected from methyl, $C_2$-$C_5$ alkyl; substituted alkyl, $C_3$-$C_5$ alkenyl; or, benzyl and substituted benzyl groups; $R_{E2}$ is selected from an azido function, an amine; NH-Dde or NH-DTPM group, or $R_{E2}$ and $R_{E3}$ can combine together to form a cyclic carbamate; $R_{E3}$ is selected from benzyl or substituted benzyl protecting group, allyl, or allyloxycarbonyl, or $R_{E2}$ and $R_{E3}$ can combine together to form a cyclic carbamate; $R_{E4}$ is selected from a benzyl, or substituted benzyl protecting group, allyl, or allyloxycarbonyl; and $R_{E6}$ is selected from 4-methoxyphenyl; substituted benzyl groups; alkylacyl, arylacyl, alkylarylacyl, substituted alkylacyl, arylacyl or alkylarylacyl protecting groups; an azulen-1-yl-oxo-acetyl (Az) type protecting group or other substituted Az type protecting group, alkyl 2-oxoacyl type protecting group or other substituted alkyl type protecting group, aryl 2-oxoacyl type protecting group or other substituted aryl type protecting group; carbonate protecting groups; a tert-butyldiphenylsilyloxy or substituted siloxy protecting groups, allyl, methoxymethyl, methoxyethyl, or benzyloxymethyl, provided that at least one of $R_{A6}$, $R_{C3}$, $R_{C6}$ and $R_{E6}$ is alkyl 2-oxoacyl type protecting group or other substituted alkyl type protecting group, aryl 2-oxoacyl type protecting group or other substituted aryl type protecting group.

In the preferred embodiment of the present invention, $R_{A6}$, $R_{C3}$ $R_{C6}$ and $R_{E6}$ are pyruvate.

In another preferred embodiment of the present invention, $R_{A6}$ is benzoyl, $R_{C3}$ is substituted benzyl, $R_{C6}$ is benzoyl, and $R_{E6}$ is substituted benzyl.

The present invention provides a method for preparing a trisaccharide of Formula EDC-1, comprising steps of:

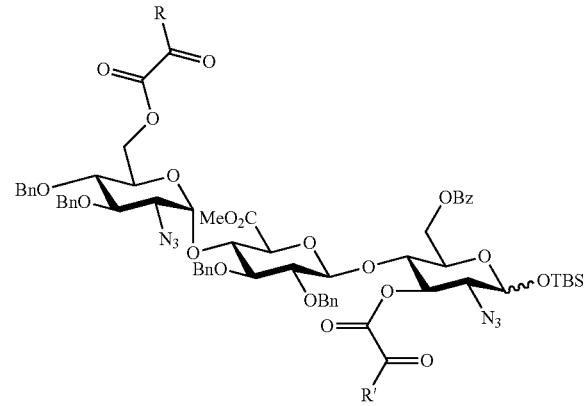

Formula EDC-1 glycosylation of a disaccharide of Formula ED-3

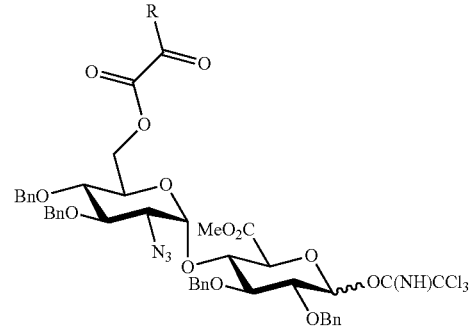

Formula ED-3 with a monosaccharide of Formula C in the presence of boron compound (catalyst),

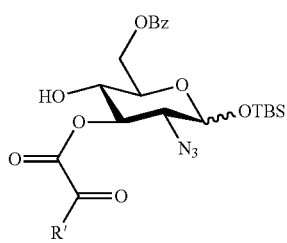

Formula C wherein R is selected from alkyl, substituted alkyl, aryl, or substituted aryl group, R' is selected from alkyl, substituted alkyl, aryl, or substituted aryl group, Bn is benzyl group, Bz is benzoyl group, and TBS is tert-butyldimethylsilyl group. The boron compound is selected from boron trifluoride diethyl etherate or tris(pentafluorophenyl)borane. In a preferred embodiment, the boron compound tris(pentafluorophenyl)borane. In another preferred embodiment, R is phenyl group and R' is phenyl group. The trisaccharide of Formula EDC-1 is in beta position with at least 60% stereoselectivity. In a preferred embodiment, the trisaccharide of Formula EDC-1 is in beta position with at least 70% stereoselectivity. In another preferred embodiment, the trisaccharide of Formula EDC-1 is in beta position with at least 80% stereoselectivity.

The present invention provides a method for preparing a disaccharide of Formula ED-3, comprising steps of

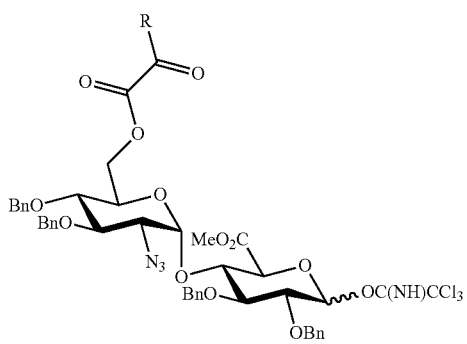

Formula ED-3 reacting a disaccharide of Formula ED-2

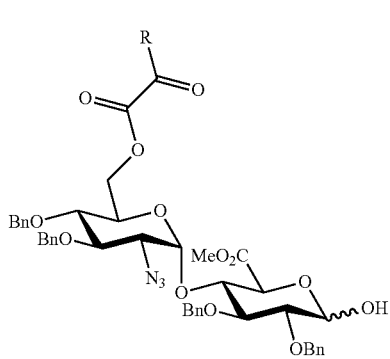

Formula ED-2 with 2,2,2-trichloroacetonitrile (TCA) and inorganic base, wherein R is selected from alkyl, aryl, or substituted aryl group, and Bn is benzyl group. The inorganic base is selected from potassium carbonate or cesium carbonate. The 2,2,2-trichloroacetonitrile is further recycled by distillation. In a preferred embodiment, R is phenyl group.

The present invention further provides a method for preparing a trisaccharide of Formula EDC-2, comprising steps of:

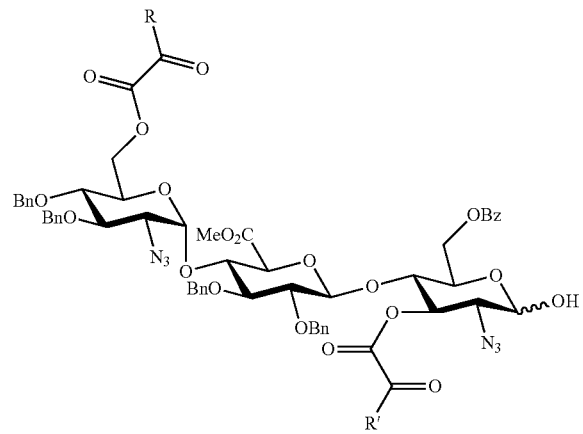

Formula EDC-2 desilylation of a trisaccharide of Formula EDC-1 using silica gel in the presence of strong acids, and the silica gel is filtrated to obtain the trisaccharide of Formula EDC-2 in solid form, wherein R is selected from alkyl, substituted alkyl, aryl, or substituted aryl group, R' is selected from alkyl, substituted alkyl, aryl, or substituted aryl group, Bn is benzyl group, and Bz is benzoyl group. In a preferred embodiment, R is phenyl group. In another preferred embodiment, the strong acids is selected from $H_2SO_4$, $CH_3SO_3H$, or $CF_3SO_3H$.

In conventional desilylation reaction, especially for bulky protecting group, tert-butyldimethylsilyl group (TBDMS or TBS group), tetrabutylammonium fluoride (TBAF) was used to remove TBS protecting group, and then separated and purified with silica gel column. This reaction requires large amount of organic solvent and time to concentrate to obtain the product. It is also not easy to remove TBAF effectively in the resultant compounds so that the purified product is difficult to store because of degradation and deterioration. However, the method for preparing a trisaccharide of Formula EDC-2 of the present invention is carried out by using silica gel in the presence of strong acids and stirred evenly in organic solution for desilylation. After reaction completed, the silica gel is filtrated to obtain the trisaccharide of Formula EDC-2 in solid form and is further concentrated to obtain the product, trisaccharide of Formula EDC-2. The operation of the method of the present invention is simple and fast.

The present invention provides a method of preparing a trisaccharide of Formula EDC-3, comprising steps of:

Formula EDC-3

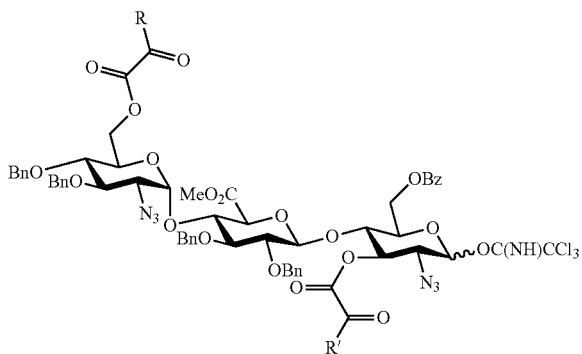

reacting a trisaccharide of Formula EDC-1 with 2,2,2-trichloroacetonitrile and and inorganic base, wherein R is selected from alkyl, substituted alkyl, aryl, or substituted aryl group, R' is selected from alkyl, substituted alkyl, aryl, or substituted aryl group, Bn is benzyl group, and Bz is benzoyl group. The inorganic base is selected from potassium carbonate or cesium carbonate. The 2,2,2-trichloroacetonitrile is further recycled by distillation. In a preferred embodiment, R is phenyl group.

Imidate formation of the conventional method carried out with organic base, 1,8-Diazabicyclo[5,4,0]undec-7-ene (DBU), and trichloroacetonitrile (TCA) as limiting reagent in an organic solvent to obtain imidate. The resultant compound was separated and purified with silica gel column. This reaction requires large amount of organic solvent and time to concentrate to obtain the product. However, the inorganic base (potassium carbonate or cesium carbonate) and TCA are used in the method of preparing a trisaccharide of Formula ED-3 and the method of preparing a trisaccharide of Formula EDC-3 of the present invention to form imidate. After the reaction completed, the TCA is further recycled by distillation without purification by silica gel column. The reaction time is reduced and the amount of chemical wastes is also reduced.

The trisaccharide of Formula EDC-3 is glycosylated with the disaccharide of Formula BA-2 to obtain the pentasaccharide and then to form Fondaparinux sodium. The overall process from monosaccharides to disaccharides, trisaccharides, and pentasaccharides are illustrated in FIGS. 1 to 17. The present invention provide the monosaccharides, disaccharides, trisaccharides and pentasaccharides for use in the preparation of heparinoids and provides method or process for preparation of monosaccharides, disaccharides, trisaccharides, and pentasaccharides of heparinoids in FIGS. 1 to 17.

The differences between the present invention and the prior arts are described below.

U.S. Pat. No. 7,541,445 claims a pentasaccharide building block for the preparation of synthetic heparinoids, said building block being of General Formula I. In which the configuration of the monosaccharidic units and the stereochemistry of the internal linkages is defined as D-gluco-alpha-1,4-D-glucurono-beta-1,4-D-Gluco-alpha-1,4-L-idurono-alpha-1,4-D-gluco, and the substituents are defined as; $X_1$ is selected from the group consisting of hydroxy, $C_2$ to $C_{10}$; alkoxy; aryloxy, thioalkyl, thioaryl, imidoyl, tbutyldiphenylsilyloxy; a lipoamino acid or other such group suitable for conjugation to delivery systems or solid supports; and the stereochemistry may be alpha or beta; or an alpha methoxy group; $R_H$, $R_{H1}$ and $R_{H2}$ are benzyl; $R_A$ is selected from the group consisting of an azido function, an NH-Dde, and NH-DTPM; $R_{S1}$, $R_{S2}$ and $R_{S5}$ are independently selected from the group consisting of alkylacyl and arylacyl; $R_{S3}$ is selected from the group consisting of 4-methoxyphenyl and 4-methoxybenzyl; $R_{S4}$ is selected from the group consisting of 4-methoxyphenyl and 4-methoxybenzyl; $R_{E1}$ is methyl; $R_{E2}$ is methyl; $R_B$ is selected from the group consisting of an azido function, an NH-Dde and an NH-DTPM group; $R_{B1}$ is selected from the group consisting of an azido function, an NH-Dde and an NH-DTPM group; $R_{P1}$ is benzyl; and $R_{P2}$ is benzyl.

U.S. Pat. No. 8,114,970 claims a monosaccharide of General Formula X, XIII, XVI, and a pentasaccharide building block for the preparation of synthetic heparinoids, said of being General Formula I, wherein $R_{p2}$ is selected from benzyl, chloroacetyl, acetyl, benzoyl, substituted benzoyl, pivaloyl, levulinyl or allyloxycarbonyl.

The method of the present invention is starting from trisaccharide TS-1 and disaccharide BA-2, NH-Cbz group of building block A of pentasaccharide, PS-1, protecting group of building block C, E which are different from U.S. Pat. No. 7,541,445, and U.S. Pat. No. 8,114,970 which discloses a pentasaccharide building block for preparation of synthetic heparinoids, said of being General Formula I.

U.S. Pat. No. 8,686,131 claims a trisaccharide building block of General Formula XXIII (E-D-C), a trisaccharide building block of General Formula XXIV (C-B-A), a trisaccharide building block of General Formula XXXII (E-D-C), a trisaccharide building block of General Formula XXXIII (E-D-C), a trisaccharide building block of General Formula XXXIV (E-D-C), a trisaccharide building block of General Formula XXXV (E-D-C).

U.S. Pat. No. 8,404,833 claims a disaccharide building block of General Formula XX (E-D), wherein: $X_2$ is selected from the group consisting of a hydroxyl group; thioalkyl, thioaryl, halogen, trichloroacetimidoyl, and a 'butyldiphenylsilyloxy, and wherein the stereochemistry may be alpha or beta; $R_{P1}$ is selected from the group consisting of 4-methoxyphenyl, benzyl, substituted benzyl groups, alkylacyl, arylacyl and alkylarylacyl, or substituted alkylacyl, arylacyl and alkylarylacyl protecting groups, and carbonate protecting groups; $R_{P2}$ is selected from the group consisting of 4-methoxyphenyl, alkylacyl, arylacyl and alkylarylacyl, or substituted alkylacyl, arylacyl and alkylarylacyl protecting groups, carbonate protecting groups, carbamate protecting groups, and $C_3$-$C_5$ alkenyl; $R_{E1}$ is selected from the group consisting of methyl, $C_2$-$C_5$ alkyl, substituted $C_2$-$C_5$ alkyl, $C_3$-$C_5$ alkenyl, benzyl and substituted benzyl groups; $R_{B1}$ is selected from the group consisting of an azido function, an amine, an NH-Dde and an NH-DTPM group, or $R_{H2}$ and $R_{B1}$ can combine together to form a cyclic carbamate; $R_H$ is benzyl; $R_{H2}$ is selected from the group consisting of benzyl, substituted benzyl protecting group, allyl, and allyloxycarbonyl, or $R_{H2}$ and $R_{B1}$ independently can combine together to form a cyclic carbamate; and $R_{S5}$ is selected from the group consisting of benzoyl, arylacyl or alkylarylacyl, and substituted alkylacyl, 4-chlorobenzoyl, arylacyl or alkylarylacyl protecting groups, allyloxycarbonyl, ethoxycarbonyl, tertbutoxycarbonyl, carbonate protecting groups, a 'butyldiphenylsilyl, allyl, methoxymethyl, methoxyethyl, and benzyloxymethyl.

The above mentioned building blocks in U.S. Pat. No. 8,686,131 and U.S. Pat. No. 8,404,833 were not involved in the method of the present invention.

EXAMPLE

The examples below are non-limited and are merely representative of various aspects and features of the present invention.

Example 1: Preparation of Monosaccharide E

Step 1. Formation of Monosaccharide E-4

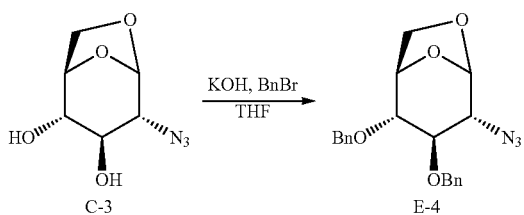

Tetrahydrofuran (THF)(550 ml), E-3 (C-3) were added to the reaction flask. Potassium hydroxide, benzyl bromide (BnBr) were added and stirred, heated to 65° C. for reflux. The white powder formed during reaction occurred. The reaction mixture was kept stirring under reflux until completion checked by TLC and UPLC. Sodium thiosulfate(sat) aqueous solution (30 ml), water (200 ml and Ethylacetate (200 ml) were added to the solution and stirred for 20 min, then stand for 20 min. the solution was separation into two layers. Collect the ethylacetate layer. Add water (250 ml) to ethylacetate layer and stirred for 20 min. discard the aqueous layer, then aqueous sodium chloride(sat) (200 ml) solution was added for extraction. Discard the aqueous layer, then extracted with aqueous sodium chloride(sat) (200 ml) solution. Collect all ethylacetate solutions and added MgSO$_4$ (28 g) for 30 min to absorb water. Filtered the solution, then the filtrate was concentrated under vacuum (15 torr) at 40° C. Crude E-4 (130 g) was achieved.

Step 2. Formation of Monosaccharide E-5

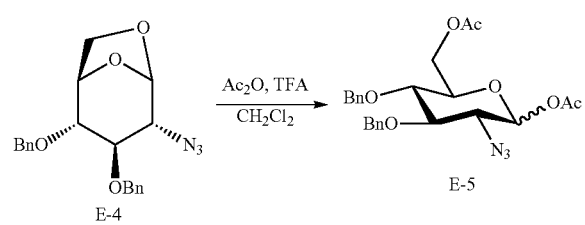

Acetic anhydride (Ac$_2$O) (1000 ml) was added to the reaction flask containing E-4 (130 g), then trifluoroacetic acid (TFA) was added and stirred. The reaction mixture was heated to 55~60° C. and stirred for 3 hr, and then check the reaction extent by TLC (EA/hexane=1/4) and UPLC. When the reactant, E-4 was disappeared on TLC plate, the solution was evaporated at 40° C. under vacuum (15 torr) to get rid of Ac$_2$O and TFA. Toluene (400 ml) and water (200 ml) were added to the solution. The pH of solution was adjusted to almost 7 with 45% NaOH aqueous solution, and stir for 15 min, then stand for 20 min. Discard the aqueous layer. Toluene (400 ml) and aqueous sodium bicarbonate solution (200 ml) were added to the solution and stirred for 15 min, then stand for 20 min. Discard the aqueous solution. MgSO$_4$ (28 g) was added to the toluene layer for 30 min to absorb water. Filtered the solution, then the filtrate was concentrated under vacuum (15 torr) at 40° C. Crude E-5 (150 g) was obtained.

Step 3. Formation of Monosaccharide E-6

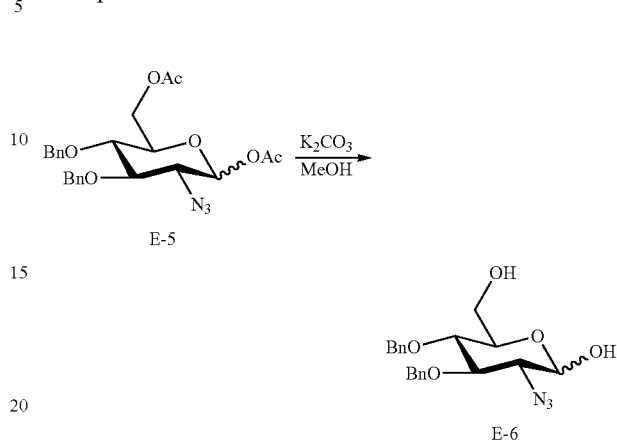

Figure 18:
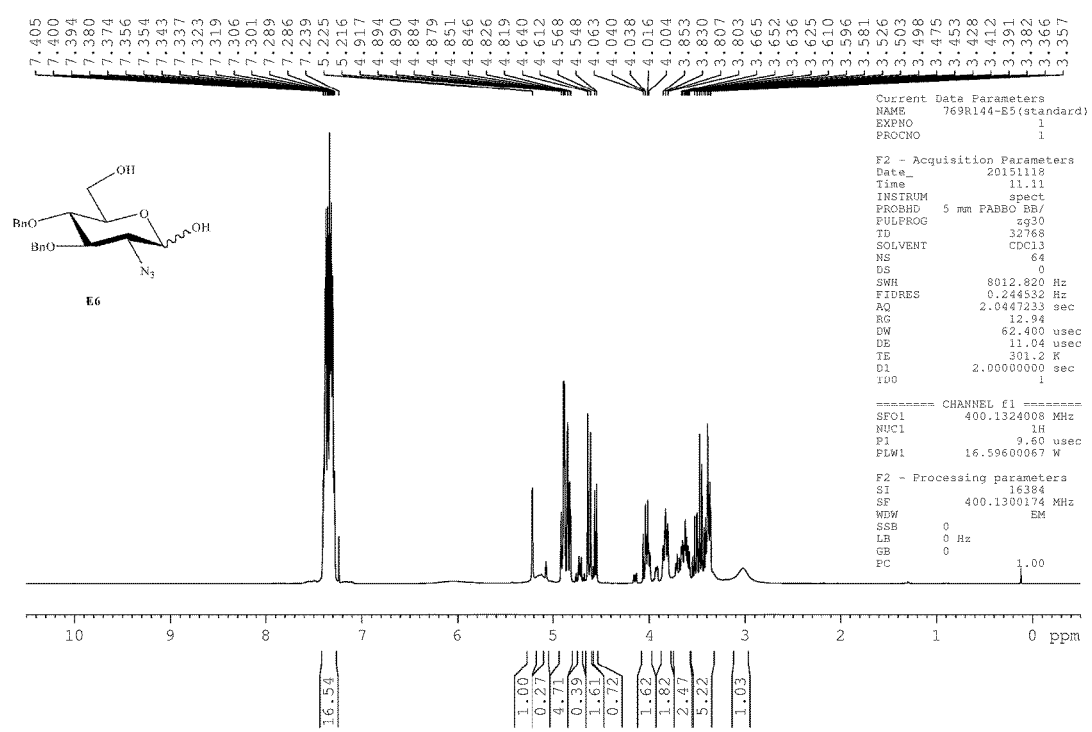
FIG. 18 is a $^1$H-NMR spectrum of Monosaccharide E-6.
Figure 19:
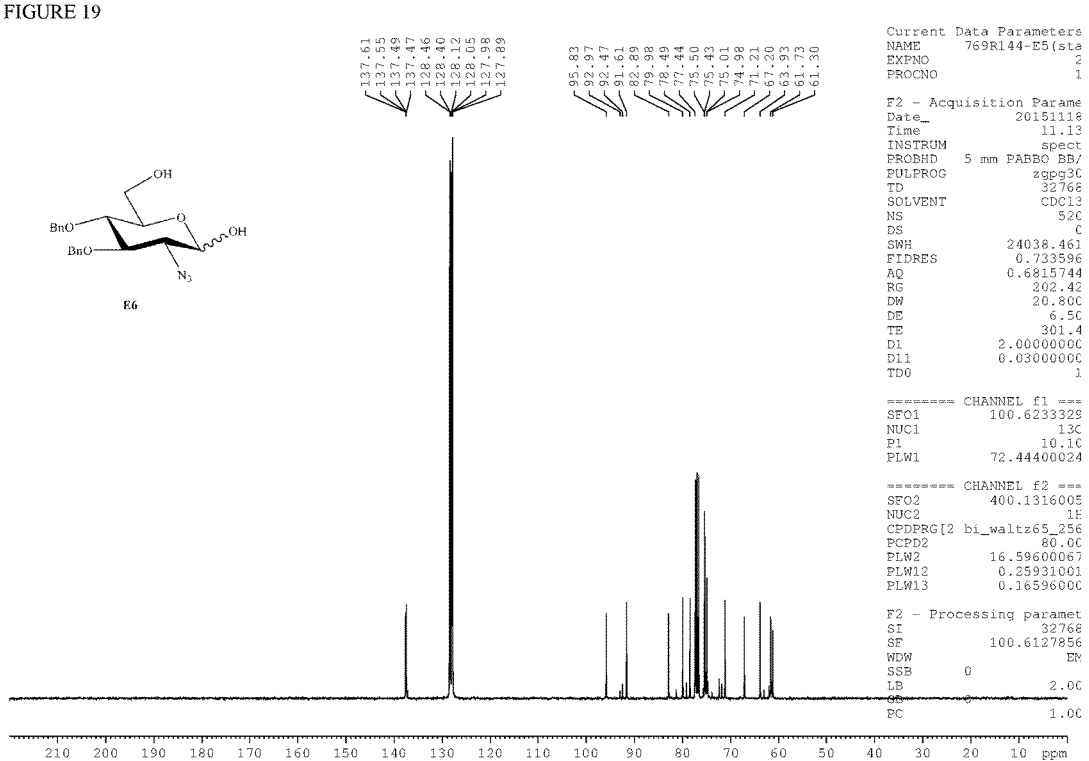
FIG. 19 is a $^{13}$C-NMR spectrum of Monosaccharide E-6.

Methanol (MeOH) (850 ml) was added to the reaction flask containing E-5 (85 g), then potassium carbonate (K$_2$CO$_3$) was added at 5° C. and stirred to solution become clear. The reaction mixture was kept stirring at 0~5° C. until completion checked by UPLC and TLC. Filtered the solution, the cake was washed with methanol, then the combined filtrate was neutralized to pH-7 with Amberlite IR120 ion exchange resin (acidic form). The resulting solution was concentrated under vacuum (15 torr) at 40° C. Crude E-6 (75 g) was obtained. The $^1$H-NMR (400 MHz, CDCl$_3$) of E-6 is shown in FIG. 18. The $^{13}$C-NMR (400 MHz, CDCl$_3$) of E-6 is shown in FIG. 19.

Step 4. In-Situ Preparation of Benzoylformyl Chloride

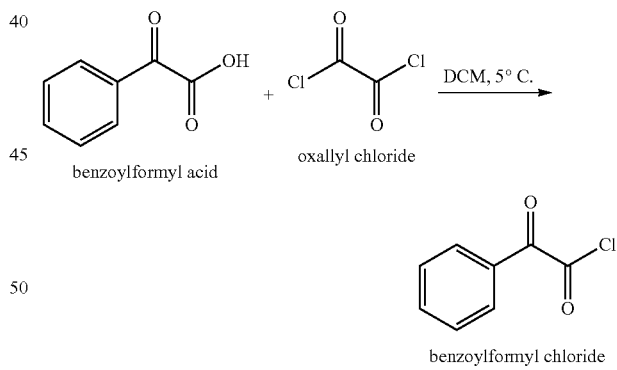

Dichloromethane (400 ml), Benzoylformic acid (85.7 g) were added to the reaction flask and stirred until the reactant dissolved. The reaction mixture was cooled to 0~5° C., then oxallyl chloride was dropwisely added to the solution and stirred for 1.5~2 hours. The solution was concentrated at 30° C. under vacuum (30 torr) to distill dichloromethane and oxallyl chloride until there are no oxallyl chloride remained in the mixture checked by TLC (EA/hexane=1/3). (The sample was taken and mixed with benzyl alcohol and a few drops of triethylamine). Benzoylformyl chloride was achieved, then dichloromethane (200 ml) was added to dissolve.

Step 5. Formation of Monosaccharide E-7

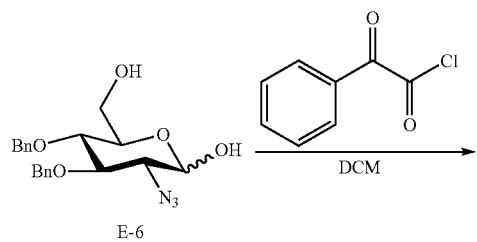

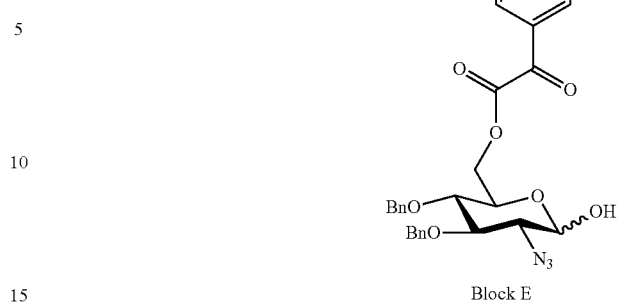

Block E

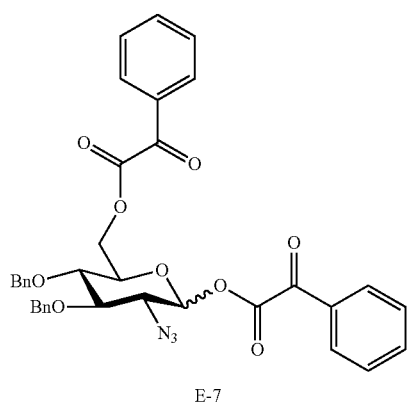

E-7

Dichloromethane (400 ml), E-6 (85.7 g) were added to the reaction flask and cooled to 5° C. Pyridine (104.5 ml) was added to the solution. After the dropwise addition of benzoylformyl chloride below 10° C., the reaction mixture was heated to 20~25° C. and stirred until completion check by TLC (EA/hexane=1/3). Water (400 g) was added to quench the reaction and kept stirring for 20 min, stand for 20 min. The resulting solution was separated into two layers. The dichloromethane layer was extracted with water (400 g) twice. Collect all dichloromethane solutions and added MgSO$_4$ (20 g) for 30 min to absorb water. Filtered the solution, then the filtrate was concentrated under vacuum (15 torr) at 35° C. Crude E-7 (178 g) was obtained.

Step 6. Formation of Monosaccharide E (Block E)

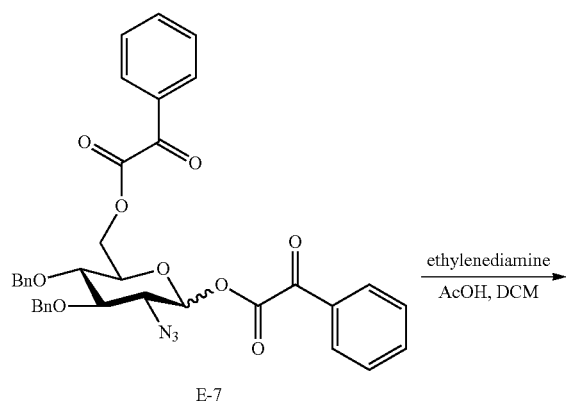

E-7

Figure 20:
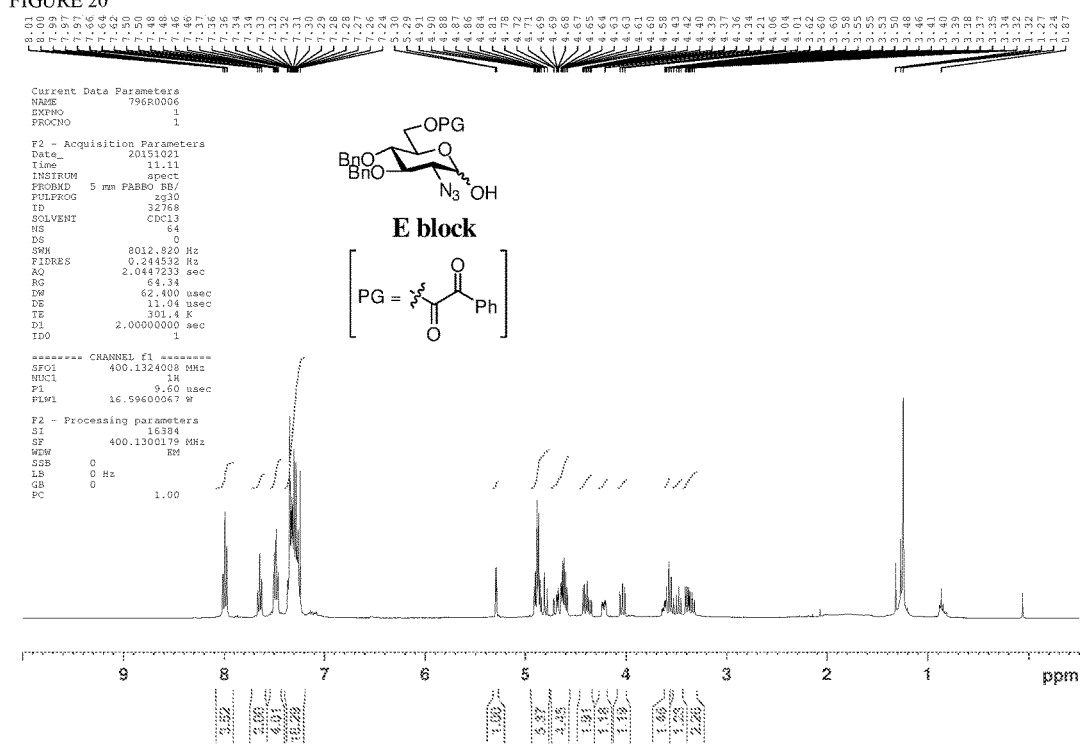
FIG. 20 is a $^1$H-NMR spectrum of Monosaccharide E.
Figure 21:
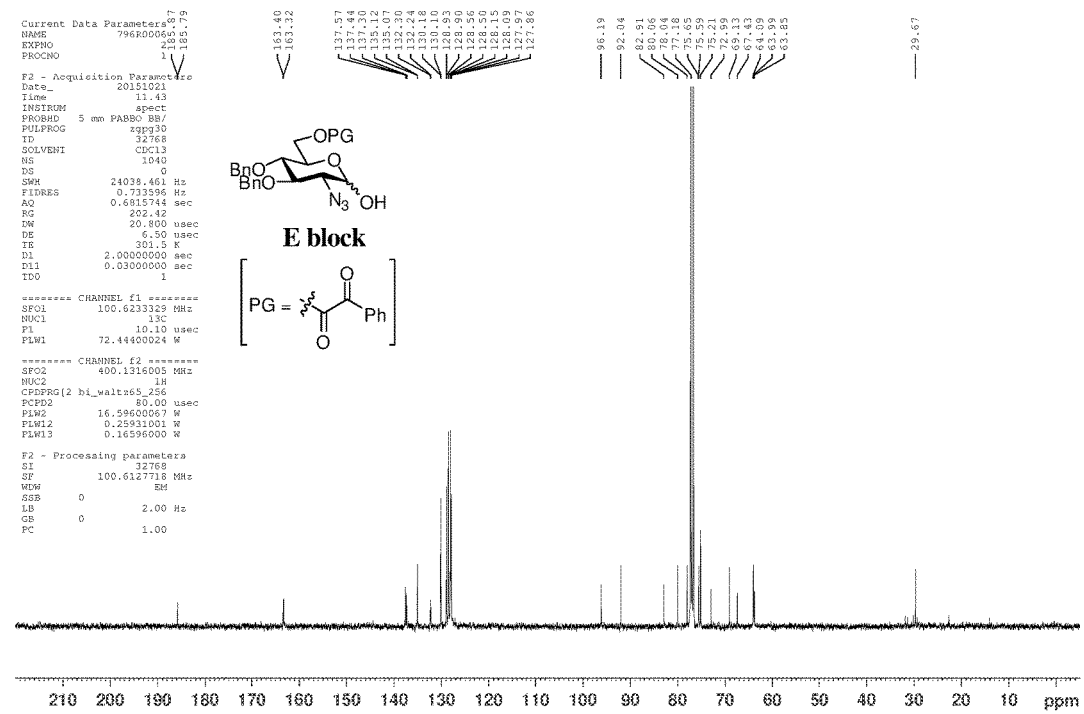
FIG. 21 is a $^{13}$C-NMR spectrum of Monosaccharide E.

Dichloromethane (400 ml), E-6 (85.7 g) were added to the reaction flask and cooled to 5° C. under ice bath. Acetic acid was added to the solution, then ethylenediamine was dropwisely added and stirred. The temperature was controlled below 10° C. during the period of addition. After the addition, the reaction mixture was kept stirring until completion checked by TLC(EA/hexane=1/3). The saturated brine solution (400 ml) was added to quench the reaction and stirred for 20 min, then stand for 20 min. Discard the aqueous layer. The dichloromethane layer was extracted with saturated brine solution (400 ml) twice. Collect all dichloromethane solutions and added MgSO$_4$ (30 g) for 30 min to absorb water. Filtered the solution, then the filtrate was concentrated under vacuum (15 torr) at 40° C. Crude block E (180 g) was obtained. The purified block E (95 g) was obtained by flash column separation. (silica gel; mobile phase: EA/hexane=1/5 (V/V)). The $^1$H-NMR (400 MHz, CDCl$_3$) of Block E is shown in FIG. 20. The $^{13}$C-NMR (400 MHz, CDCl$_3$) of Block E is shown in FIG. 21.

Step 7. Formation of Monosaccharide E (pyruvate)

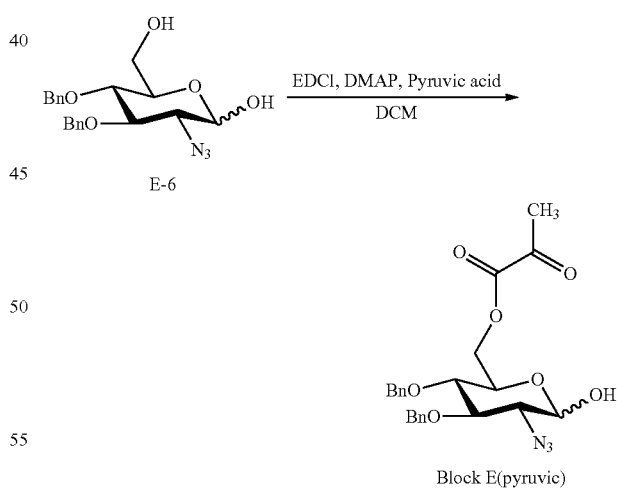

Block E(pyruvic)

Figure 22:
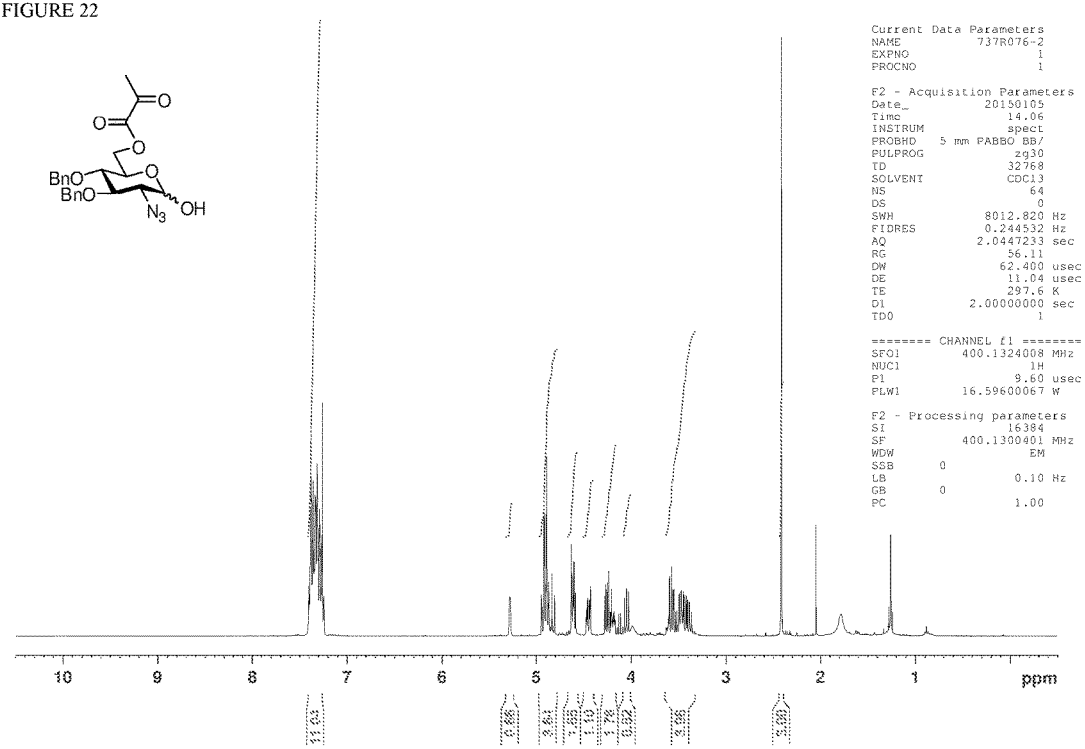
FIG. 22 is a $^1$H-NMR spectrum of Monosaccharide E (pyruvate).

Dichloromethane (10 ml), E-6 (0.5 g), and N,N-dimethylaminopyridine (DMAP) (0.08 g) were added to a 250 ml three-neck round bottle and controlled the temperature at 25~30° C. Pyruvic acid was dropwisely added the reaction solution. After the addition, the reaction mixture was kept stirring until completion checked by TLC (EA/hexane=1/1). Water (20 ml) was added to quench the reaction and DCM (10 ml) was added and stirred for 30 min, then stand for 20 min. The aqueous layer was extracted with DCM (20 ml)

twice. Collect all dichloromethane solutions and added MgSO$_4$ (1 g) for 30 min to absorb water. Filtered the solution, then the filtrate was concentrated under vacuum (15 torr) at 30° C. Crude block E (pyruvate) (0.6 g) was obtained. The purified block E (0.5 g) was obtained by flash column separation. (silica gel; mobile phase: EA/hexane=1/2 (V/V)). The $^1$H-NMR (400 MHz, CDCl$_3$) of Block E (pyruvate) is shown in FIG. 22.

Example 2: Preparation of Monosaccharide D

Step 1. Formation of Monosaccharide D-1

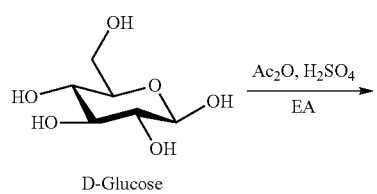

D-Glucose

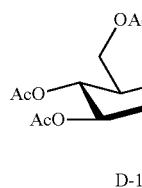

D-1

Ethylacetate (1000 ml) was added to the reaction flask. D-glucose (200 g) was added, then 98% sulfuric acid (6 ml) in ethylacetate was added to the reaction mixture. The solution was cooled to 5~10° C. with ice bath, acetic anhydride (620 ml) was dropwisely added. After the addition, the solution was heated to 20~25° C., then to 50~55° C., the solution turn clear. The reaction extent is checked by TLC (DCM/MeOH=3/1) until completion. 10% NaOH aqueous solution (300 ml) was added to quench the reaction and the temperature was controlled at 15~20° C. during the addition. 7% brine solution (200 ml) was added and stirred for 20 min, then stand for 20 min. 7% brine solution (500 ml) was added to organic layer and stirred for 20 min, then stand for 20 min again. Saturated sodium bicarbonate was added to organic layer nd stirred for 20 min, then stand for 20 min. The organic layer was dried over MgSO4, then evaporated under vacuum (15 torr). White powder of Crude D-1 (429 g) was obtained.

Step 2. Formation of Monosaccharide D-2

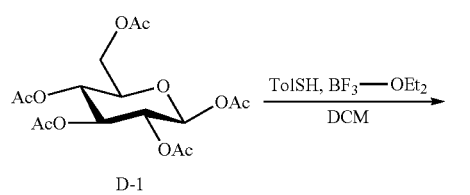

D-1

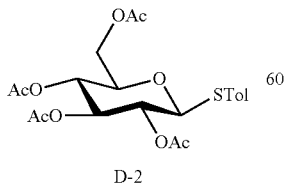

D-2

Dichloromethane (2000 ml) was added to the crude D-1 in step 1 and stirred to dissolve, then the solution was cooled to 0~5° C. with ice bath. 4-thiocresol (168 g) was added to the mixture, the solution become light yellow. 48% BF$_3$-OEt$_2$ was dropwisely added and the temperature was controlled below 5° C. during the period of addition. After the addition, the temperature was raised to 15~20° C. and stirred for overnight until completion checked by TLC (EA/hexane=2/3). The reaction mixture was cooled to 5° C. by portionwise addition of ice (500 g) into the solution and stirred for 20 min, then stand for 20 min. Icy water (1000 ml) was added to the organic layer to remove acid and salts, then saturated sodium bicarbonate aqueous solution was added to neutralize with acid. The organic layer was dried over MgSO4, then evaporated under vacuum (15 torr) to get the light brown powder of D-2 (630 g). White pure powder of D-2 (375 g) was recrystallized from 95% ethanol and vacuum dried.

Step 3. Formation of Monosaccharide D-3

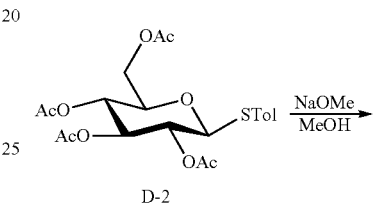

D-2

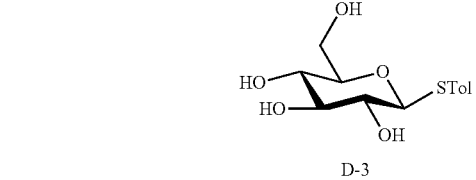

D-3

Dichloromethane (600 ml) was added to the reaction flask containing D-2 (380 g). Methanol (2100 ml) was added and cooled with ice bath, then sodium methoxide (MeOMe) (9.04 g) was added. After the addition, the solution was heated to 30° C. and stirred for 2 hr until completion check by TLC (MeOH/DCM=1/7). Amberlite IR120 ion exchange resin (160 g) was recovered by suction filtration and washed with Dichloromethane (100 ml). The mixture was concentrated under vacuum, the viscous oily liquid, D-3 (235.5 g) was obtained.

Step 4. Formation of Monosaccharide D-4

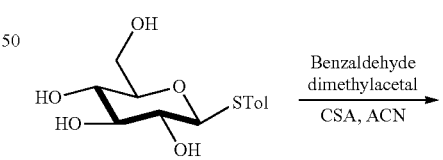

D-3

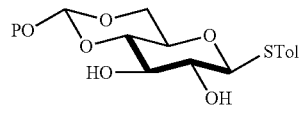

D-4

D-3 (235.5 g) in step 3 was dissolved in acetonitrile (ACN) (1398 ml) at 55° C. DL-10-camphorsulfonic acid (CSA) (38.2 g), Benzaldehyde dimthylactal (137.7 g) were added to the solution and stirred for 3~4 hours until completion checked by TLC (MeOH/DCM=1/3; EA/hexane=1/1).

Trithylamine (17 g) was added to quench the reaction at 50° C. The solution was neutralized with saturated sodium bicarbonate aqueous solution, (pH 2~3→pH 7~8). Hexanes (1300 ml) was added for extracting Benzaldehyde dimthylactal off the solution at 50° C. Pure white powder (162 g) was obtained by recrystallization.

Step 5. Formation of Monosaccharide D-5

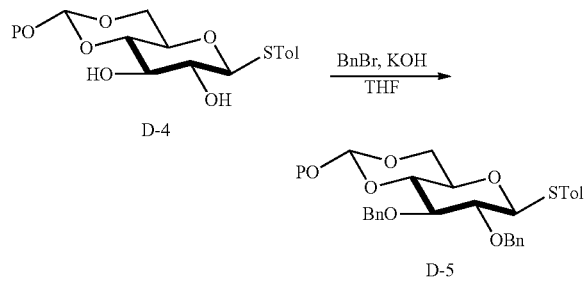

Tetrahydrofuran (THF) (1295 ml), D-4 (162 g), potassium hydroxide (KOH) powder (60.6 g) were added to the reaction flask and stirred. Benzyl bromide (129.3 g), tetrabutylammonium iodide (TBAI) were added. After the addition, the solution was heated to 50~55° C. and stirred for 2 hours. The reaction was not completed yet, then TBAI (3.2 g), KOH (24.5 g) were added, the mixture was heated to 60° C. and stirred until completion check by TLC (EA/hexane=1/4). The reaction mixture was cooled to 20~30° C., ethylacetate (1300 ml), water (650 ml) were added and stirred for 20 min and stand for 20 min. Water (650 ml) was added the organic layer and stirred for 20 min and stand for 20 min. Collect all ethylacetate solutions and added MgSO$_4$ (80.6 g) for 10 min to absorb water. Filtered the solution, then the filtrate was concentrated at 40° C. under vacuum (15 torr). Wet cake of D-5 (277 g) was achieved by recrystallization from 95% EtOH.

Step 6. Formation of Monosaccharide D-6

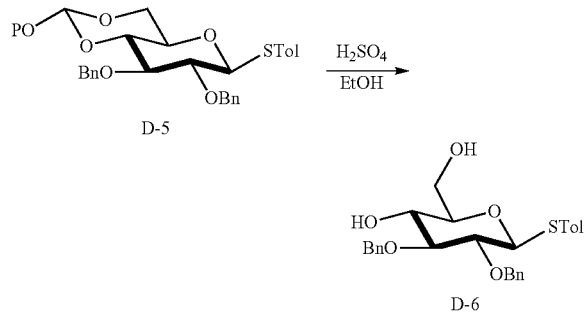

95% EtOH (2223 ml), 98% H2SO4, wet cake of D-5 (278 g) were added to the reactor and stirred. The reaction mixture was heated to 40° C. and stirred for 40 min, then heated to 70° C., the solution become clear and stirred for 1 hour until completion checked by TLC (EA/heaxane=1/1). The mixture was cooled 10~15° C. until white powder formed. After filtration by suction, filtrate was concentrated under vacuum and second crop of white powder of D-6 was obtained. D-6 cake and second crops of D-6 (116.4 g) was combined for next step of reaction. (oxidation reaction).

Step 7. Formation of Monosaccharide D-7

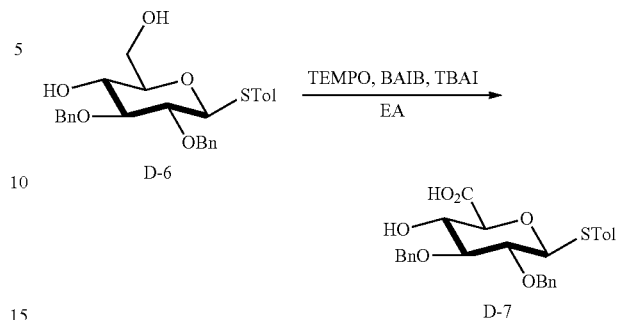

Ethylacetate (2327 ml), D-6 (116.4 g) and water (1163 ml) were added the reaction flask and stirred for dissolution. The reaction temperature was controlled at 25~30° C., then tetrabutylammonium iodide (TBAI) (5.57 g), TEMPO (7.8 g), BAIB (200.9 g) were added and stirred for 2∞3 hour until completion checked by TLC (EA/hexane/AcOH (2/2/0.1=V/V/V). Na$_2$S$_2$O$_3$ was added to quench the reaction and stirred for 15 min, then stand for 20 min. The organic layer was dried over MgSO4, then evaporated under vacuum (15 torr) to get about 150 ml of deep red liquid of D-7.

The pure D-7 (106.2 g) was obtained by flash column purification with gradient elution (silica gel; mobile phase: EA/hexane=1/3, EA/hexane/AcOH=1/1/0.2, EA, EA/MeOH=3/1).

Step 8. Formation of Monosaccharide D (Block D)

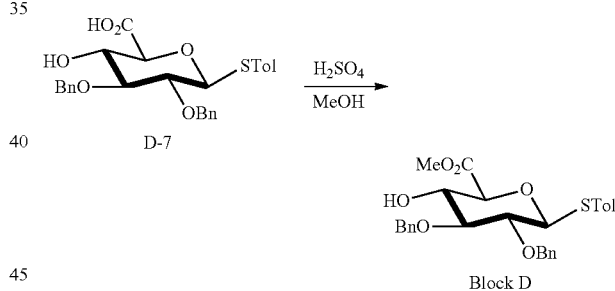

Methanol (1060 ml), D-7 (106.2 g) were added the reaction flask and stirred for dissolution. 98% Sulfuric acid (5.41 g) dissolved in methanol (10 ml) was added dropwisely to the solution. After the addition, the solution was heated to 55° C. and stirred for couple of hours until completion checked by TLC (EA/hexane/AcOH=1/1/0.2). 10% NaOH aqueous solution (17 ml) was added to quench the reaction and adjusted pH to 7~8. The resulting solution was concentrated to almost dryness, then ethylacetate (350 ml) and sodium chloride(sat) (350 ml) were added and stirred for 15 min. Stand for 15 min. The solution was separated into two layers. The organic layer was dried over MgSO4, then evaporated under vacuum (13 torr) at 40° C. to get yellowish brown crude Block D cream. The pure Block D (45.1 g) was obtained by flash column purification with gradient elution (silica gel; mobile phase: EA/hexane=1/10, EA/hexane=1/8, EA/hexane=1/6, EA/hexane=1/4). The combined pure fractions of Block D was concentrated under vacuum, then the pure block D was obtained from recrystallization with DCM/hexane=1/12).

Figure 23:
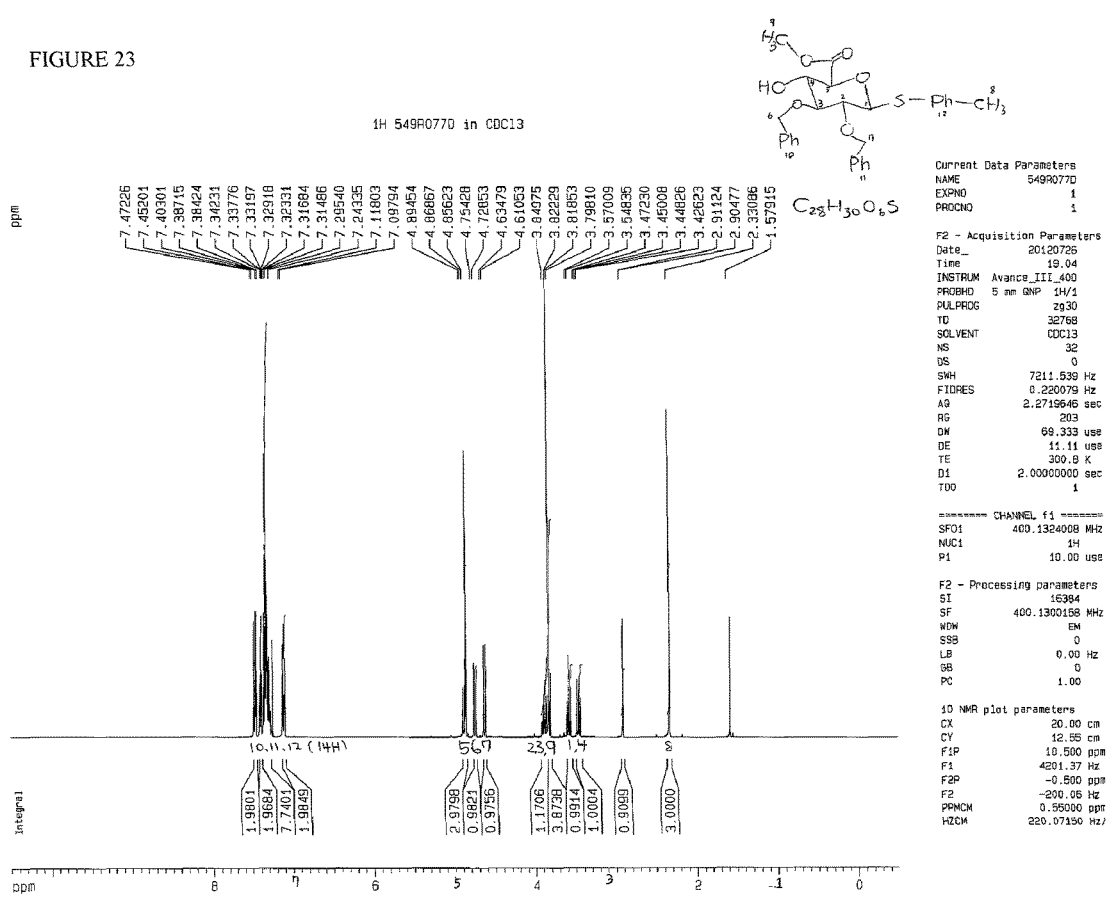
FIG. 23 is a $^1$H-NMR spectrum of Monosaccharide D.
Figure 24:
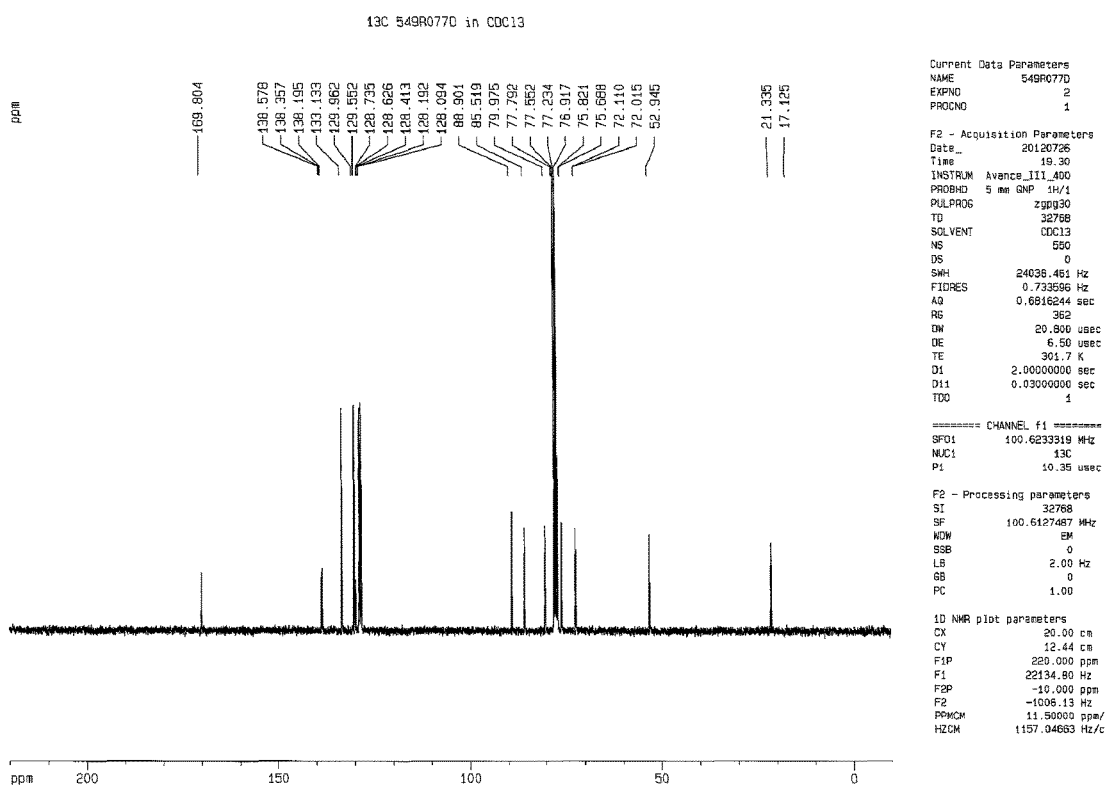
FIG. 24 is a $^{13}$C-NMR spectrum of Monosaccharide D.

The $^1$H-NMR (400 MHz, CDCl$_3$) of Block D is shown in FIG. 23. The $^{13}$C-NMR (100 MHz, CDCl$_3$) of Block D is shown in FIG. 24.

Example 3: Preparation of Monosaccharide C

Step 1. Formation of Monosaccharide C-1

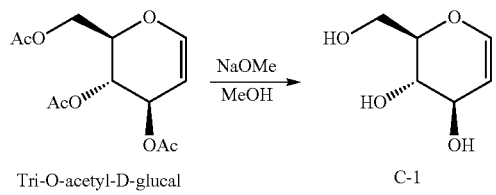

Tri-O-acetyl-D-glucal

C-1

Methanol (800 ml) was added to the reaction flask. Tri-Oacetyl-D-glucal (200 g), sodium methoxide (1.98 g) was added and stirred for 30 min. The reaction mixture was checked by TLC (EA) until completion. The mixture was neutralized with Amberlite IR 120 ion exchange resin (acid form, 20 g) until pH 7.0. Amberlite IR 120 ion exchange resin was recovered by suction filtration and washed with methanol (200 ml).

The mixture was concentrated under vacuum, the viscous oily liquid, E-1 was obtained.

Step 2. Formation of Monosaccharide C-2

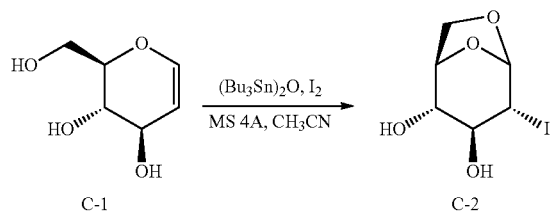

Acetonitrile (200 ml) was added the reaction flask containing viscous oily E-1 and stirred for about 20 min until the reaction mixture become clear, then molecular sieve 4 A (21.5 g), acetonitrile (1500 ml) were added. The mixture was heated to 55° C.

The sample was taken for determination of water content by KF titration (KF NMT 0.05%). Cool the reaction solution to 20° C., after the addition of tributyl tin oxide (600 ml), the mixture was heated to 70° C. and stirred for 3 hours. The reaction mixture was cooled to 25° C. for 20 min, 5~10° C. for 20 min. Portionwisely addition of iodine (two portions, 447 g) to the reaction solution at 15~20° C. and stirred for 9 hours. The sample was taken for checking the reaction extent by TLC. If the reaction is not complete, the iodine (44 g) was added the solution every time and stirred further 4 hours. The mixture was filtered through a celite pad (35 g celite). The cake was washed with acetonitrile (600 ml).

The solution was concentrated to 1000 ml Sodium thiosulfate solution(sat) (430 ml), n-hexane (660 ml) were added and stirred for 20 min, then stand for 15 min. the solution was separated into two phases. Collect the acetonitrile layer and check by TLC. Iterated the above-mentioned procedure three times to remove the tributyl tin oxide. The combined solution was evaporated to almost dryness under vacuum. Ethylacetate (880 ml) was added to the solution and stirred for 20 min, then stand for separation to collect the ethylacetate layer. Iterated the above-mentioned procedure five times to extract E-2. Combined all extracts which was concentrated at 45° C. under vacuum (10 torr). The yellowish powder, E-2 (C-2) was obtained (290 g, 74%).

Step 3. Formation of Monosaccharide C-3

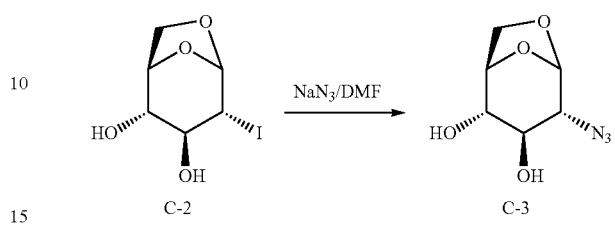

N,N-Dimethylformamide (DMF) (250 ml) and water (25 ml) were added the reaction flask. Sodium azide (100 g) was added and stirred for 20 min. The reaction solution was heated to 120° C. and stirred for 3 hours, then the reaction extent was checked by TLC. After E-2 was disappeared on TLC plate, the solution was cooled to 25° C. The mixture was filtered through a celite pad and the cake was rinsed with Ethylacetate (130 ml). The filtrate was evaporated at 50° C. under vacuum (10 torr) to get crude E-3 (C-3) (180 g). The pure E-3 (C-3) (68 g) was obtained by flash column purification (silica gel; mobile phase: ethylacetate).

Step 4. Formation of Monosaccharide C-4

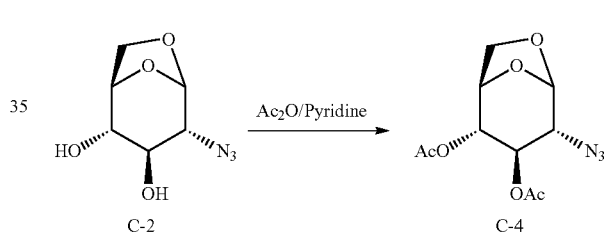

C-3 (27 g), acetic anhydride (Ac$_2$O) (58.9 g), pyridine (108 ml) were added to the reaction flask and stirred for about 4 hours. The sample was taken for checking the extent of reaction by TLC (EA/hexane=1/1) until completion. 0.1N HCl aqueous solution (54 ml) was added to quench the reaction, then toluene was added to the solution and stirred for 20 min and stand for 20 min. Discard the aqueous layer. Iterate the washing procedure for addition of 0.1N HCl aqueous solution (54 ml) to the toluene layer until pH 7∞8. Collect all toluene solutions and added MgSO$_4$ (5 g) for 30 min to absorb water. Filtered the solution, then the filtrate was concentrated at 35° C. under vacuum (15 torr). Crude C-4 (32 g) was obtained.

Step 5. Formation of Monosaccharide C-5

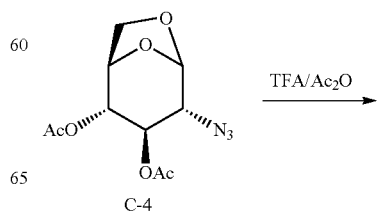

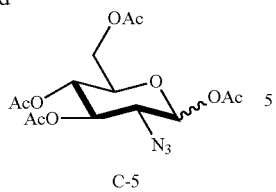

C-5

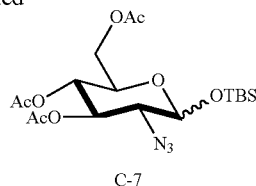

C-7

C-4 (5 g), acetic anhydride (Ac$_2$O) (50 ml), trifluoroacetic acid (TFA) (6.3 g) were added to the reaction flask. The reaction mixture was heated to 60° C. and stirred until C-4 disappeared completely on TLC plate. 45% sodium hydroxide aqueous solution was dropwisely added to quench the reaction, then toluene (50 ml) was added and stirred for 20 min and stand for 20 min. Water (50 ml) was added to the toluene layer for removal of acetic acid and TFA. The organic layer was dried over MgSO4, then evaporated under vacuum (15 torr) at 45° C. White powder of Crude C-5 (6.2 g) was obtained.

Step 6. Formation of Monosaccharide C-6

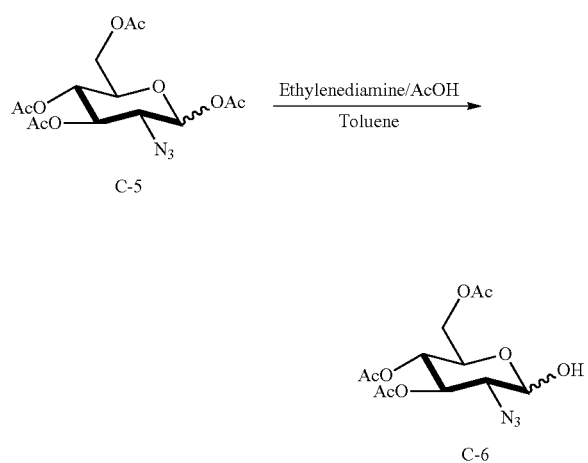

Toluene (100 ml), crude C-5 (6.3 g) were added to the reaction flask and stirred for dissolution, then the solution was cooled to 0~5° C. Acetic acid (1 g) was added and stirred for 10 min, then ethylenediamine was added dropwisely. After the addition, the temperature of reaction mixture was controlled at 20~30° C. The solution was stirred until C-5 disappeared on TLC plate (EA/hexane=1/1). Water (18 ml) was added to quench the reaction, stirred for 20 min and stand for 20 min. Organic layer was washed with water (18 ml). The organic layer was dried over MgSO4, then evaporated under vacuum (15 torr) at 45° C. Yellow oily Crude C-6 (4.7 g) was obtained.

Step 7. Formation of Monosaccharide C-7

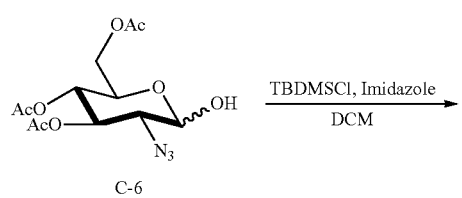

C-6 (4.5 g) was dissolved in DCM (9 ml) in reaction flask. Imidazole (1.9 g), TBDMSCl (2.34 g) were added and stirred for 2 hour until completion check by TLC (EA/hexane=1/2). Water (27 ml) was added to quench the reaction, stirred for 20 min and stand for 20 min. Aqueous layer was extracted with DCM (18 ml). The combined organic layers was dried over MgSO$_4$, then evaporated under vacuum (15 torr) at 35° C. Yellow oily Crude C-7 (5.4 g) was obtained. The pure white powder of C-7 (4.9 g) was obtained by flash column purification with gradient elution (silica gel; mobile phase:EA/hexane=1/10, EA/hexane=1/8, EA/hexane=1/7, EA/hexane=1/6, EA/hexane=1/5) and concentrated.

Step 8. Formation of Monosaccharide C-8

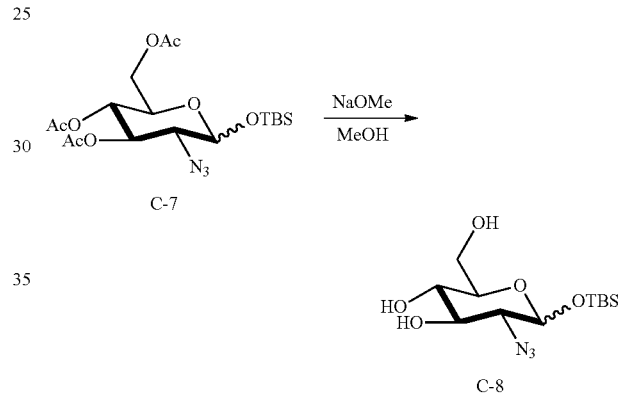

MeOH (16 ml), C-7 (4 g) and NaOMe (0.024 g) was added to the reaction flask an. After the addition, the temperature of solution was controlled at 30° C. and stirred for 30 min until completion check by TLC (MeOH/DCM=1/7). Amberlite IR120 ion exchange resin (4.1 g) was recovered by suction filtration and washed with Dichloromethane (100 ml). The mixture was concentrated under vacuum, light yellow liquid, C-8 (2.7 g) was obtained.

Step 9. Formation of Monosaccharide C-9

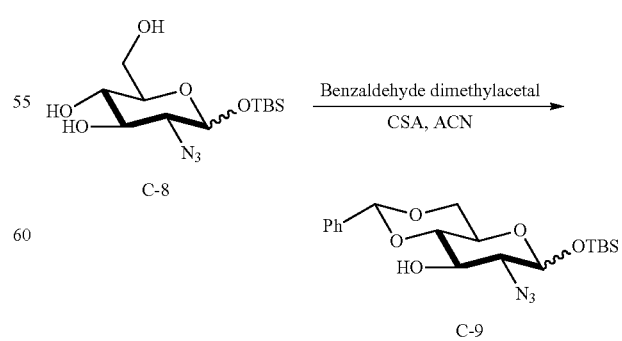

C-8 (2.6 g) was dissolved in acetonitrile (ACN) (10 ml) at 55° C. DL-10-camphorsulfonic acid (CSA) (0.05 g), Benzaldehyde dimethylactal (2.44) were added to the solution and stirred for 6 hours until completion checked by TLC (EA/hexane=3/2). Sodium bicarbonate(sat) (15 ml) was added to quench the reaction. The solution was neutralized with saturated sodium bicarbonate aqueous solution, (pH 2~3→pH 7~8). Hexanes (15 ml) was added for extracting Benzaldehyde dimthylactal off the solution at 50° C. Toluene (15 ml) was added to the solution, then stirred for 20 min and stand for 20 min. All toluene solution was combined and concentrated to obtain crude C-9. The pure white powder of C-9 (2.2 g) was obtained by flash column purification with gradient elution(silica gel; mobile phase: EA/hexane=1/10, EA/hexane=1/9, EA/hexane=1/8, EA/hexane=1/6) and concentrated.

Step 10. Formation of Monosaccharide C-10

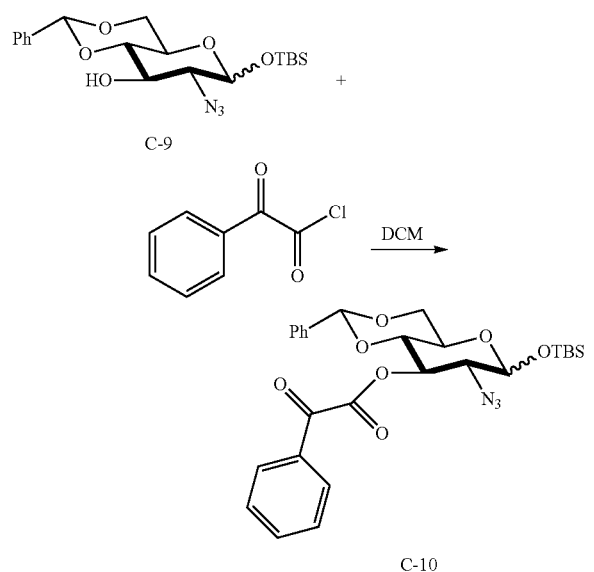

C-10

DCM (280 ml), benzoylformic acid (31 g) were added to 500 ml three-neck reaction flask and stirred. The reaction mixture was cooled to 0~5° C., oxallyl chloride (24 g) was added and stirred for 90 min. Oxallyl chloride in the reaction solution was distilled under vacuum (30 torr) at 30° C. until complete removal from the solution checked by TLC (EA/hexane=1/3; BnOH and a drop of TEA was added into sample).

DCM (280 ml) was added to dissolve the reaction mixture, then transfer to addition funnel.

Figure 25:
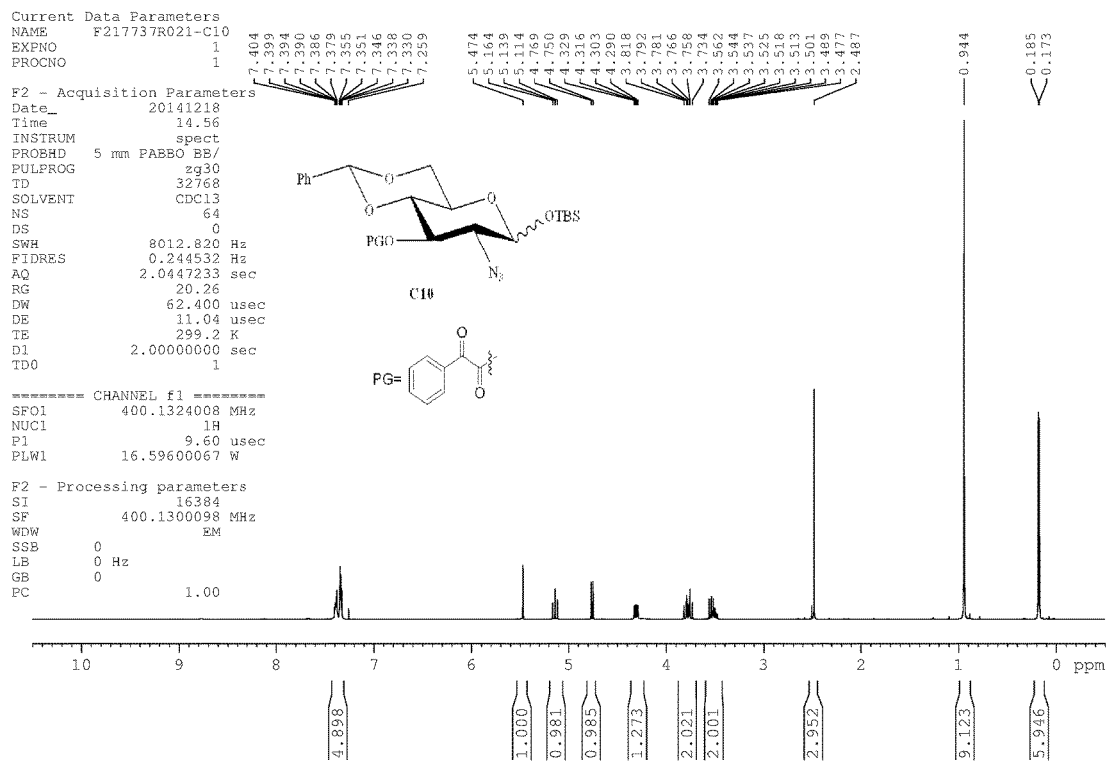
FIG. 25 is a $^1$H-NMR spectrum of Monosaccharide C-10.
Figure 26:
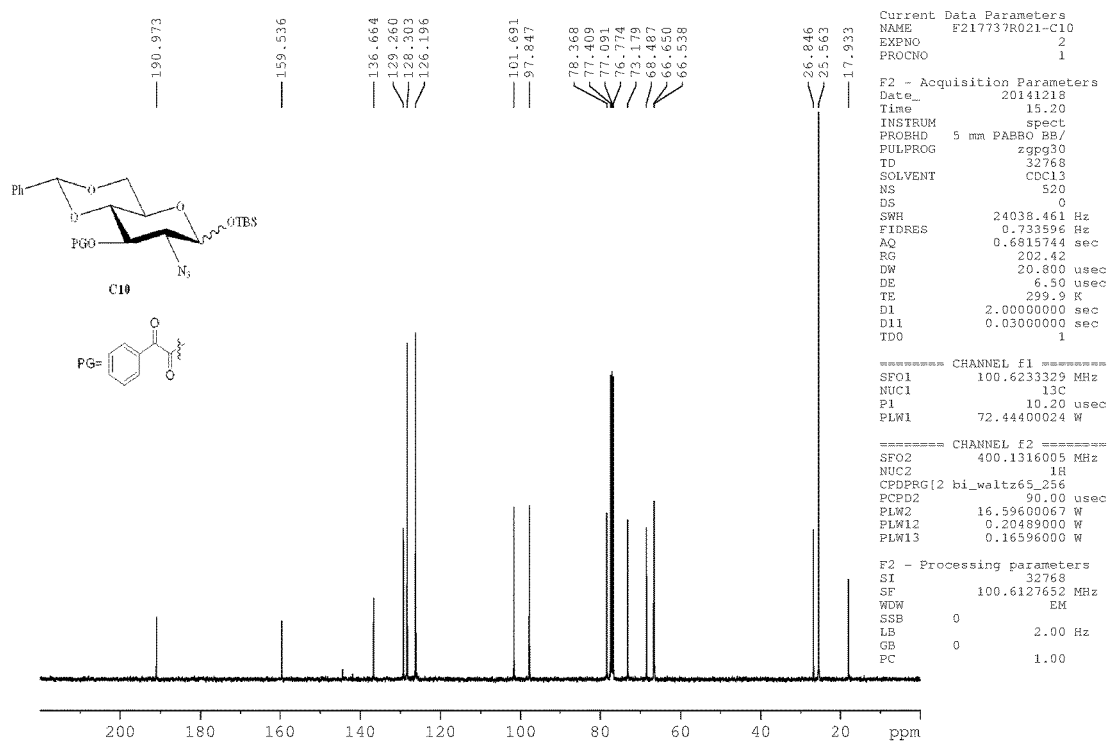
FIG. 26 is a $^{13}$C-NMR spectrum of Monosaccharide C-10.

C-9 (70 g) was dissolved in DCM (280 ml) in the reaction flask. The resulting benzoylformyl chloride solution was dropwisely added to the reaction solution, the temperature was controlled below 10° C. during the period of addition (about 40 min). After the addition, the solution was stirred for 1 hour until completion checked by TLC (EA/hexane=1/5). Water (280 ml) was added to quench the reaction, stirred for 20 min and stand for 20 min. Organic layer was washed with water (280 ml) twice. The combined organic layers was dried over MgSO4, then evaporated under vacuum (15 torr) at 35° C. Crude C-10 (102 g) was obtained. The $^1$H-1-NMR (400 MHz, CDCl$_3$) of C-10 is shown in FIG. 25. The $^{13}$C-NMR (400 MHz, CDCl$_3$) of C-10 is shown in FIG. 26.

Step 11. Formation of Monosaccharide C-11

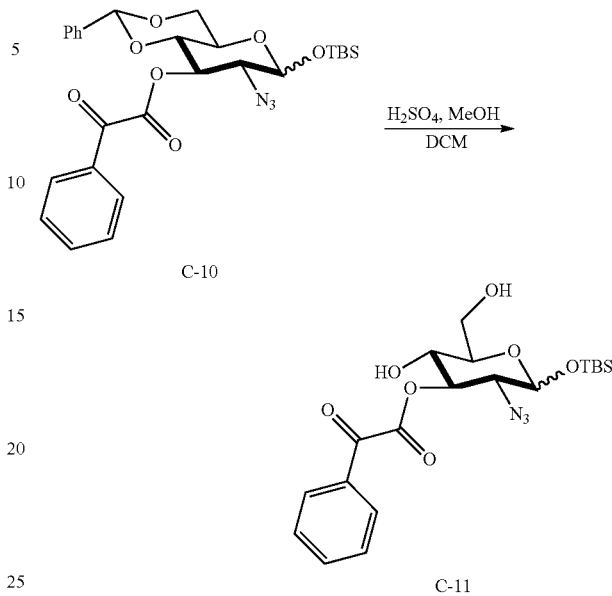

Figure 27:
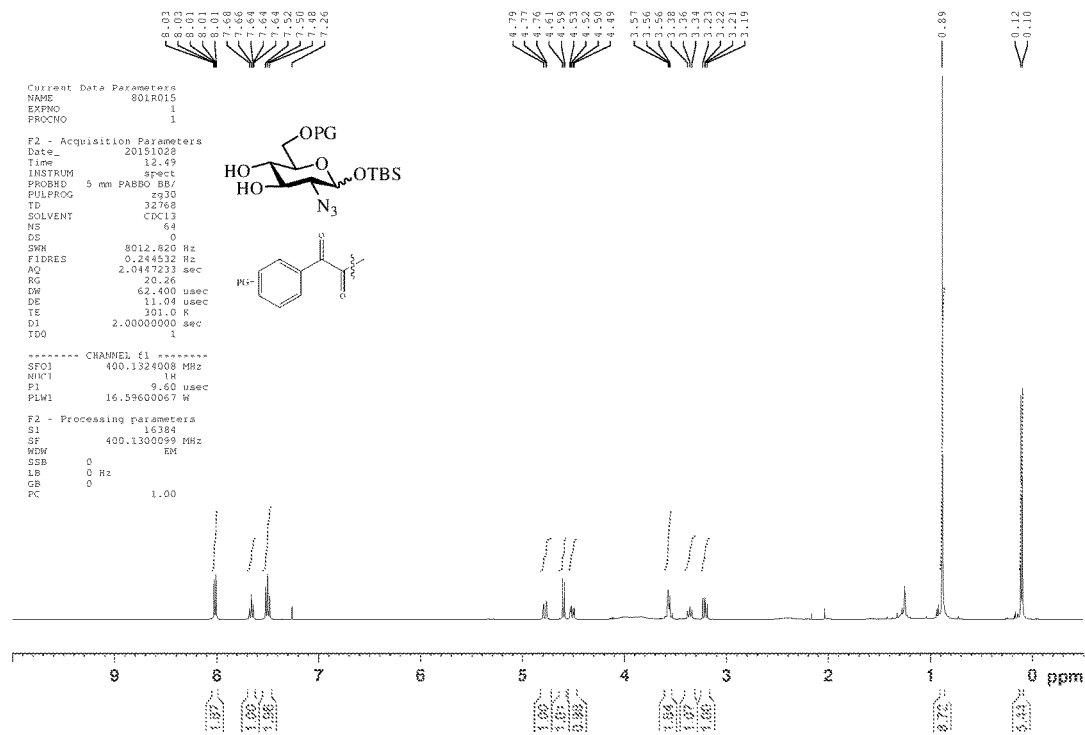
FIG. 27 is a $^1$H-NMR spectrum of Monosaccharide C-11.
Figure 28:
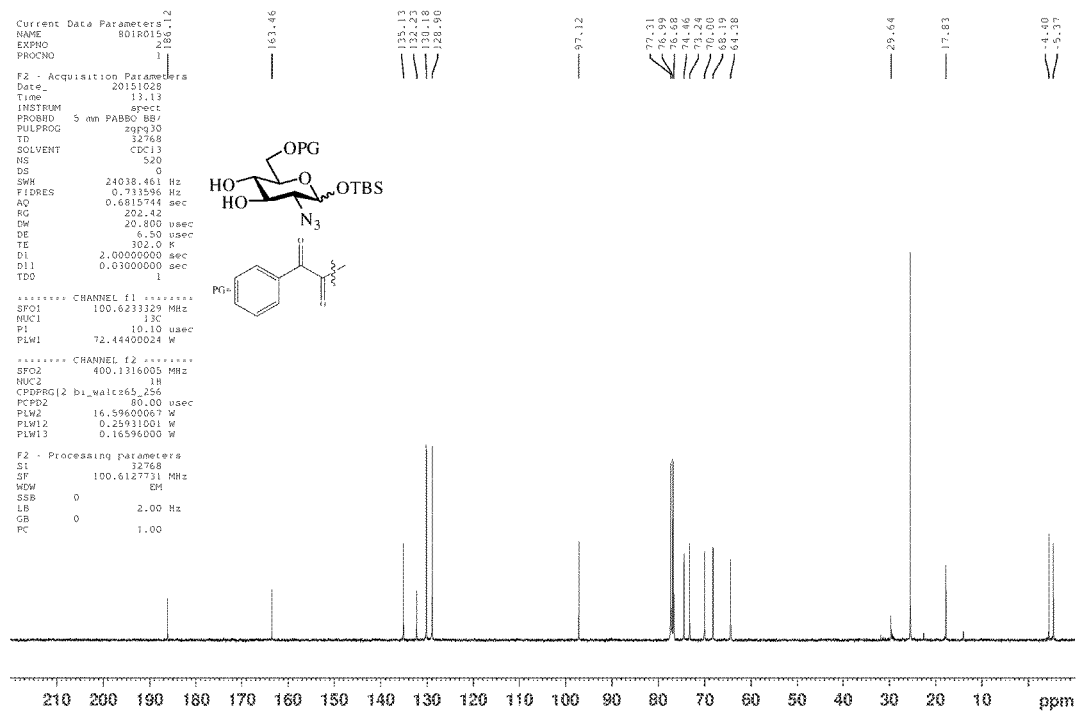
FIG. 28 is a $^{13}$C-NMR spectrum of Monosaccharide C-11.

DCM (150 ml) was added to dissolve C-10 (10 g) in the reaction flask. The reaction solution was cooled to 0~5° C., MeOH (25 ml) and 98% sulfuric acid (1.6 ml) were added and stirred for 3 hours until completion checked by TLC (EA/hexane=1/1). Sodium bicarbonate(sat) (100 ml) was added to quench the reaction, the temperature was controlled below 10° C. and stirred for 20 min and stand for 20 min. Aqueous layer was extracted with DCM (18 ml). The combined organic layers was dried over MgSO$_4$ (2.5 g), then evaporated under vacuum (30 torr) at 30° C. The $^1$H-NMR (400 MHz, CDCl$_3$) of C-11 is shown in FIG. 27. The $^{13}$C-NMR (400 MHz, CDCl$_3$) of C-11 is shown in FIG. 28.

Step 12. Formation of Monosaccharide C (Block C)

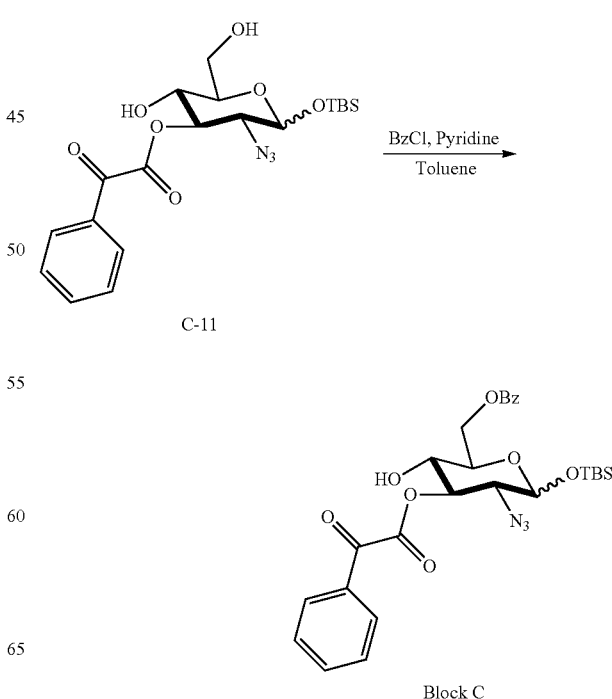

Block C

Figure 29:
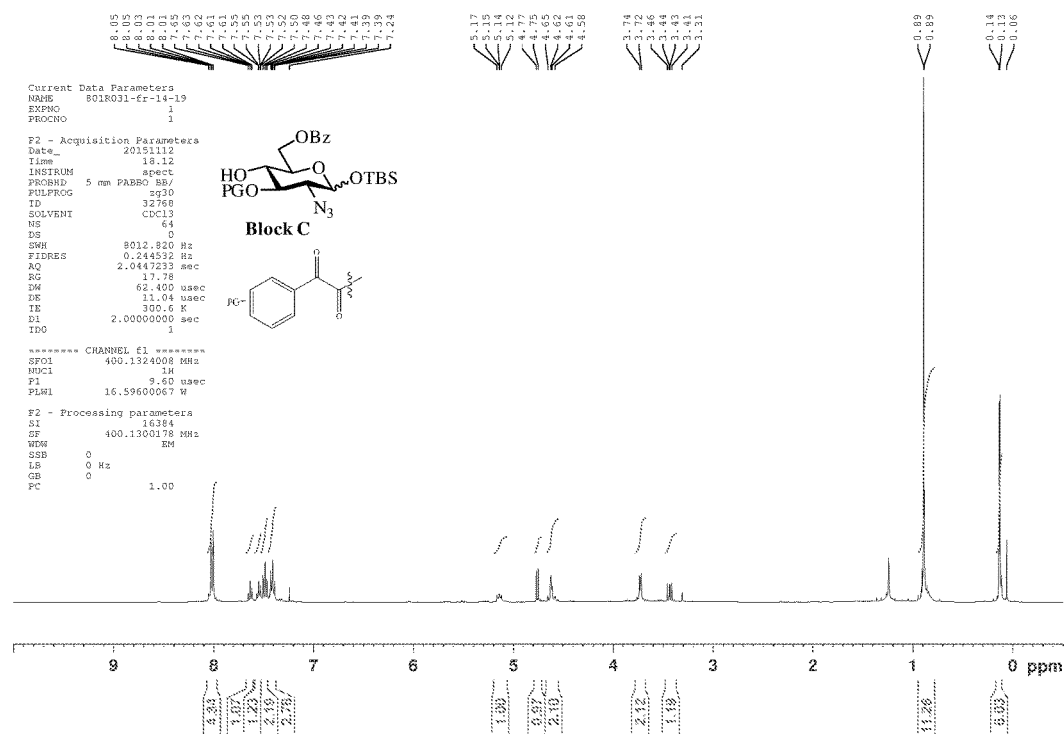
FIG. 29 is a $^1$H-NMR spectrum of Monosaccharide C.
Figure 30:
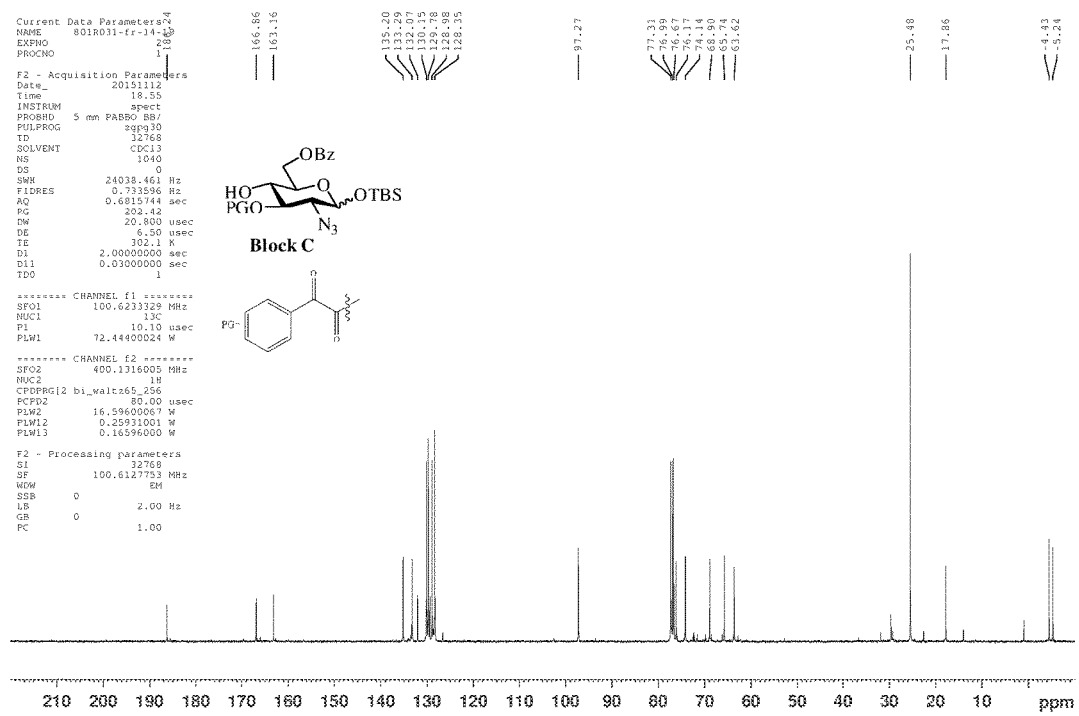
FIG. 30 is a $^{13}$C-NMR spectrum of Monosaccharide C.

Crude C-11 (10 g) in step 11 was dissolved in toluene (100 ml) in 500 ml three-neck reaction flask. After the addition of pyridine (3.85 g), the mixture was cooled to −30~−35° C. Benzoyl chloride (2.8 g) was dropwisely added to the reaction solution, the temperature was controlled below −30° C. during the period of addition. After the addition, the solution was stirred for 30 min until completion checked by TLC (Tol/ACT=6/1). Water (60 ml) was added to quench the reaction, stirred for 20 min and stand for 20 min. Organic layer was washed with 0.1N HCl (aq) (30 ml). The organic layer was washed with NaHCO$_3$(sat) (75 ml). The combined organic layers was dried over MgSO$_4$ (2 g), then evaporated under vacuum (12 torr) at 37° C. Crude Block C (12.5 g) was obtained. Pure Block C (6.5 g) was obtained by flash column purification with gradient elution (silica gel; mobile phase: BuOAc/hexane=1/8, BuOAc/hexane=1/7, BuOAc/hexane=1/6, BuOAc/hexane=1/5) and concentrated under vacuum (12 torr) at 40° C. The $^1$H-NMR (400 MHz, CDCl$_3$) of Block C is shown in FIG. 29. The $^{13}$C-NMR (100 MHz, CDCl$_3$) of Block C is shown in FIG. 30.

Example 4: Preparation of Trisaccharide EDC-1 (TS-1)

Step 1. Formation of Disaccharide ED-1(DS-1)

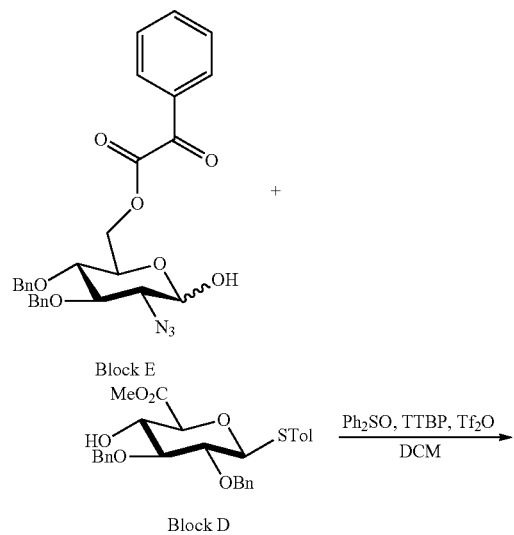

Figure 31:
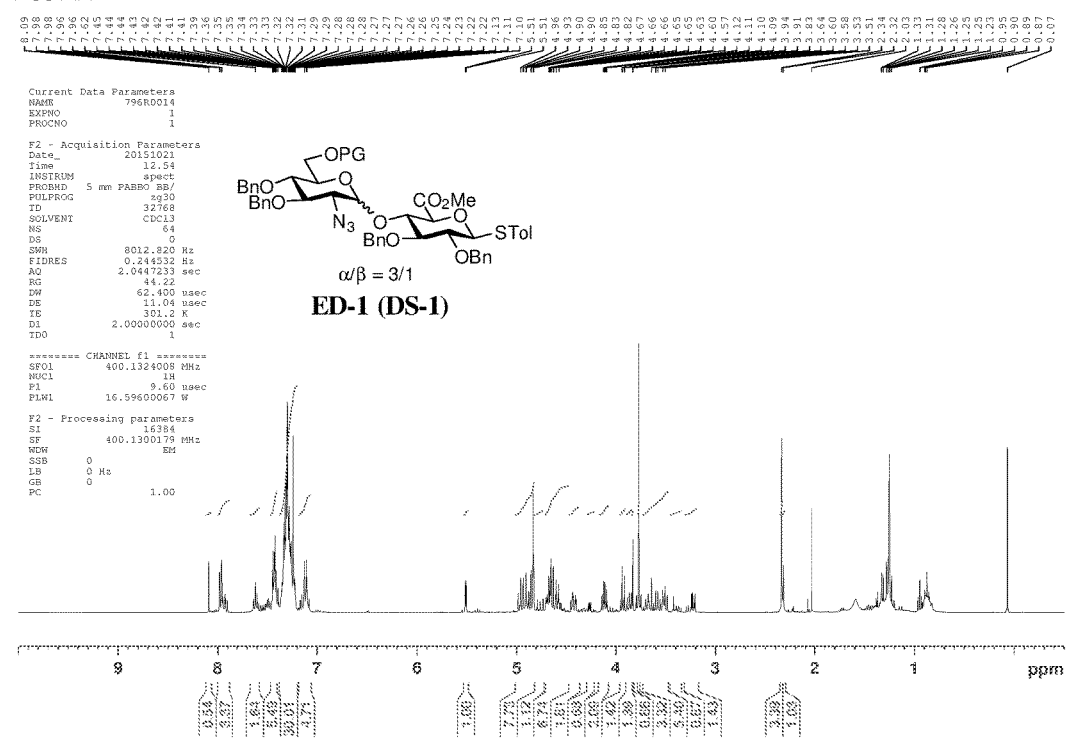
FIG. 31 is a $^1$H-NMR spectrum of Disaccharide ED-1.
Figure 32:
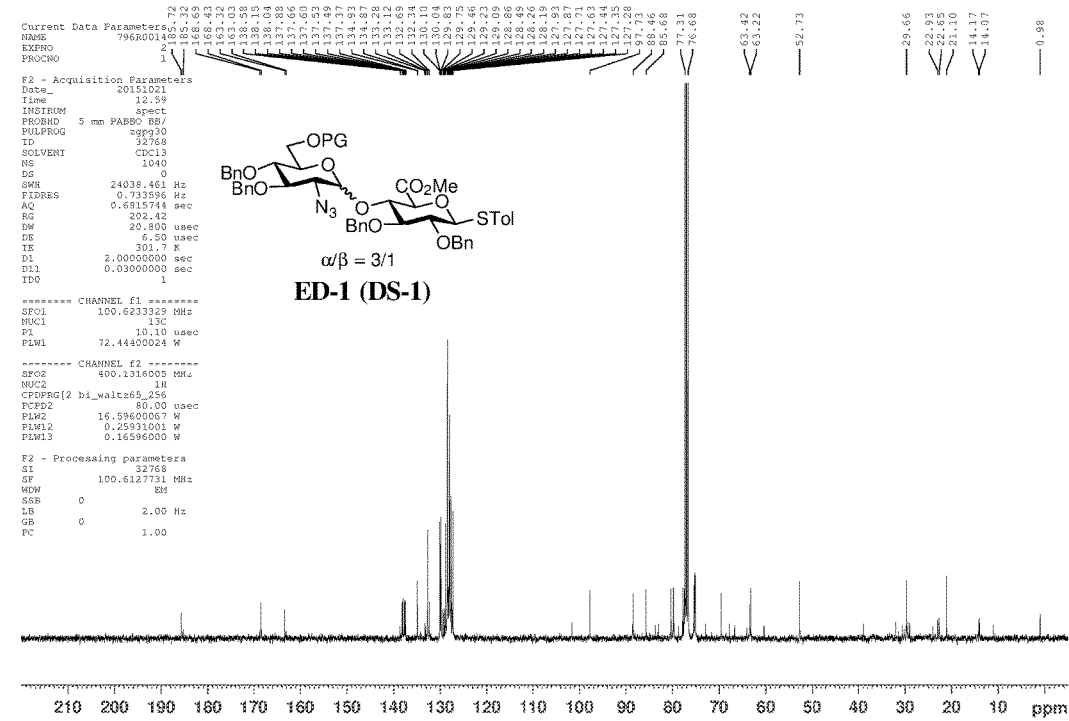
FIG. 32 is a $^{13}$C-NMR spectrum of Disaccharide ED-1.

Dichloromethane (720 ml), molecular sieve 4 Å (22 g) and Block D (120 g) were added to a 2000 ml three-neck reaction flask (A) and stirred for 30 min at 20~30° C. The sample was taken for determination of water content by KF titration (KF NMT 0.03%). A 250 ml three-neck reaction flask (B) was equipped with a mechanical stirrer and a vacuum pump, Dichloromethane (1260 ml), 2,4,6-tri-tert-butyl-pyrimidine (TTBP) (121 g), diphenyl sulfoxide (Ph$_2$SO) (64 g), Block E (140 g) and molecular sieve 4 Å (55 g) were added, then the reaction mixture was dried by heat gun under vacuum at 20~30° C. The sample was taken for determination of water content by KF titration (KF NMT 0.03%). The solution in flask B was cooled to −60~−55° C., then triflic anhydride (Tf$_2$O) (55 ml) was added slowly and kept the reaction temperature at −58~−48° C. during the period of addition. The Block D (120 g) in flask A was added to the reaction flask B and kept the reaction temperature at −55~−45° C. during the period of addition. After the addition, the temperature was raised to −40~−32° C. within 20 min and stirred for 3~4 hours until completion checked by TLC (DCM/EA/hexane=1/1/7, V/V/V). Triethylamine (100 ml) was added to quench the reaction and kept stirring for 20 min, stand for 20 min. The resulting solution was separated into two layers. The dichloromethane layer was extracted with water (1000 g) twice. Collect all dichloromethane solutions and added MgSO$_4$ (30 g) for 30 min to absorb water. Filtered the solution, then the filtrate was concentrated under vacuum (15 torr) at 35° C. Crude DS-1 (125 g) was obtained. The purified DS-1 (α form) (108 g) was obtained by flash column separation. (silica gel; mobile phase: DCM/EA/hexane=1/1/10(V/V/V)). The $^1$H-NMR (400 MHz, CDCl$_3$) of ED-1 is shown in FIG. 31. The $^{13}$C-NMR (100 MHz, CDCl$_3$) of ED-1 is shown in FIG. 32.

Step 2. Formation of Disaccharide ED-2 (DS-2)

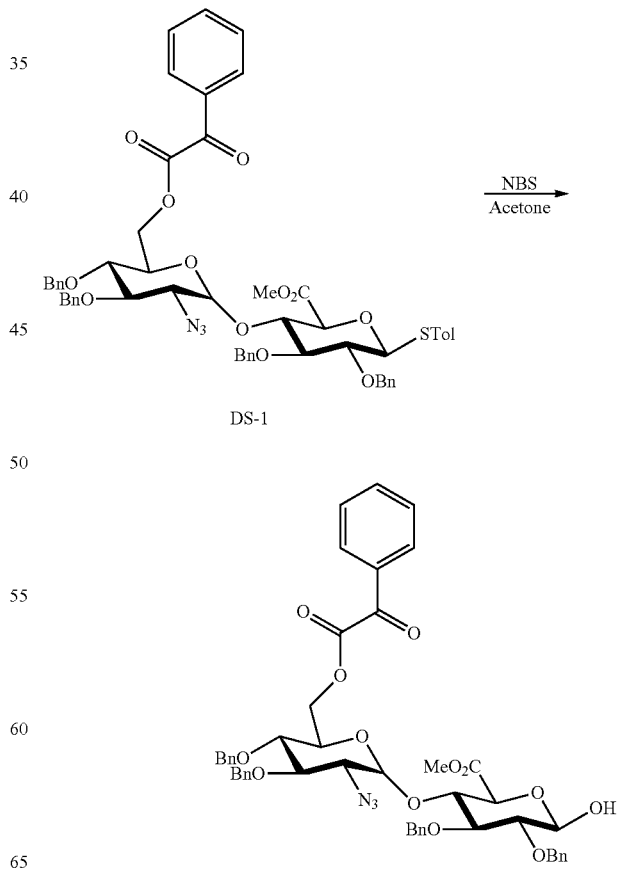

Acetone (900 ml), water (30 ml) and Disaccharide ED-1 (DS-1) (108 g) were added to a 2000 ml three-neck reaction flask. The reaction solution was cooled to 0~5° C. N-bromosuccinimide(NBS)(760 g) was added and stirred for 30 min until completion checked by TLC (EA/hexane=1/3). Sodium thiosulfate(sat) (80 ml) was added to quench the reaction, then concentrated to almost dryness under vacuum (40 torr) at 40° C. DCM (1000 ml) was added to the flask for extraction of Disaccharide ED-2 (DS-2). $MgSO_4$ (30 g) was added to the solution for 30 min to absorb water. Filtered the solution, then the filtrate was concentrated under vacuum (15 torr) at 40° C.

Step 3. Formation of Disaccharide ED-3 (DS-3)

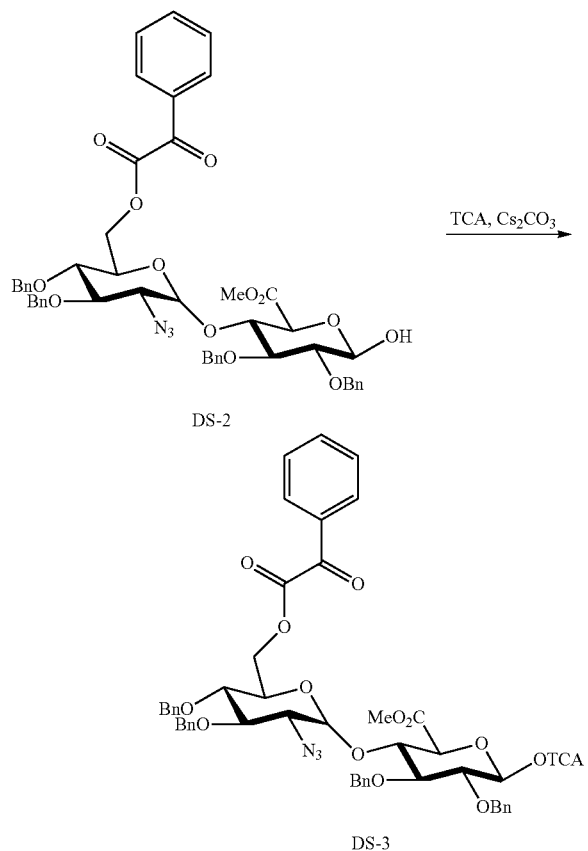

Figure 33:
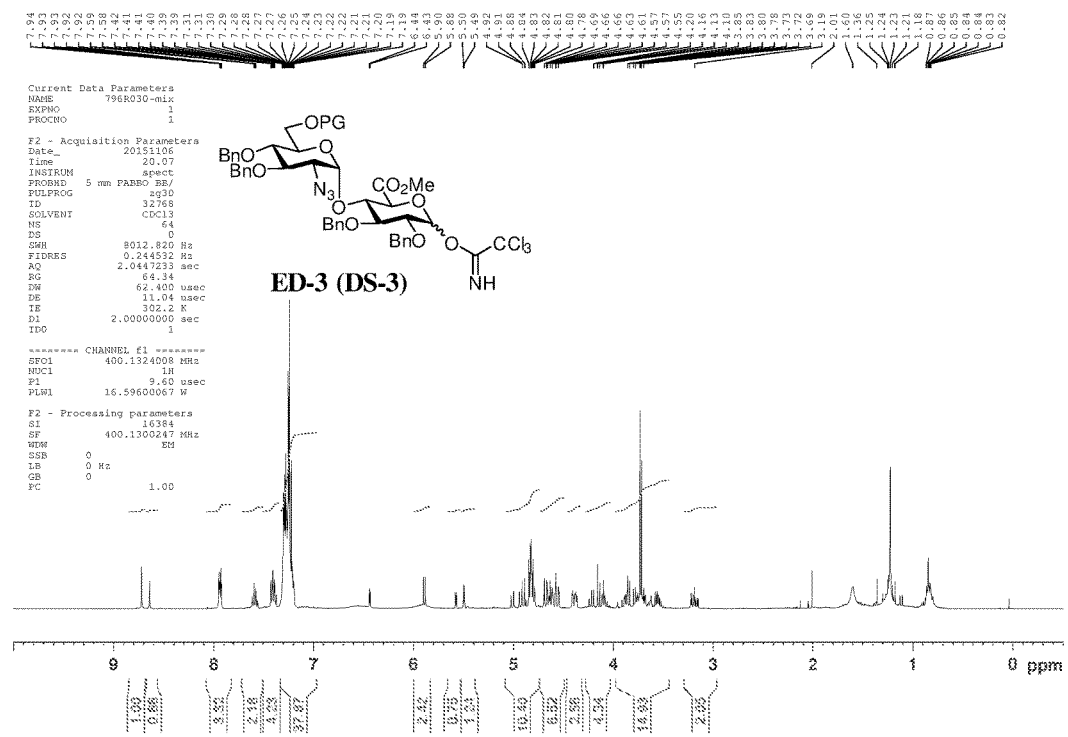
FIG. 33 is a $^1$H-NMR spectrum of Disaccharide ED-3.
Figure 34:
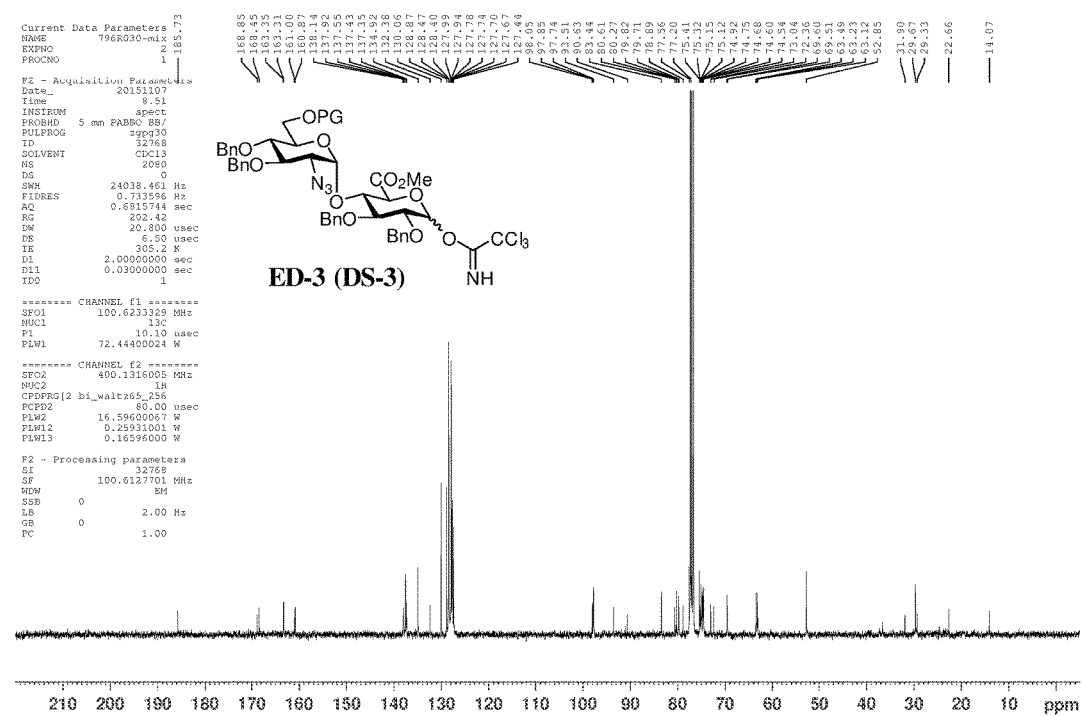
FIG. 34 is a $^{13}$C-NMR spectrum of Disaccharide ED-3.

1,1,1-Trichloroacetonitrile(TCA) (1000 ml), $Cs_2CO_3$ (69.4 g) and Disaccharide ED-2 (DS-2) in step 1 were added to a 2000 ml three-neck reaction flask and stirred. The reaction mixture was stirred for 30 min until completion checked by TLC (EA/hexane=1/3). 7% Sodium chloride(aq) (72 ml) was added to quench the reaction and stirred until $Cs_2CO_3$ dissolved completely, then stand for 20 min. The aqueous layer was extracted with TCA (15 ml). Collect all TCA solutions and added $MgSO_4$ (2 g) for 30 min to absorb water. Filtered the solution, then the filtrate was concentrated under vacuum (37 torr) at 40° C. DCM (1000 ml) was added to the residues and concentrated to almost dryness under vacuum. Repeat the concentration procedure with DCM (1000 ml) three times. Crude DS-3 (90 g) was obtained. The purified DS-3 (81 g) was obtained by flash column separation. (silica gel; gradient elution with mobile phase: EA/hexane=1/10, 1/5 (V/V)). The $^1$H-NMR (400 MHz, $CDCl_3$) of ED-3 is shown in FIG. 33. The $^{13}$C-NMR (100 MHz, $CDCl_3$) of ED-3 is shown in FIG. 34.

Step 4. Formation of Trisaccharide EDC-1 (TS-1)

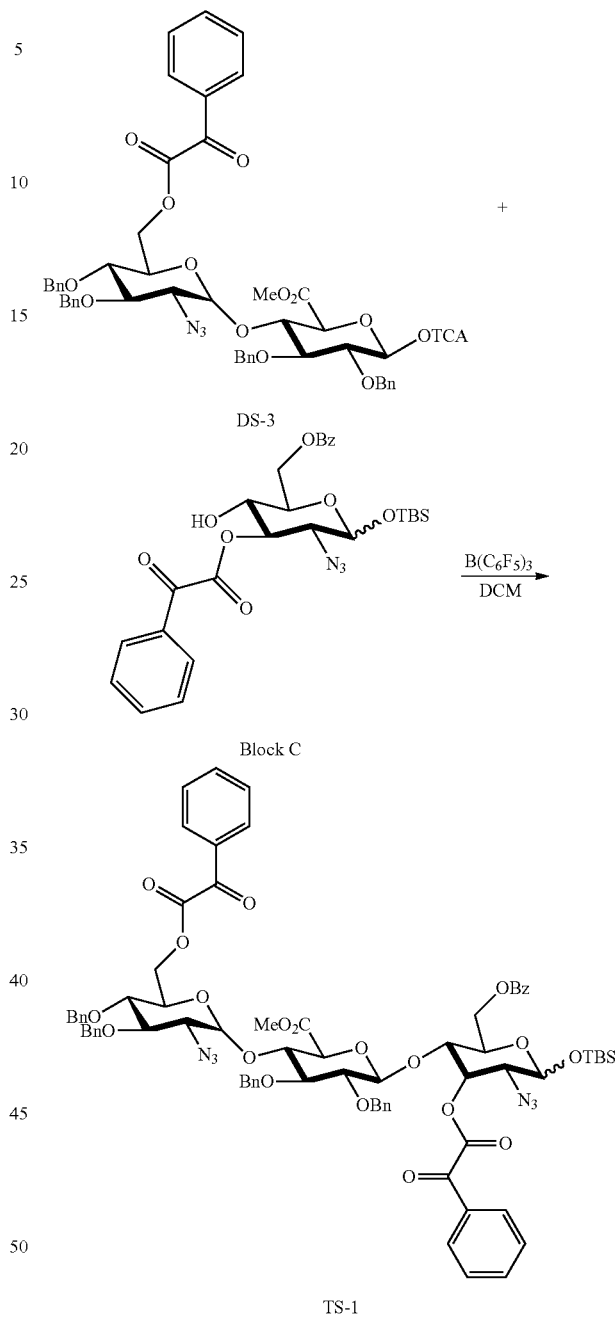

Figure 35:
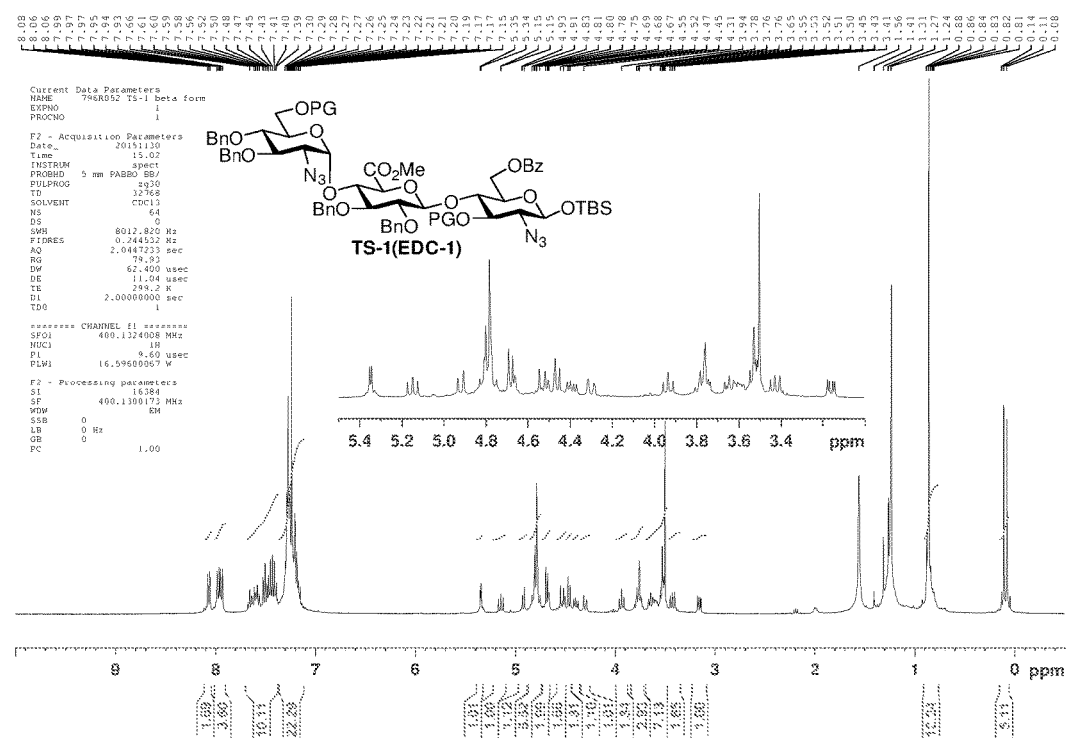
FIG. 35 is a $^1$H-NMR spectrum of Trisaccharide EDC-1.
Figure 36:
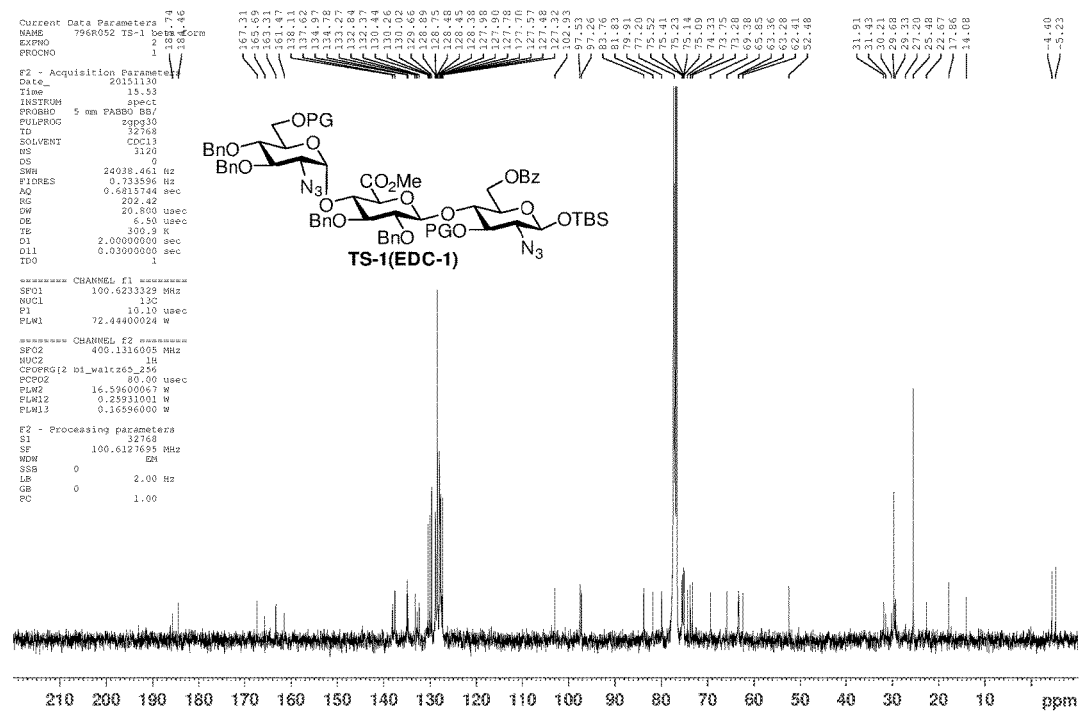
FIG. 36 is a $^{13}$C-NMR spectrum of Trisaccharide EDC-1.

Dichloromethane (300 ml), molecular sieve 4 Å (10 g), Tris(pentafluorophenyl) borane $(B(PhF_5)_3)$ (12.1 g) and Block C (48 g) were added to a 2000 ml three-neck reaction flask (A) and stirred for 30 min at 20~30° C. Dichloromethane (480 ml), molecular sieve 4 Å (16 g) and DS-3 (81 g) were added to a 1000 ml reaction flask (B) and stirred for 30 min at 20~30° C. The reaction solution in flask (A) was cooled to 5~10° C. (7° C.), then DS-3 in flask (B) was dropwisely added to the reaction solution (A) and stirred for 2 hours until completion checked by TLC (BuOAc/hexane=1/4). Triethylamine (10 ml) was added to quench the reaction. The solution was filtered to remove molecular sieve 4 Å. The resulting filtrate was concentrated to almost dryness under vacuum (30 torr) at 30° C. and crude TS-1 (β/α=84/16, 96 g) was obtained. The purified TS-1 (β form, 72 g) was obtained by flash column separation. (silica gel; gradient elution with mobile phase: EA/hexane=1/8, 1/6(V/V)). The $^1$H-NMR (400 MHz, CDCl$_3$) of EDC-1 is shown in FIG. 35. The $^{13}$C-NMR (100 MHz, CDCl$_3$) of EDC-1 is shown in FIG. 36.

Example 5: Preparation of Disaccharide ED-1

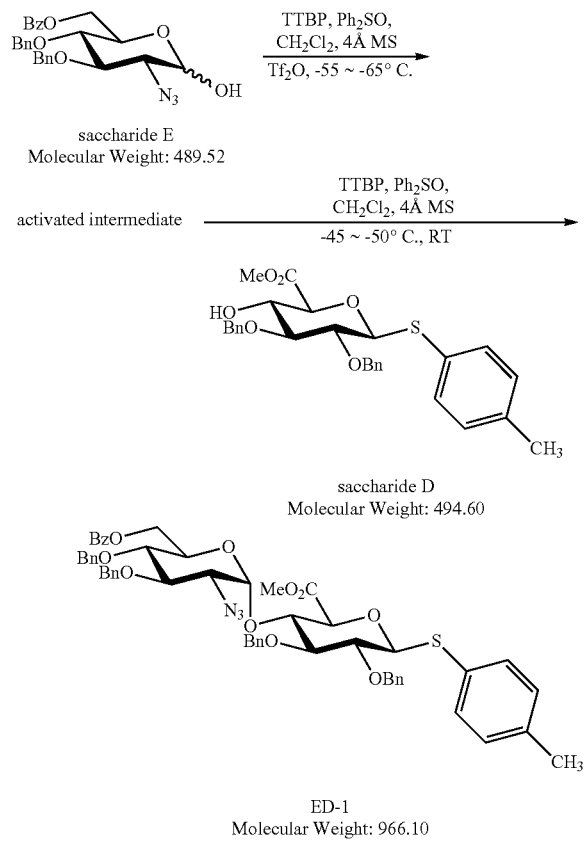

TABLE 1

| Reagent | Wt (g) | MW | eq |
| --- | --- | --- | --- |
| Saccharide E | 106.55 | 489.52 | 1 |
| 2,4,6-tri-tert-butyl-pyrimidine (TTBP) | 160.55 | 248.41 | 3 |
| Diphenyl sulfoxide (Ph$_2$SO) | 108.94 | 202.27 | 2.5 |
| Dichloromethane (CH$_2$Cl$_2$) | 1105 ml | — | 12 V |
| Trifluoromethanesulfonic anhydride (Tf$_2$O) | 85.1 | 282.14 | 1.4 |
| Saccharide D | 106.55 | 494.6 | 1 |
| Molecular sieve (4 Å MS) | 105.46 | — | 1 W |
| Triethylamine (TEA) | 85 ml | — | 0.8 V |

Procedure:
1. Saccharide D (106.55 g) was placed into a two-neck reaction flask (500 ml), then 4 Å A MS (52.73 g) and CH$_2$Cl$_2$ (160 ml) was added, and stirring for 30 min under room temperature. The reaction was sampled to check KF (KF NMT 0.03%).
2. A 2 L four-necked reaction flask was equipped with a mechanical stirrer and a vacuum pump. The stirrer is switched on to dry the reaction flask under high temperature and vacuum condition.
3. TTBP (160.55 g), Ph$_2$SO (108.94 g), saccharide E (105.46 g), 4 Å MS (52.73 g) and CH$_2$Cl$_2$ (1105 ml) were added into the reaction flask of step 2. Stirring for 30 min at room temperature. The reaction was sampled to check KF (KF NMT 0.03%).
4. When the temperature of the reaction solution reduced to −60~−65° C., Tf$_2$O (85.1 g) was added dropwise. The temperature was controlled below −55° C. and adding for 30 min during the feeding process, and controlled at −50° C. after adding completed.
5. The solution of saccharide D (106.55 g) in step 1 was added dropwise to the reaction flask. The temperature was controlled below −40° C. and adding for 20 min. After the adding completed, the cooling system was removed and let the temperature naturally return to room temperature. Stirring was continued for 18 hr.
6. The reaction was reacted under room temperature and sampled at 0.5 hr, 1.5 hr, 3 hr, 18 hr, respectively, to check extent of reaction by UPLC (sampling method: 15 drop of reaction solution+1 drop of TEA+5 drop of H$_2$O, organic layer was obtained and diluted 200× for UPLC). Processing to step 7 as the saccharideD/ED-1 (area) ratio remained constant.
7. TEA (85 ml) was added to reaction flask to quench the reaction, stirring for 30 min and then filtrated. H$_2$O (220 ml) was added to wash the filtration of organic solvent. The solution of organic layer was concentrated under reduced pressure until no distillate. Then, IPA (300 ml) was added. After dissolving completed, the solution was concentrated until no distillate to obtain yellow solid.
8. IPA (2100 ml) was added again (not completely dissolved) and heated to 72° C. to completely dissolved. The temperature was then cooling slowly. The solid started to precipitate as 63~64° C. Stirring for 2 hr at this temperature and cool down to room temperature. Stirring was continued for 2~3 hr.
9. The solution was filtrated. The resultant cake with IPA (105 ml). Vacuum drying the wet cake (vacuity <60 torr, temperature: 55~60° C., time: 3~4 hr), and sampling to measure LOD (LOD NMT 0.5%), to obtain white powder 145 g, yield 66~68%.

Example 6: Preparation of Disaccharide ED-2

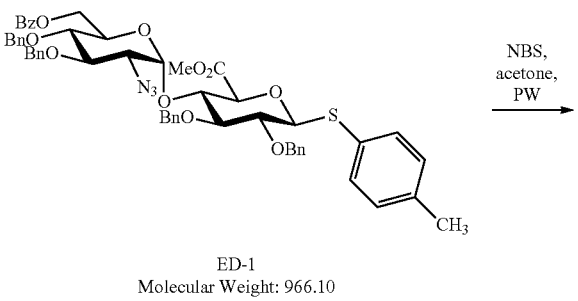

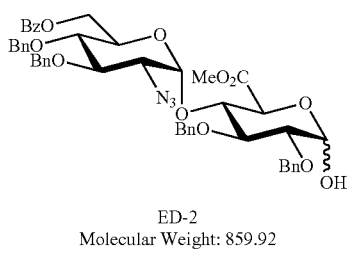

ED-2
Molecular Weight: 859.92

TABLE 2

| Reagent | Wt (g) | MW | eq |
|---|---|---|---|
| ED-1 | 145 | 966.1 | 1 |
| Acetone(ACT) | 2900 ml | — | 20 V |
| H₂O | 108.75 ml | — | 0.75 V |
| N-bromosuccinamide (NBS) | 106.85 | 177.99 | 4 |
| Dichloromethane (CH₂Cl₂) | 1500 ml | — | 10 V |

Procedure

1. A 5 L four-necked reaction flask was equipped with a mechanical stirrer and the stirrer was switched on to stir.
2. ED-1 (145 g), ACT (2900 ml), and H₂O (108.75 ml) were added to reaction flask and stirred to completely dissolve into clear solution.
3. As the temperature cooling down to −5~−10° C., NBS (106.85 g) was added in portions. The temperature was controlled below −5° C. during the adding process until the reaction solution turn into orange-red.
4. After complete adding, the solution was stirring at −5~−10° C. for 15 min and then sampled to check extent of reaction by TLC and UPLC (ED-1 NMT 1%).
5. 10% Na₂S₂O₃ (870 ml), and NaHCO₃(sat) (870 ml) were added to quench the reaction. Feeding will generate heat (exothermic). The temperature was controlled below 20° C. during feeding process. Color change of the reaction solution is as follows: orange-red→white and cloudy→yellow and cloudy→yellowish turbid solution.
6. The reaction solution was concentrated under reduced pressure to no ACT or other distillate (vacuity <80 torr, temperature: 35~40° C., time: 1 hr).
7. CH₂Cl₂ (750 ml) was added to the reaction solution of step 6 to extract twice. The organic layers were combined and extracted and washed with H₂O (360 ml) (2.5V).
8. MgSO₄ 50 g was added into organic layer to remove water. The reaction solution was stirred for 20~30 min and then filtrated. The filtrate was concentrated under reduced pressure (vacuity <80 torr, temperature: 45~50° C., time: 2 hr) to obtain viscous yellow foam (156 g).

Example 7: Preparation of Disaccharide ED-3

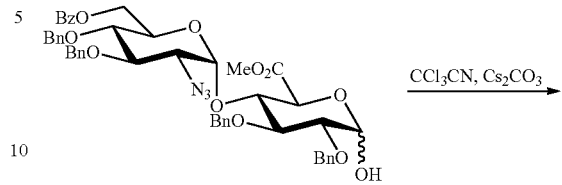

ED-2
Molecular Weight: 859.92

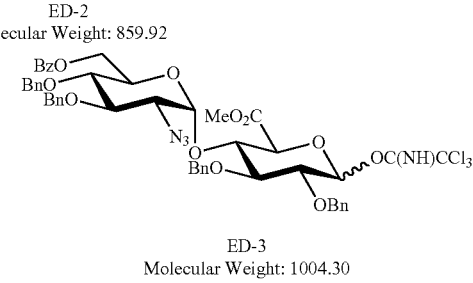

ED-3
Molecular Weight: 1004.30

TABLE 3

| Reagent | Wt (g) | MW | eq |
|---|---|---|---|
| ED-2 | 219 | 859.92 | 1 |
| 2,2,2-Trichloroacetonitrile (CCl₃CN) | 2190 ml | — | 10 V |
| Cesium carbonate(Cs₂CO₃) | 82.98 | 325.82 | 1 |
| Toluene | 2190 ml | — | 10 V |

Procedure

1. A 3 L four-necked reaction flask was equipped with a mechanical stirrer and a vacuum pump. The stirrer is switched on to dry the reaction flask under high temperature and vacuum condition.
2. ED-2 (219 g) and CCl₃CN (2190 ml) were added into reaction flask, and Cs₂CO₃ (82.98 g) was added. The color of solution slowly turned into brown. The solution was stirred at room temperature for 1~2 hr, and sampled to check extent of reaction by UPLC (ED-2 NMT 2%).
3. The reaction solution was concentrated under reduced pressure. The distillate was CCl₃CN and can be recycled and repeated use (vacuity <80 torr, temperature: 40~45° C.).
4. Toluene (2190 ml) and 10% NaCl (1752 ml) (8V) were added to extract. The reaction solution was stirred for 20 min for dissolving completely, and stood for 10~20 min to be separated into layers.
5. The organic layer was extracted and washed with 10% NaCl (1752 ml) (8V) each time, stirred for 20 min, and stood for 10~20 min to be separated into layers. The aqueous layer was sampled until pH 7~8.
6. MgSO₄ 66 g (0.3 W) was added into organic layer to remove water. After filtration, the filtrate was concentrated under reduced pressure (vacuity <80 torr, temperature: 45~50° C.). CH₂Cl₂ 330 ml was added and the solution was concentrated under reduced pressure each time. The concentration was repeated 3 times to obtain viscous foam.

Recover of 2,2,2-Trichloroacetonitrile(TCA) distilled from organic layer concentration: distillation at normal pressure, external temperature 90° C., internal temperature 83° C., vapor temperature 79° C. The purity of distillate is measured by GC (NLT 95%).

Example 8: Preparation of Trisaccharide EDC-1

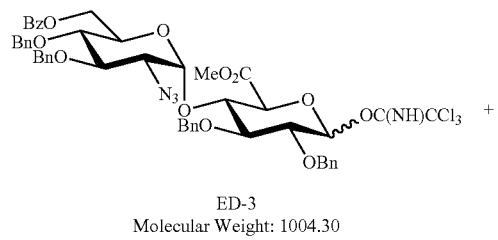

ED-3
Molecular Weight: 1004.30

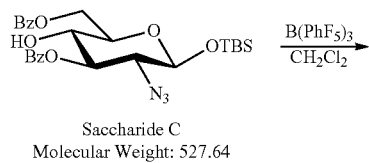

Saccharide C
Molecular Weight: 527.64

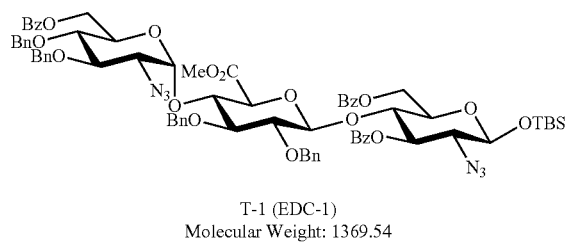

T-1 (EDC-1)
Molecular Weight: 1369.54

TABLE 4

| Reagent | Wt (g) | MW | eq |
| --- | --- | --- | --- |
| ED-3 | 255.77 | 1004.3 | 1 |
| Saccharide C | 403.13 | 527.64 | 3 |
| Dichloromethane (CH$_2$Cl$_2$) | 1280 ml | — | 5 V |
| Molecular sieve (4ÅMS) | 102.31 | — | 0.4 W |
| Tris(pentafluoroPhenyl)borane B(PhF$_5$)$_3$ | 39.12 | 511.98 | 0.3 |

Procedure

1. A 3 L four-necked reaction flask was equipped with a mechanical stirrer and a vacuum pump. The stirrer is switched on to dry the reaction flask under high temperature and vacuum condition.
2. Saccharide C (403.13 g), CH$_2$Cl$_2$ (640 ml), and 4 ÅMS (75 g) were added, stirring at room for 30 min. The reaction was sampled to check KF (KF NMT 0.03%).
3. The reaction solution was cooling down to 0~2° C., and B(PhF$_5$)$_3$ (39.12 g) was added.
4. ED-3 (255.77 g), CH$_2$Cl$_2$ (640 ml), and 4 ÅMS (27.3 g) were mixed, and sampled to check KF (KF NMT 0.03%). If not qualified, 4 ÅMS 27.3 g, stirring for 20 min and sampled to check KF (KF NMT 0.03%).

The reaction solution was added dropwise to the reaction flask of step 3. In the feeding progress, the temperature was controlled at 0~2° C., feeding time was 20~25 min. After complete adding, stirring at this temperature for 1~2 hr. The solution was sampled to check by UPLC to confirm saccharide C/T-1 area ratio remained unchanged.
5. TEA (51 ml) was added to quench the reaction, stirring for 5~10 min.
6. The reaction solution of step 5 was filtrated to obtain cake (4 ÅMS) and washed with CH$_2$Cl$_2$ (0.5V) (130 ml).
7. The resultant filtrate was extracted and washed with 6% NaHCO$_3$, the aqueous layer was re-extracted with CH$_2$Cl$_2$ (255 ml) (1V).
8. The organic layers were combined, and concentrated under reduced temperature (vacuity <50 torr, temperature: 40~45° C.) to obtain brown viscous solid (743 g).
9. Column purification Silica gel (40~63 μm): 20 W The crude EDC-1 (743 g) was dissolved in toluene (1114 ml), heated to 40~45° C. for dissolving, and loaded to column one finger width high.

(1) Elution: Toluene→Ethylacetate/Toluene=1/50

Flow rate: 25 min/CV. (CV=column volume)

The column separation was monitored by UPLC, and the fractions containing EDC-1 (α/β) was collected and concentrated under reduced pressure. Washed with CH$_2$Cl$_2$ (200 ml) and concentrated under reduced pressure each time, repeated 3 times (vacuity: 10~15 torr, temperature: 45° C.) to obtain yellow foam (209 g).

(2) Elution: Eluting saccharide C with Ethylacetate/Toluene=1/1 and recover saccharide C.
10. Column purification Silica gel (40~63 μm):80 W 340 g EDC-1 (α/β) was dissolved in 220 ml CH$_2$Cl$_2$, and loaded to column one finger width high.

(1) Elution: hexanes→n-BuOAc/Hex=1/6→EA

Flow rate: 25 min/CV. (CV=column volume)

The column separation was monitored by UPLC, and the fractions containing EDC-1 (β) was collected and concentrated under reduced pressure. Washed with CH$_2$Cl$_2$ (200 ml) and concentrated under reduced pressure each time, repeated 3 times (vacuity: 10~15 torr, temperature: 45° C.) to obtain pale yellow foam (175 g). After concentration under reduced pressure, the mixed EDC-1 (α/β) can be combine with the next batch of EDC-1 (α/β) to be separate and purified by column.

(2) Elution: Eluting EDC-1 (α) with Ethylacetate.
11. Recover of saccharide C: saccharide C separated by column was collected, Tol (1V) and Hex (3V) were added. The solution was heated to 45~50° C. and stirred for 30 min. Then, the solution was cooling down to 20~25° C. and stirred for 1~2 hr. The solution was further cooling down to 0~5° C. and stirred for 2 hr, then filtrated. The resultant wet cake was added with Hex (3V), and heated to 45~50° C. and stirred for 30 min. The solution was cooling down to 20~25° C., stirred for 1~2 hr, and then filtrated. The cake was dried (vacuum drying: 10~15 torr, temperature: 45° C.) and Purity was measured by UPLC (Purity NLT 98%).

Example 9: Preparation of Disaccharide BA-2

Step 1: Formation of Disaccharide BA-1

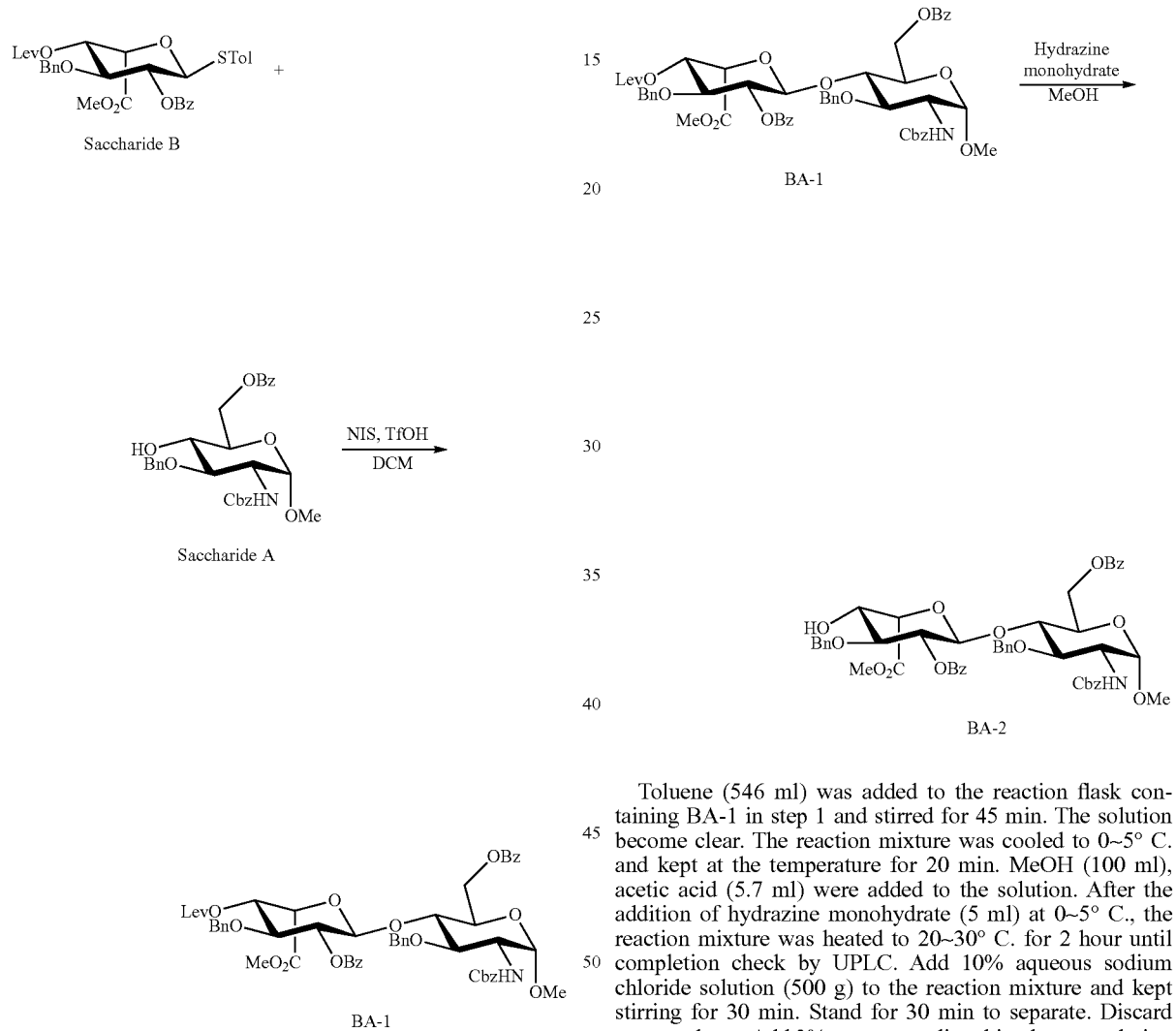

Toluene (1250 ml) was added to the reaction flask. Saccharide A (50.3 g), saccharide B (48.8 g) was added and stirred for 30 min. Remove the water from the reaction mixture by azeotropic distillation of toluene under vacuum three times. Dichloromethane (500 ml), dried activated molecular sieve 4 Å (10 g) was added and stirred for 10 min and cooled the temperature at −10° C. N-iodosuccinimide (NIS) (25.2 g) was added and stirring continuously for 20 min. After dropwise addition of trifluoromethanesulfonic acid (TfOH) (2.33 ml), the reaction mixture was kept stirring at −10~−5° C. until completion checked by UPLC. The reaction mixture was quenched with 8% aqueous sodium bicarbonate (250 g) solution, and then diluted with dichloromethane and filtered through a celite pad. The filtrate was washed with a 8% aqueous sodium bicarbonate (250 g) and sodium thiosulfate (250 g) solution, saturated brine solution, water and dried over MgSO4, then evaporated. Toluene (500 ml) was added to the reaction flask and evaporated to dryness at 45° C. under vacuum.

Step 2: Formation of Disaccharide BA-2

Figure 37:
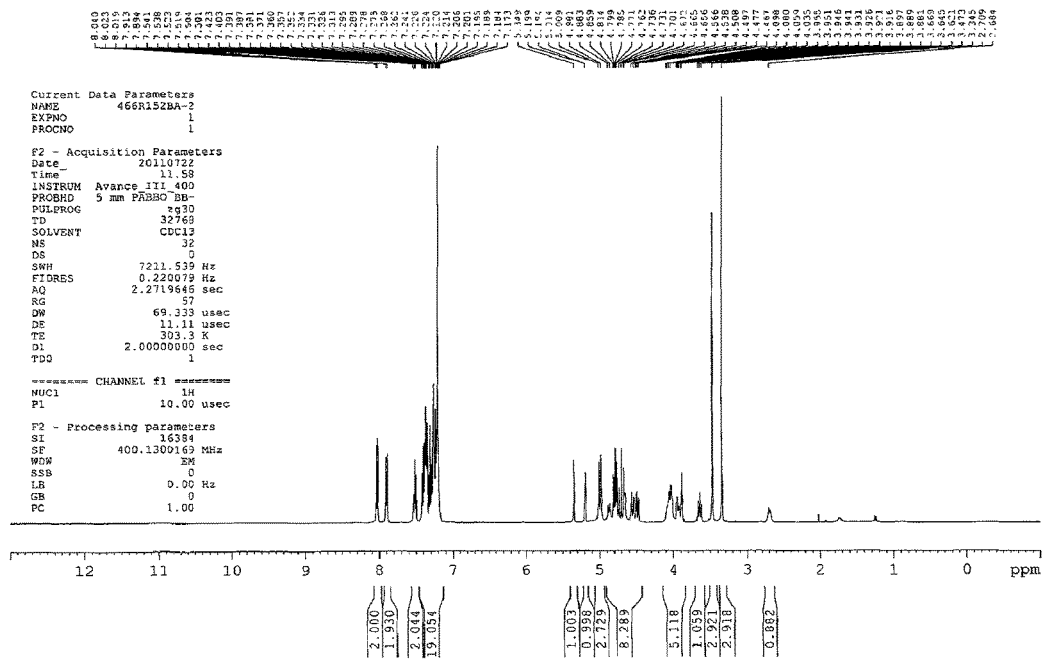
FIG. 37 is a $^1$H-NMR spectrum of Disaccharide BA-2.
Figure 38:
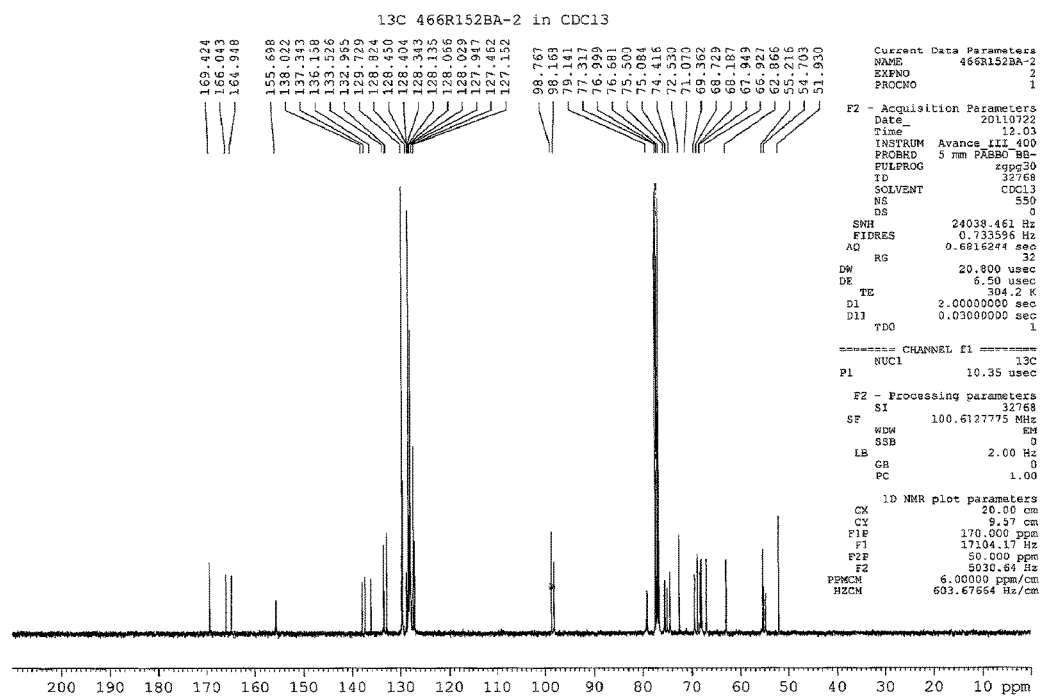
FIG. 38 is a $^{13}$C-NMR spectrum of Disaccharide BA-2.

Toluene (546 ml) was added to the reaction flask containing BA-1 in step 1 and stirred for 45 min. The solution become clear. The reaction mixture was cooled to 0~5° C. and kept at the temperature for 20 min. MeOH (100 ml), acetic acid (5.7 ml) were added to the solution. After the addition of hydrazine monohydrate (5 ml) at 0~5° C., the reaction mixture was heated to 20~30° C. for 2 hour until completion check by UPLC. Add 10% aqueous sodium chloride solution (500 g) to the reaction mixture and kept stirring for 30 min. Stand for 30 min to separate. Discard aqueous layer. Add 2% aqueous sodium bicarbonate solution (513 g) and stirred for 30 min. Stand for 30 min to separate again. Discard aqueous layer, then add water (500 g) to the organic layer and kept stirring about 30 min. Repeat the wash procedure with water twice. The resulting organic solution was evaporated to dryness under vacuum and crude BA-2 was obtained. The $^1$H-NMR (400 MHz, CDCl$_3$) of BA-2 is shown in FIG. 37. The $^{13}$C-NMR (100 MHz, CDCl$_3$) of BA-2 is shown in FIG. 38.

Step 3: Purification of BA-2

The pure BA-2 powder was achieved by purification from chromatographic separation (Ethylacetate, hexanes, silica gel) and by crystallization from toluene and hexanes solution. Yield (85% from glycosylation of saccharide B and saccharide A).

Example 10: Preparation of Pentasaccharide EDCBA-1 (PS-1)
Step 1. Formation of Trisaccharide EDC-2 (TS-2)
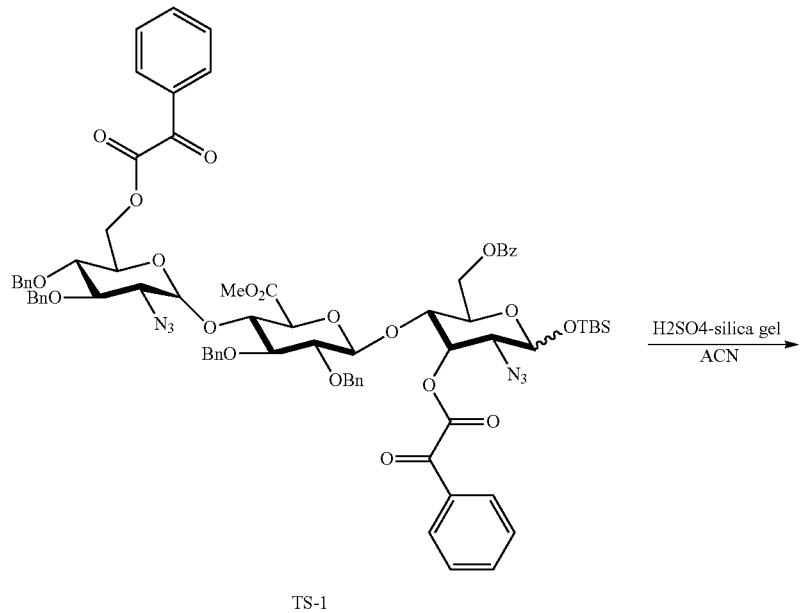
TS-1
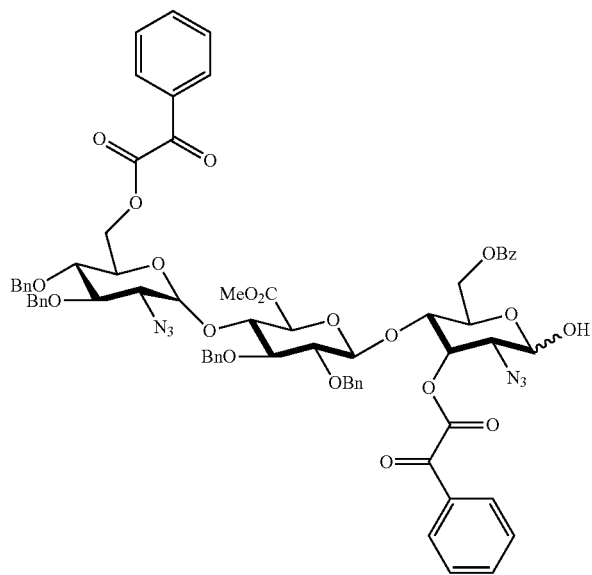
TS-2

Acetonitrile(ACN) (720 ml), TS-1 (72 g) and dried H₂SO₄-silica gel (430 g) were added to a 2000 ml three-neck reaction flask and stirred for 4.5 hours at 20~30° C. until completion checked by TLC (EA/hexane=1/3). The solution was filtered by suction to get rid of H₂SO₄-silica gel. Toluene (800 ml), sodium bicarbonate(sat) (400 ml) were added to the filtrate and stirred for 15 min, then stand for 15 min. Collect all organic layers and added MgSO₄ (40 g) for 30 min to absorb water. Filtered the solution, then the filtrate was concentrated to almost dryness under vacuum (37 torr) at 40° C. Crude TS-2 (70 g) was obtained.

Step 2. Formation of Trisaccharide EDC-3(TS-3)

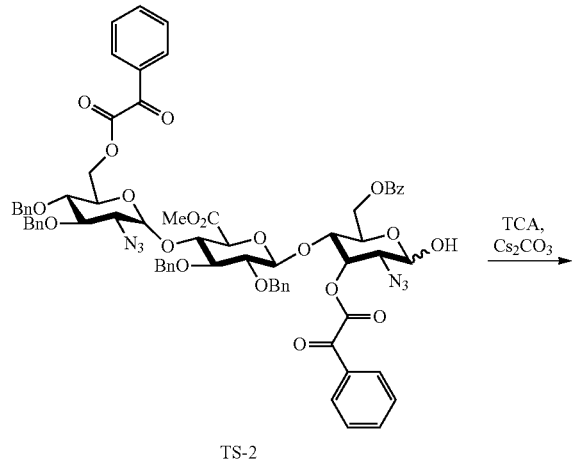

TS-2

-continued

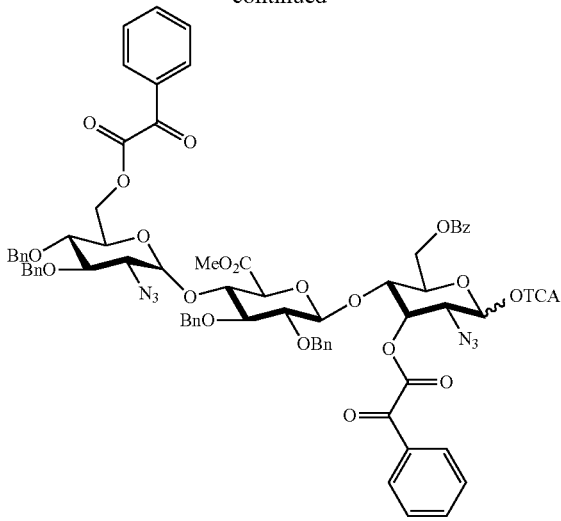

TS-3

1,1,1-trichloroacetonitrile(TCA) (500 ml), crude TS-2 (70 g) in step 1 and Cs₂CO₃ (16.8 g) were added to the reaction flask and stirred for 2 hours at 20~25° C. until TS-2 disappeared on TLC plate (mobile phase: ACT/hexane=1/5). 7% NaCl (aq) was added to the solution and stirred for 15 min, then stand for 15 min. TCA (100 ml) was added aqueous layer and stirred for 15 min, then stand for 15 min. Collect all organic layers (TCA solution) and added MgSO₄ (20 g) for 30 min to absorb water. Filtered the solution, then the filtrate was concentrated under vacuum (30 torr) at 40° C. Crude TS-3 (72 g) was obtained. The purified TS-3 (60 g) was obtained by flash column separation. (silica gel; mobile phase: EA/hexane=1/3 (V/V)).

Step 3. Formation of Pentasaccharide EDCBA-1 (PS-1, P-1)

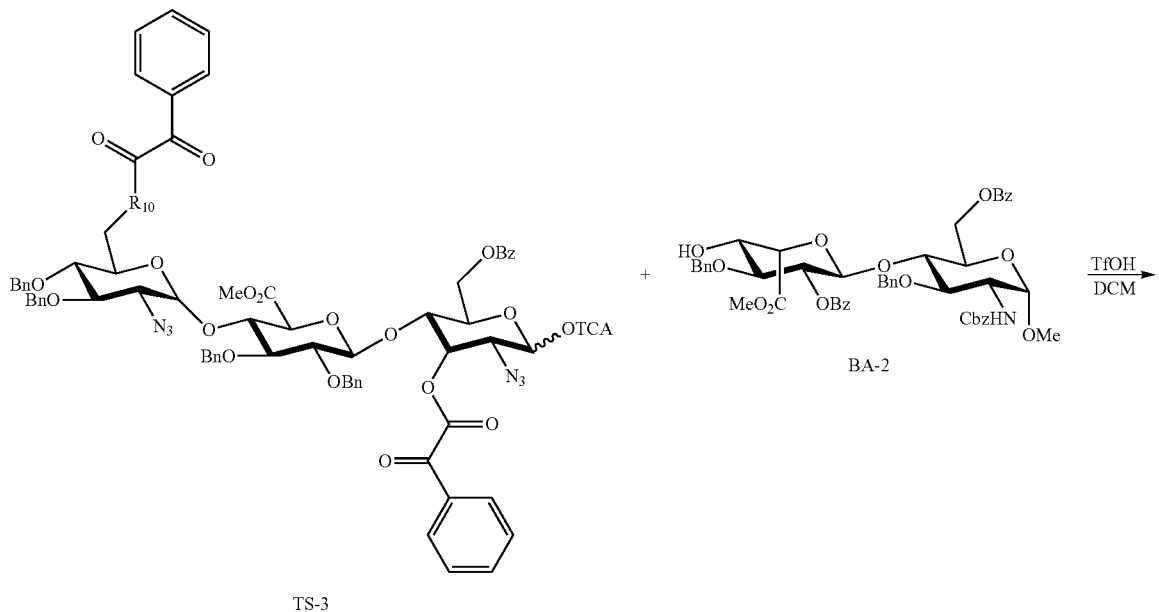

TS-3

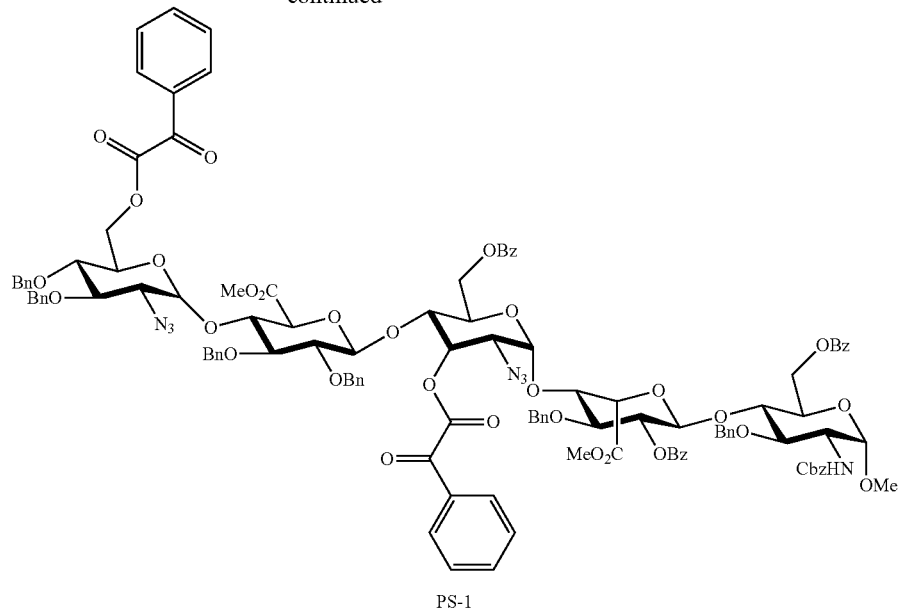

PS-1

Figure 39:
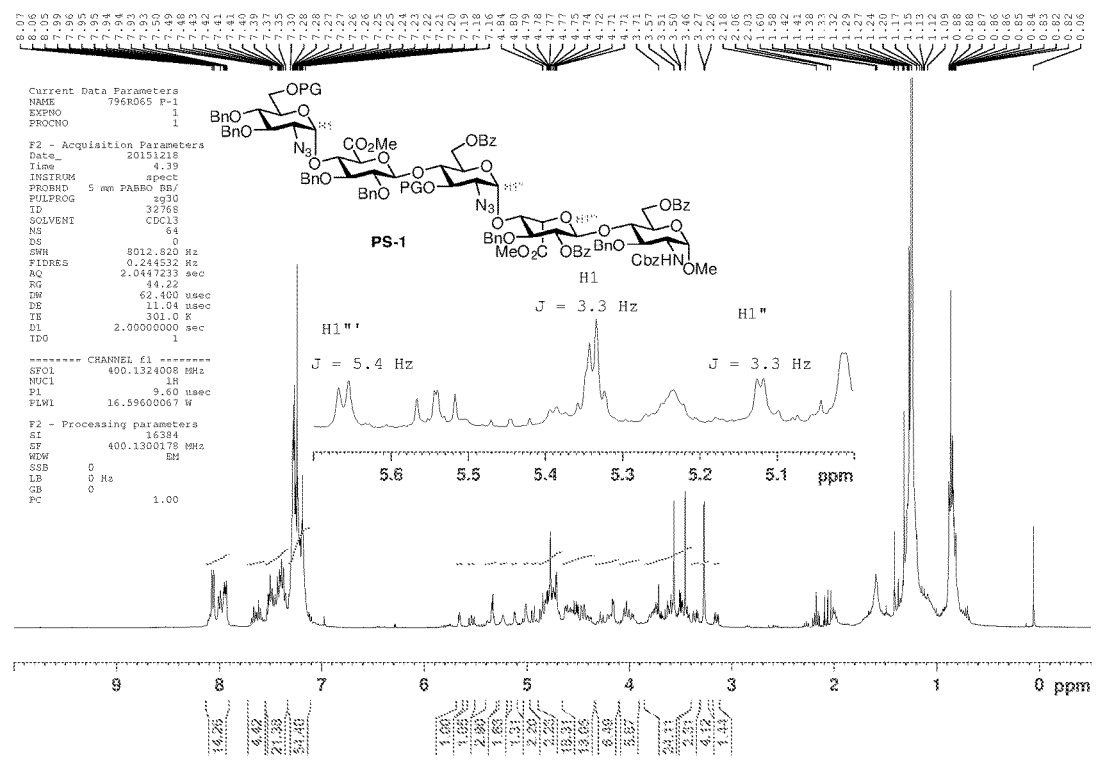
FIG. 39 is a $^1$H-NMR spectrum of Pentasaccharide PS-1.
Figure 40:
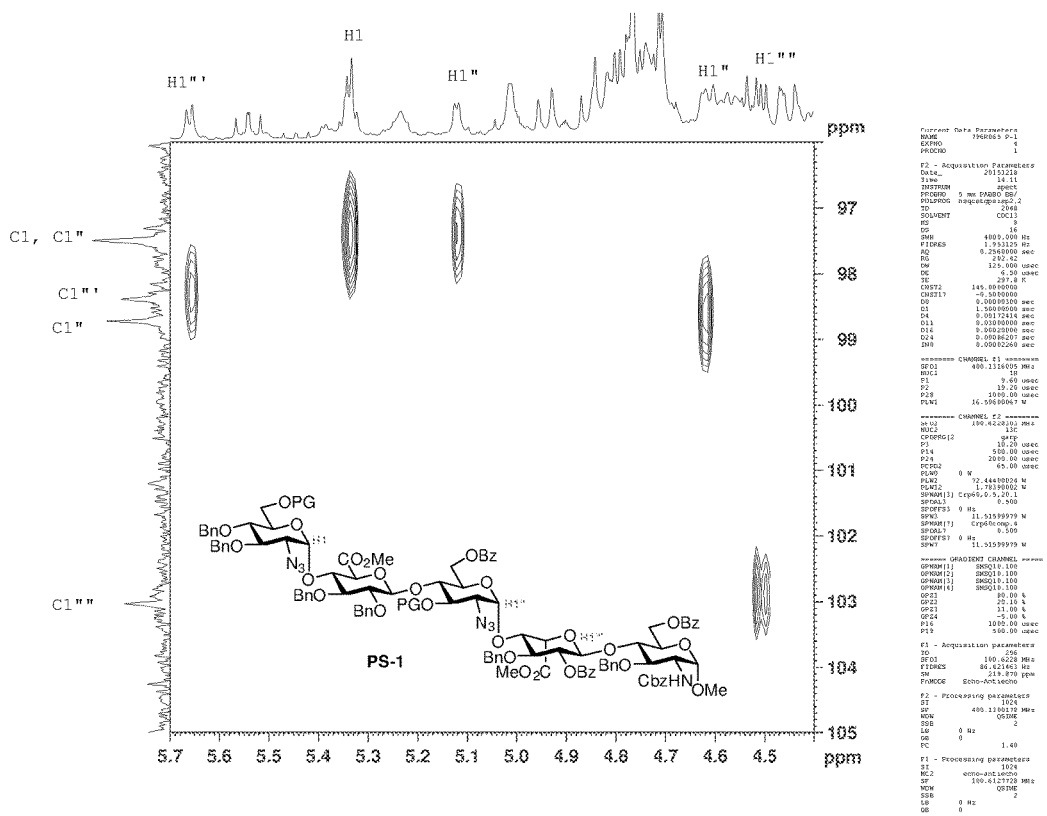
FIG. 40 is a $^1$H-$^{13}$C COSY spectrum of Pentasaccharide PS-1.
Figure 41:
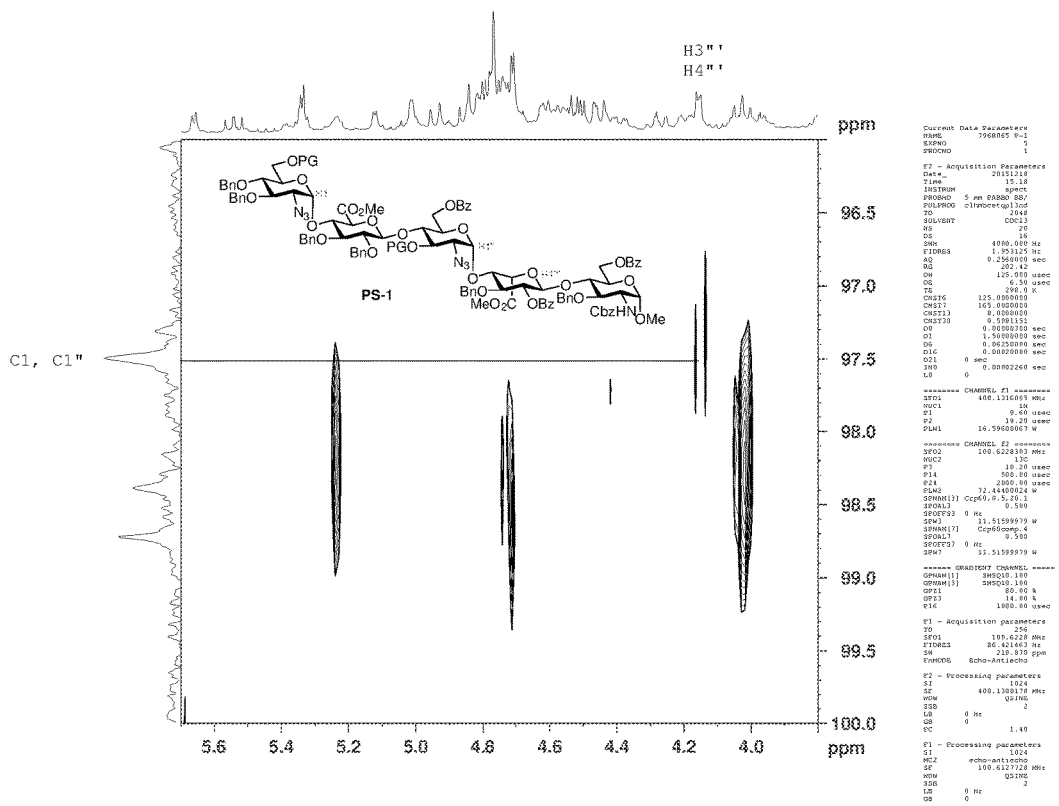
FIG. 41 is a $^1$H-$^{13}$C HMBC spectrum of Pentasaccharide PS-1.

Dichloromethane(DCM) (420 ml), Disaccharide BA-2 (39 g), TS-3 (60 g) in step 3 and molecular sieve 4 Å (12 g) were added to a 1000 ml reaction flask and stirred for 30 min, then the reaction mixture was dried by heat gun under vacuum for 10 min. The solution was cooled to −25° C. and stirred for 5 min, then trifluoromethanesulfonic acid (3.6 ml) was added by injection. After the addition, the solution was stirred for 30 min until completion checked by TLC (EA/hexane=1/3). Triethylamine(TEA) (8 ml) was added to quench the reaction at −25° C. The solution was filtered by suction to remove molecular sieve 4 Å. The filtrate was concentrated under vacuum (30 torr) at 25° C. Crude PS-1 (60 g) was obtained. The purified PS-1 (55 g) was obtained by flash column separation. (silica gel; mobile phase: DCM/EA/hexane=1/1/3(V/V/V)). The $^1$H-NMR (400 MHz, CDCl$_3$) of PS-1 is shown in FIG. 39. The $^1$H-$^{13}$C COSY of PS-1 is shown in FIG. 40. The $^1$H-$^{13}$C HMBC of PS-1 is shown in FIG. 41.

Figure 17:
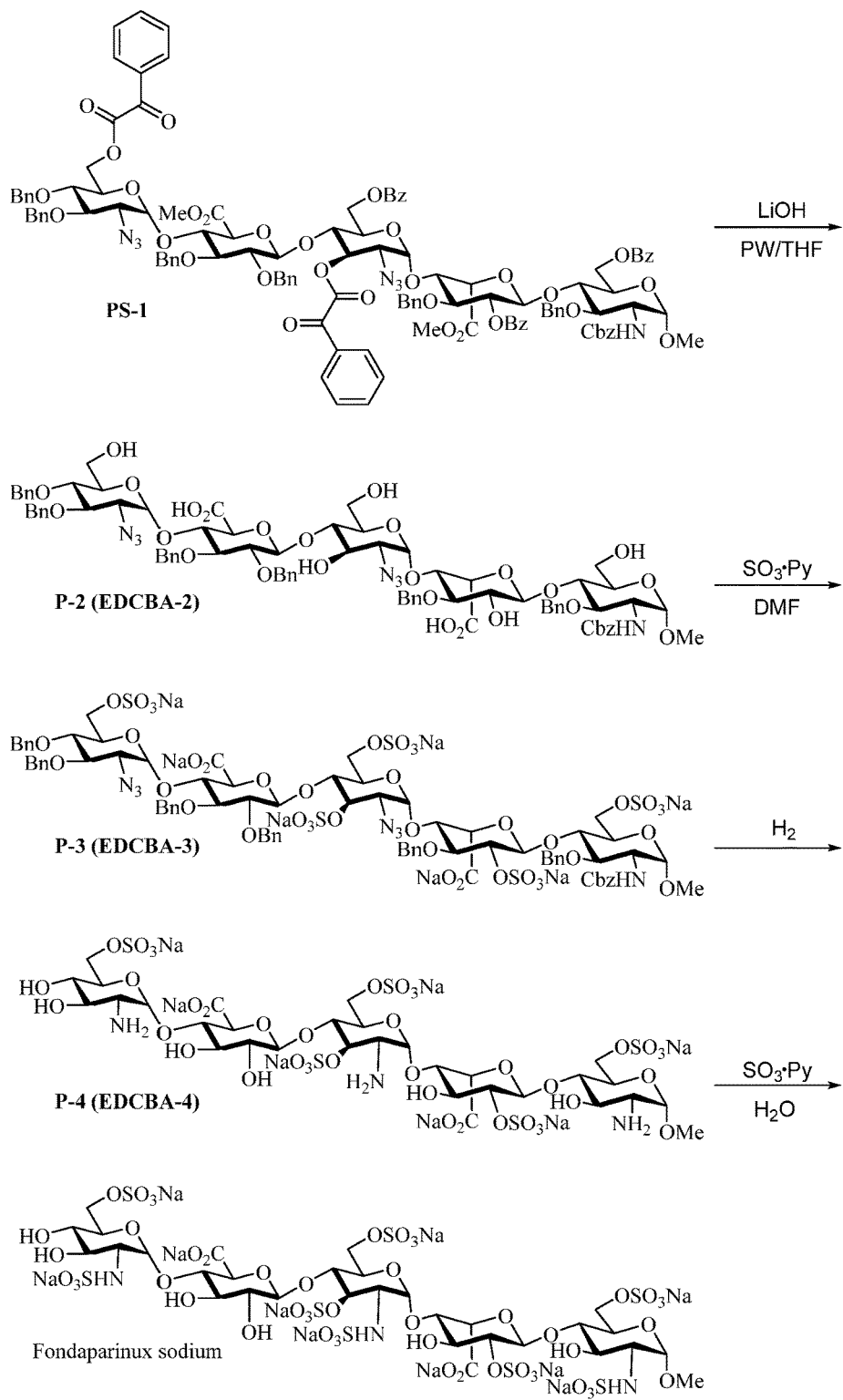
FIG. 17 illustrates the preparation of Fondaparinux Sodium.

Pentasaccharide EDCBA-1 (PS-1) is further for the preparation of Fondapariux Sodium as the process illustrated in FIG. 17.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

What is claimed is:

1. A trisaccharide of Formula V

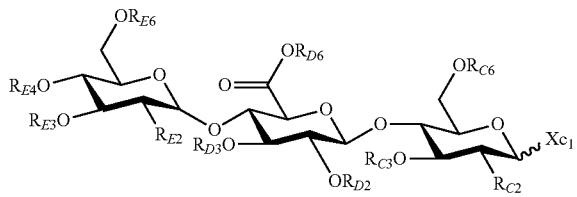

Formula V wherein $X_{C1}$ is selected from a hydroxyl group; thioalkyl, thioaryl, halogen, trichloroacetimidoyl, phosphate and phosphate ester leaving groups, or a tert-butyldiphenylsilyloxy or other substituted silyloxy protecting groups; and the stereochemistry may be alpha or beta;

$R_{C2}$ is selected from an azido function, an amine; NH-Dde or NH-DTPM group, or $R_{C2}$ and $R_{C3}$ can combine together to form a cyclic carbamate;

$R_{C3}$ is selected from an azulen-1-yl-oxo-acetyl (Az) protecting group or other substituted Az protecting group, alkyl 2-oxoacyl protecting group or other substituted alkyl protecting group, aryl 2-oxoacyl protecting group or other substituted aryl protecting group;

$R_{C6}$ is selected from an azulen-1-yl-oxo-acetyl (Az) protecting group or other substituted Az protecting group, alkyl 2-oxoacyl protecting group or other substituted alkyl protecting group, aryl 2-oxoacyl protecting group or other substituted aryl protecting group;

$R_{D2}$ is selected from 4-methoxyphenyl; benzyl, substituted benzyl groups; alkylacyl, arylacyl and alkylarylacyl, or substituted alkylacyl, arylacyl and alkylarylacyl protecting groups; carbonate protecting groups, silyl protecting groups, carbamate protecting groups, $C_3$-$C_5$ alkenyl;

$R_{D3}$ is selected from 4-methoxyphenyl; benzyl, substituted benzyl groups; alkylacyl, arylacyl and alkylarylacyl, or substituted alkylacyl, arylacyl and alkylarylacyl protecting groups; carbonate protecting groups;

$R_{D6}$ is selected from methyl, $C_2$-$C_5$ alkyl; substituted alkyl, $C_3$-$C_5$ alkenyl; or, benzyl and substituted benzyl groups;

$R_{E2}$ is selected from an azido function, an amine; NH-Dde or NH-DTPM group, or $R_{E2}$ and $R_{E3}$ can combine together to form a cyclic carbamate;

$R_{E3}$ is selected from benzyl or substituted benzyl protecting group, allyl, or allyloxycarbonyl, or $R_{E2}$ and $R_{E3}$ can combine together to form a cyclic carbamate;

$R_{E4}$ is selected from a benzyl, or substituted benzyl protecting group, allyl, or allyloxycarbonyl; and $R_{E6}$ is selected from 4-methoxyphenyl; substituted benzyl groups; alkylacyl, arylacyl, alkylarylacyl, substituted alkylacyl, arylacyl or alkylarylacyl protecting groups; an azulen-1-yl-oxo-acetyl (Az) protecting group or other substituted Az protecting group, alkyl 2-oxoacyl protecting group or other substituted alkyl protecting group, aryl 2-oxoacyl protecting group or other substituted aryl protecting group; carbonate protecting groups; a tert-butyldiphenylsilyloxy or substituted siloxy protecting groups, allyl, methoxymethyl, methoxyethyl, or benzyloxymethyl, provided that at least one of $R_{C3}$, $R_{C6}$ and $R_{E3}$ is alkyl 2-oxoacyl protecting group

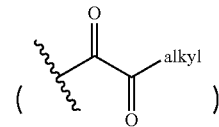

or aryl 2-oxoacyl protecting group

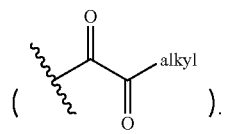

\* \* \* \* \*